US008895753B2

(12) United States Patent
Yoshida et al.

(10) Patent No.: US 8,895,753 B2
(45) Date of Patent: Nov. 25, 2014

(54) S1P RECEPTOR MODULATING AGENT

(71) Applicant: Meiji Seika Pharma Co., Ltd., Tokyo-to (JP)

(72) Inventors: Satoshi Yoshida, Kanagawa-ken (JP); Tomohisa Ninomiya, Kanagawa-ken (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/723,900

(22) Filed: Dec. 21, 2012

(65) Prior Publication Data

US 2013/0217663 A1 Aug. 22, 2013

Related U.S. Application Data

(60) Provisional application No. 61/638,689, filed on Apr. 26, 2012.

(30) Foreign Application Priority Data

Dec. 23, 2011 (JP) ................................. 2011-282476

(51) Int. Cl.
*C07D 417/10* (2006.01)
*C07D 417/14* (2006.01)

(52) U.S. Cl.
CPC ............ *C07D 417/10* (2013.01); *C07D 417/14* (2013.01)
USPC ............ 548/202; 514/326; 514/365; 546/209

(58) Field of Classification Search
CPC ............................ C07D 417/10; C07D 417/14
USPC ........................................................ 548/202
See application file for complete search history.

(56) References Cited

U.S. PATENT DOCUMENTS 8,389,508 B2 * 3/2013 Deng et al. ............... 514/210.18

FOREIGN PATENT DOCUMENTS

| WO | 2003/105771 | 12/2003 |
| WO | 2010/043000 | 4/2010 |
| WO | 2011/134280 | 11/2011 |

OTHER PUBLICATIONS

Doan et al., The Journal of Clinical Pharmacology, 2005, 45, pp. 751-762.*
Mandala et al., "Alteration of Lymphocyte Trafficking by Sphingosine-1-Phosphate Receptor Agonists", Science, vol. 296, Apr. 12, 2002, pp. 346-349.
Budde et al., "First Human Trial of FTY720, a Novel Immunomodulator, in Stable Renal Transplant Patients", Journal of the American Society of Nephrology, vol. 13, No. 4, 2002, pp. 1073-1083.
Sanna et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279, No. 14, Apr. 2, 2004, pp. 13839-13848.
Himmel et al., "Evidence for Edg-3 Receptor-Mediated Activation of $I_{K,ACh}$ by Sphingosine-1-Phosphate in Human Atrial Cardiomyocytes", Molecular Pharmacology, vol. 58, 2000, pp. 449-454.
Li et al., "Discovery of Potent 3,5-Diphenyl-1,2,4-oxadiazole Sphingosine-1-phosphate-1 ($S1P_1$) Receptor Agonists with Exceptional Selectivity against $S1P_2$ and $S1P_3$,", Journal of Medical Chemistry, vol. 48, No. 20, Oct. 6, 2005, pp. 6169-6173.

* cited by examiner

*Primary Examiner* — Laura L. Stockton
(74) *Attorney, Agent, or Firm* — Wenderoth, Lind & Ponack, L.L.P.

(57) ABSTRACT

An object of the present invention is to provide a compound having a modulating activity at an S1P receptor which is useful for preventing and treating autoimmune diseases, allergic diseases, and the like. According to the present invention, a compound represented by formula (I) or a pharmaceutically acceptable salt thereof is provided.

[Compound 1]

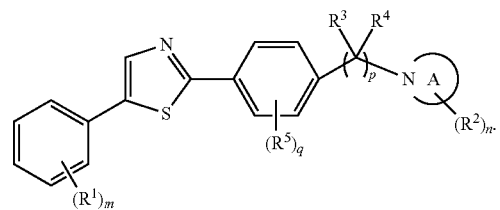

(I)

7 Claims, No Drawings

S1P RECEPTOR MODULATING AGENT

CROSS-REFERENCE TO RELATED APPLICATIONS

The present application claims to enjoy the benefit of prior Japanese Patent Application No. 2011-282476 filed on Dec. 23, 2011 and provisional application U.S. 61/638,689 filed on Apr. 26, 2011. The full disclosures of these prior application and provisional application are incorporated as a part of the present description by reference herein.

FIELD OF THE INVENTION

The present invention relates to a novel thiazole derivative having modulating activity for a sphingosine-1-phosphate (hereinafter referred to as S1P) receptor and excellent selectivity for an S1P1 receptor, and to a pharmaceutical composition comprising the said novel thiazole derivative as an active ingredient.

BACKGROUND ART

Although the causes of autoimmune diseases such as rheumatoid arthritis and systemic lupus erythematosus, and allergic diseases such as asthma and atopic dermatitis vary depending on their conditions, these diseases develop immunological disorders with symptoms in particular tissues or systemically caused by consequently aberrant immune responses. Conventionally, anti-inflammatory drugs such as steroid preparations and non-steroid anti-inflammatory drugs (NSAIDs) have been used to suppress the inflammatory responses resulting from over-responses of the immune system. However, these drugs are used only as symptomatic therapy, and their advantageous effects are limited and accompanied by no negligible adverse effects. Moreover, it has been known that disease-modifying anti-rheumatic drugs (DMARDs) that are commonly used as therapeutic agents for rheumatoid arthritis exert their effects by inhibiting differentiation/proliferation of lymphocytic cells that play a major role in immune responses. However, it is also known that serious adverse effects such as myelosuppression are induced because of their non-specific inhibition of various cell proliferations.

Recently, Fingolimod (or FTY-720), which was approved as a pharmaceutical agent for multiple sclerosis, is of particular interest as a pharmaceutical agent with a novel mechanism which regulates immunity without depletion of lymphocytic cells due to cell death and the like by controlling localization of lymphocytic cells. However, the use of Fingolimod has become controversial since serious adverse effects centered on the cardiovascular system such as bradycardia and cardiac arrhythmia have been observed (Non-Patent Document 1).

An S1P receptor is a G protein-coupled receptor that exists on cellular membranes, and five subtypes of the receptor (S1P1, S1P2, S1P3, S1P4, S1P5, AKA endothelial differentiation gene; EDG-1, EDG-5, EDG-3, EDG-6 and EDG-8) are identified. It is known that Fingolimod phosphorylated in vivo binds to S1P1, S1P3, S1P4, and S1P5 receptors, and acts as an agonist.

Phosphorylated Fingolimod sequestrates lymphocytic cells to secondary lymphoid tissues by inducing the accelerated cellular uptake mainly mediated by an S1P1 receptor, thus exerting potent immunosuppressive activity (Non-Patent Document 2). On the other hand, it has been shown that phosphorylated Fingolimod induces adverse effects such as bradycardia presumably mediated by an S1P3 receptor by animal experiments using an S1P1 receptor selective agonist, or by Patch clamp experiments using an S1P3 receptor selective antagonist, and moreover, by using an S1P3 receptor knockout animal model (Non-Patent Documents 3&4). More specifically, the efficacy of Fingolimod based on its immunosuppressive acting is mainly exerted by sequestering lymphocytic cells, which play a pivotal role in immune response, to secondary lymphoid tissues by controlling an S1P1 receptor. Meanwhile, adverse effects such as bradycardia and cardiac arrhythmia are more likely attributed to the agonist activity of Fingolimod at an S1P3 receptor, an S1P4 receptor, an S1P5 receptor, and the like other than an S1P1 receptor. Therefore, the development of S1P1 receptor-selective compounds has been desired.

It is known that there are oxadiazole derivatives (Patent Document 1, Patent Document 2, Non-Patent Document 5), thiadiazole derivatives, thiazole derivatives (Patent Document 3) and the like having an agonist activity at a S1P1 (EDG-1) receptor. Although the selectivities of all of them to a S1P1 receptor and a S1P3 receptor have been described, there is no report on their selectivities for a S1P4 receptor or a S1P5 receptor except disclosing only their measurement procedures. Moreover, there is no report disclosing a compound having two phenyl groups at the position 2 and 5 of a thiazole ring respectively wherein the phenyl group at the 2-position is coupled with a cyclic amino group via an alkyl group.

PRIOR ART DOCUMENTS

Patent Document

Patent Document 1: WO2003/105771
Patent Document 2: WO2010/43000
Patent Document 3: WO2011/134280

Non-Patent Document

Non-Patent Document 1: Science, 296, 346-349 (2002)
Non-Patent Document 2: Journal of the American Society of Nephrology, 13(4), 1073-1083 (2002)
Non-Patent Document 3: Journal of Biological Chemistry, 279(14), 13839-13848 (2004)
Non-Patent Document 4: Molecular Pharmacology, 58, 449-454 (2000)
Non-Patent Document 5: Journal of Medicinal Chemistry, 48, 6169-6173 (2005)

SUMMARY OF THE INVENTION

The inventors have found a novel compound having a chemical structural feature in comprising a phenyl group coupled with a cyclic amino group via an alkyl group at 2 position of the thiazole ring and a phenyl group at 5 position thereof. Specifically, a compound represented by formula (I):

[Compound 1]

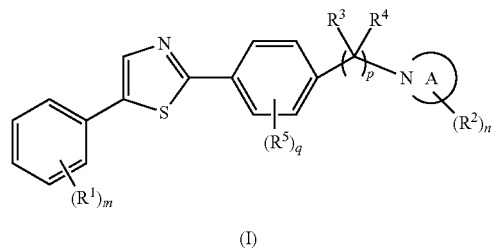

(I)

wherein
A represents a 4- to 7-membered cyclic amine;
m represents an integer of 0 to 5;
n represents an integer of 1 to 3;
p represents an integer of 1 to 3;
q represents an integer of 0 to 4;
$R_1$ represents $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano (when m is 2 or more, $R^1$ may be each independently identical or different);
$R^2$ represents COOH, COOR$^6$, CONR$^7$R$^8$, or tetrazolyl (when n is 2 or more, $R^2$ may be each independently identical or different);
$R^3$ represents a hydrogen atom or $C_{1-6}$ alkyl;
$R^4$ represents a hydrogen atom or $C_{1-6}$ alkyl; or $R^3$ and $R^4$ may together form an oxo group (when p is 2 or more, $R^3$ and $R^4$ may be each independently identical or different);
$R^5$ represents $C_{1-6}$ alkyl, $C_{1-6}$ alkoxy, a halogen atom, halogeno $C_{1-3}$ alkyl, cyano, hydroxyl, or amino (when q is 2 or more, $R^5$ may be each independently identical or different);
$R^6$ represents $C_{1-10}$ alkyl; and
$R^7$ and $R^8$ each independently represent a hydrogen atom or $C_{1-10}$ alkyl,
or a pharmaceutically acceptable salt thereof.

Unexpectedly, the inventors have further found that the compound according to the present invention has selectivity for an S1P1 receptor. Furthermore, the inventors have found that the compound according to the present invention has an excellent property as an S1P receptor modulator with improved cardiotoxicity that has been a problem to be solved. The present invention is based on these findings mentioned above.

An object of the present invention is to provide a compound which has a novel backbone, exerts potent immunosuppressive activity by selectively acting on an S1P1 receptor with less adverse effects, and can be used for oral administration, or a salt thereof.

According to the present invention, the following invention is provided.

(1) A compound represented by the following formula (I) or a pharmaceutically acceptable salt thereof:

[Compound 2]

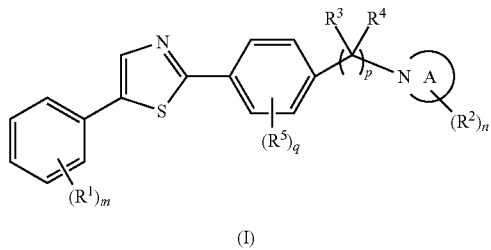

(I)

wherein
A represents a 4- to 7-membered cyclic amine;
m represents an integer of 0 to 5;
n represents an integer of 1 to 3;
p represents an integer of 1 to 3;
q represents an integer of 0 to 4;
$R^1$ represents $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano (when m is 2 or more, $R^1$ may be each independently identical or different);
$R^2$ represents COOH, COOR$^6$, CONR$^7$R$^8$, or tetrazolyl (when n is 2 or more, $R^2$ may be each independently identical or different);
$R^3$ represents a hydrogen atom or $C_{1-6}$ alkyl;
$R^4$ represents a hydrogen atom or $C_{1-6}$ alkyl;
or $R^3$ and $R^4$ may together form an oxo group (when p is 2 or more, $R^3$ and $R^4$ may be each independently identical or different);
$R^5$ represents $C_{1-6}$ alkyl, $C_{1-6}$ alkoxy, a halogen atom, halogeno $C_{1-3}$ alkyl, cyano, hydroxyl, or amino (when q is 2 or more, $R^5$ may be each independently identical or different);
$R^6$ represents $C_{1-10}$ alkyl; and
$R^7$ and $R^8$ each independently represent a hydrogen atom or $C_{1-10}$ alkyl.

(2) The compound according to (1), or a pharmaceutically acceptable salt thereof, wherein n is 1 and p is 1.

(3) The compound according to (1) or pharmaceutically acceptable salts thereof,
wherein
A represents a cyclic amine having a 4- to 6-membered ring;
m represents an integer of 0 to 2;
n represents an integer of 1;
p represents an integer of 1;
q represents an integer of 0 to 1,
$R^1$ represents $C_{1-6}$ alkyl, $C_{1-6}$ alkoxy, phenoxy, benzyloxy, a halogen atom, halogeno $C_{1-3}$ alkyl, or cyano (when m is 2, $R^1$ may be each independently identical or different);
$R^2$ represents COOH, COOR$^6$, CONR$^7$R$^8$, or tetrazolyl;
$R^3$ represents a hydrogen atom or methyl;
$R^4$ represents a hydrogen atom or methyl;
$R^5$ represents $C_{1-6}$ alkyl, $C_{1-6}$ alkoxy, halogen, or halogeno $C_{1-3}$ alkyl;
$R^6$ represents $C_{1-6}$ alkyl; and
$R^7$ and $R^8$ each independently represent a hydrogen atom or methyl.

(4) The compound according to any one of (1) to (3) or a pharmaceutically acceptable salt thereof, wherein $R^2$ represents COOH.

(5) A pharmaceutical composition comprising, as an active ingredient, the compound according to any one of (1) to (4); or a pharmaceutically acceptable salt thereof.

(6) The pharmaceutical composition according to (5), which is used for preventing and/or treating clinical conditions mediated by an S1P1 receptor.

(7) The pharmaceutical composition according to (6), wherein the clinical condition mediated by an S1P1 receptor is selected from the group consisting of transplant rejection, autoimmune diseases and allergic diseases.

(8) The pharmaceutical composition according to (5), which is an S1P1 receptor agonist.

(9) The pharmaceutical composition according to (5), which is an immunosuppressant.

(10) An S1P1 receptor agonist comprising, as an active ingredient, the compound according to any one of (1) to (4) or a pharmaceutically acceptable salt thereof.

(11) A method for treating and/or preventing clinical conditions mediated by an S1P1 receptor, comprising administering a prophylactically or therapeutically safe and effective amount of the compound according to any one of (1) to (4) or a pharmaceutically acceptable salt thereof to mammals including human.

(12) The method according to the method (11), wherein the clinical condition mediated by an S1P1 receptor is selected from the group consisting of transplant rejection, autoimmune diseases, and allergic diseases.

(13) Use of the compound according to any one of (1) to (4) or a pharmaceutically acceptable salt thereof in the manufacture of a medicament for treating and/or preventing clinical conditions mediated by an S1P1 receptor.

(14) The use according to (13), wherein the clinical condition mediated by an S1P1 receptor is selected from the group consisting of transplant rejection, autoimmune diseases, and allergic diseases.

The compound of the present invention of formula (I) is an S1P receptor modulator showing excellent selectivity for an S1P1 receptor. Thus, it is advantageous in providing a pharmaceutical agent for treating and/or preventing clinical conditions mediated by an S1P1 receptor, in particular, transplant rejection, autoimmune diseases or allergic diseases, comprising low probabilities to elicit bradycardia, heart failure, and other adverse effects. Also the compound of the present invention according to formula (I) is advantageous due to its high stability for oral administration.

DETAILED DESCRIPTION OF THE INVENTION

Definition

In the present description, the term "$C_{1-10}$ alkyl" refers to an alkyl group having 1 to 10 carbon atoms and may be linear, branched, or cyclic. And examples include methyl, ethyl, n-propyl, isopropyl, n-butyl, isobutyl, sec-butyl, t-butyl, n-pentyl, n-hexyl, n-heptyl, n-octyl, n-nonyl, n-decyl, cyclopropyl, cyclobutyl, cyclopentyl, cyclohexyl, cycloheptyl, cyclooctyl, cyclononyl, cyclodecyl, and the like.

$C_{1-8}$ alkyl is preferable and examples include methyl, ethyl, n-propyl, isopropyl, n-butyl, isobutyl, t-butyl, n-pentyl, n-hexyl, n-heptyl, n-octyl, cyclopropyl, cyclobutyl, cyclopentyl, cyclohexyl, cycloheptyl, cyclooctyl, and the like.

The term "$C_{1-10}$ alkoxy" refers to an alkoxy group having 1 to 10 carbon atoms, and may be linear, branched, or cyclic. And examples include methoxy, ethoxy, n-propyloxy, isopropyloxy, n-butyloxy, isobutyloxy, sec-butyloxy, t-butyloxy, n-pentyloxy, n-hexyloxy, n-heptyloxy, n-octyloxy, n-nonyloxy, n-decyloxy, cyclopropyloxy, cyclobutyloxy, cyclopentyloxy, cyclohexyloxy, cycloheptyloxy, cyclooctyloxy, cyclononyloxy, cyclodecyloxy, and the like.

$C_{1-8}$ alkoxy is preferable and examples include methoxy, ethoxy, n-propyloxy, isopropyloxy, n-butyloxy, isobutyloxy, t-butyloxy, n-pentyloxy, n-hexyloxy, n-heptyloxy, n-octyloxy, cyclopropyloxy, cyclobutyloxy, cyclopentyloxy, cyclohexyloxy, cycloheptyloxy, cyclooctyloxy, and the like.

The term "phenyl $C_{1-3}$ alkyloxy" refers to $C_{1-3}$ alkyloxy having a phenyl group as a substituent.

Example includes a benzyloxy group, a phenethyloxy group, and the like.

The term "halogen atom" refers to a fluorine atom, a chlorine atom, a bromine atom, or an iodine atom.

The term of "halogeno $C_{1-3}$ alkyl" refers to $C_{1-3}$ alkyl having a halogen atom as a substituent. The number of halogens may be 1 or 2 or more. When the number of halogens is 2 or more, each halogen atom may be identical or different.

For example, a chloromethyl group, a fluoromethyl group, a difluoromethyl group, a trifluoromethyl group, a 2-chloroethyl group, a 2-fluoroethyl group, a 2,2-difluoroethyl group, a 2,2,2-trifluoroethyl group, a 1,1,2,2-tetrafluoroethyl group, a pentafluoroethyl group, and the like are enumerated.

The term "a 4-membered to 7-membered cyclic amine" refers to a saturated cyclic amine having a 4- to 7-membered ring. Azetidine is an example of a 4-membered cyclic amine, pyrrolidine is an example of a 5-membered cyclic amine, piperidine is an example of a 6-membered cyclic amine, azepane is an example of a 7-membered cyclic amine, and the like.

The term "pharmaceutically acceptable salt" refers to a salt that is formed by the reaction between the compound in the present invention, and an acid or base.

Salts, for example, include hydrohalide salts such as hydrofluoride, hydrochloride, hydrobromide, hydriodide, and the like; inorganic acid salts such as nitrate, perchlorate, sulfate, phosphate, and the like; lower alkane sulfonates such as methanesulfonate, trifluoromethanesulfonate, ethanesulfonate, and the like; aryl sulfonates such as benzenesulfonate, p-toluenesulfonate, and the like; organic acid salts such as acetate, malate, fumarate, succinate, citrate, ascorbate, tartrate, oxalate, maleate, and the like; alkali metal salts such as a sodium salt, a potassium salt, a lithium salt, and the like; salts of alkali earth metals such as a calcium salt, a magnesium salt, and the like; metal salts such as an aluminium salt, an iron salt, and the like; inorganic salts such as an ammonium salt, and the like; organic amine salts such as a t-octylamine salt, a dibenzylamine salt, a morpholine salt, a glucosamine salt, a phenyl glycine alkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzylphenethylamine salt, a piperazine salt, a tetramethylammonium salt, a tris(hydroxymethyl)aminomethane salt, and the like; amino acid salts such as a glycine salt, a lysine salt, an arginine salt, an ornithine salt, a glutamic acid salt, an aspartic acid salt, and the like.

Preferably, examples include hydrochloride, hydrobromide, nitrate, sulfate, phosphate, methanesulfonate, benzenesulfonate, p-toluenesulfonate, acetate, malate, fumarate, succinate, citrate, ascorbate, tartrate, oxalate, maleate, a sodium salt, a potassium salt, a calcium salt, a magnesium salt, an ammonium salt, a glycine salt, a lysine salt, an arginine salt, an ornithine salt, a glutamic acid salt, an aspartic acid salt, and the like.

Compound of Formula (I)

In formula (I), $R^1$ represents, identically or differently, $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano. $C_{1-8}$ alkoxy, $C_{1-8}$ alkyl, phenyl, phenoxy, phenyl $C_{1-3}$ alkyloxy, a halogen atom, halogeno $C_{1-3}$ alkyl, or cyano is preferable. $C_{1-8}$ alkoxy, $C_{1-8}$ alkyl, phenoxy, phenyl $C_{1-3}$ alkyloxy, a halogen atom, halogeno $C_{1-3}$ alkyl, or cyano is more preferable. $C_{1-6}$ alkoxy, $C_{1-6}$ alkyl, phenoxy, benzyloxy, a halogen atom, halogeno $C_{1-3}$ alkyl, or cyano is more preferable. $C_{1-6}$ alkoxy, $C_{1-6}$ alkyl, phenoxy, benzyloxy, cyano, $C_{1-3}$ alkyl fluoride, fluorine atom, or a chlorine atom is further preferable. In particular, isopropyloxy or a chlorine atom is preferable.

In formula (I), $R^2$ represents, identically or differently, COOH, $COOR^6$, $CONR^7R^8$, or tetrazolyl. COOH or tetrazolyl is preferable and COOH is more preferable.

In formula (I), $R^3$ represents a hydrogen atom, $C_{1-6}$ alkyl, preferably a hydrogen atom or $C_{1-3}$ alkyl, more preferably methyl or a hydrogen atom.

In formula (I), $R^4$ represents a hydrogen atom, $C_{1-6}$ alkyl, preferably a hydrogen atom or $C_{1-3}$ alkyl. Methyl or a hydrogen atom is more preferable.

In formula (I), $R^5$ represents, identically or differently, $C_{1-6}$ alkyl, $C_{1-6}$ alkoxy, a halogen atom, halogeno $C_{1-3}$ alkyl, cyano, a hydroxyl group, or an amino group. $C_{1-6}$ alkyl, $C_{1-6}$ alkoxy, a halogen atom, or halogeno $C_{1-3}$ alkyl is preferable. $C_{1-4}$ alkyl, $C_{1-3}$ alkoxy, a halogen atom, or halogeno $C_{1-3}$ alkyl is more preferable. $C_{1-4}$ alkyl, $C_{1-3}$ alkoxy, a fluorine atom, a chlorine atom, or $C_{1-3}$ alkyl fluoride is further preferable. $C_{1-3}$ alkyl or fluorine atom is most preferable.

In formula (I), $R^6$ represents $C_{1-10}$ alkyl. $C_{1-6}$ alkyl is preferable and $C_{1-4}$ alkyl is further preferable, methyl is more preferable.

In formula (I), $R^7$ and $R^8$ each independently represent a hydrogen atom or $C_{1-10}$ alkyl. A hydrogen atom or $C_{1-6}$ alkyl is preferable, a hydrogen atom or $C_{1-4}$ alkyl is further preferable, a hydrogen atom or methyl is more preferable.

A is a 4-membered to a 7-membered cyclic amine, preferably a 4-membered to a 6-membered cyclic amine, further preferably a 4-membered cyclic amine.

In formula (I), m represents an integer of 0 to 5, preferably 0 to 3, further preferably 0 to 2.

In formula (I), n represents an integer of 1 to 3, preferably 1 to 2, further preferably 1.

In formula (I), p represents an integer of 1 to 3, preferably 1 to 2, further preferably 1.

In formula (I), q represents an integer of 0 to 4, preferably 0 to 2, further preferably 0 to 1.

As a preferable combination of each substituent in formula (I), $R^1$ is $C_{1-10}$ alkoxy, $C_{1-10}$ alkyl, phenyl, phenoxy, a halogen atom, cyano, or halogeno $C_{1-3}$ alkyl; $R^2$ is COOH, COOR$^6$, CONR$^7$R$^8$ or tetrazolyl; $R^3$ is a hydrogen atom or $C_{1-6}$ alkyl; $R^4$ is a hydrogen atom or $C_{1-6}$ alkyl; $R^5$ is $C_{1-6}$ alkyl, $C_{1-6}$ alkoxy, a halogen atom, halogeno $C_{1-3}$ alkyl, cyano, a hydroxyl group, or an amino group; $R^6$ is $C_{1-10}$ alkyl; $R^7$, $R^8$ are each independently a hydrogen atom or $C_{1-10}$ alkyl; A is a 4-membered to 7-membered cyclic amine; m is an integer of 1 to 5; n is an integer of 1 to 3; p is an integer of 1 to 3; and q is an integer of 0 to 4.

As a further preferable combination of each substituent in formula (I), $R^1$ is $C_{1-8}$ alkoxy, $C_{1-8}$ alkyl, phenyl, phenoxy, a halogen atom, cyano, or halogeno $C_{1-3}$ alkyl; $R^2$ is COOH or tetrazolyl; $R^3$ is a hydrogen atom or $C_{1-3}$ alkyl; $R^4$ is a hydrogen atom or $C_{1-3}$ alkyl; $R^5$ is $C_{1-6}$ alkyl, a halogen atom, or halogeno $C_{1-3}$ alkyl, $R^6$ is $C_{1-6}$ alkyl; $R^7$ and $R^8$ are each independently a hydrogen atom or $C_{1-6}$ alkyl; A is a 4-membered to 6-membered cyclic amine; m is an integer of 1 to 3; n is an integer of 1 to 3; p is an integer 1 to 2; and q is an integer 0 to 2.

As a more preferable combination of each substituent in formula (I), $R^1$ is $C_{2-8}$ alkoxy, $C_{2-8}$ alkyl, cyano, $C_{1-3}$ alkyl fluoride or a halogen atom; $R^2$ is COOH or tetrazolyl; $R^3$ is a hydrogen atom or $C_{1-3}$ alkyl; $R^4$ is a hydrogen atom or $C_{1-3}$ alkyl; $R^5$ is $C_{1-3}$ alkyl, a fluorine atom, or $C_{1-3}$ alkyl fluoride; A is a 4-membered to 6-membered cyclic amine; m is 1 to 3; n is 1 to 3; p is 1 or 2; and q is 0 to 2.

As most preferable combination of each substituent in formula (I), $R^1$ is isopropyloxy or a chlorine atom; $R^2$ is COOH; $R^3$ is methyl or a hydrogen atom; $R^4$ is methyl or a hydrogen atom; $R^5$ is $C_{1-3}$ alkyl or a fluorine atom; A is a 4-membered cyclic amine; m is 1 to 2; n is 1; p is 1; and q is 0 to 1.

A preferable aspect in the present invention is the compound of formula (I), wherein $R^1$ is $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano (when m is 2 or more, $R^1$ may be each independently identical or different); $R^2$ is COOH, COOR$^6$, CONR$^7$R$^8$, or tetrazolyl (when n is 2 or more, $R^2$ is each independently identical or different); $R^3$ is a hydrogen atom or $C_{1-6}$ alkyl; $R^4$ is a hydrogen atom or $C_{1-6}$ alkyl; $R^5$ is $C_{1-6}$ alkyl, $C_{1-6}$ alkoxy, a halogen atom, or halogeno $C_{1-3}$ alkyl; $R^6$ is $C_{1-10}$ alkyl; $R^7$ and $R^8$ are each independently a hydrogen atom or $C_{1-10}$ alkyl; A is a 4- to 7-membered cyclic amine; m is 0 to 5; n is 1 to 3; p is 1 to 3; and q is 0 to 4.

A more preferable aspect in the present invention is the compound of formula (I), wherein $R^1$ is $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano (when m is 2, $R^1$ may be each independently identical or different); $R^2$ is COOH, COOR$^6$, CONR$^7$R$^8$, or tetrazolyl; $R^3$ is a hydrogen atom or $C_{1-6}$ alkyl; $R^4$ is a hydrogen atom or $C_{1-6}$ alkyl; $R^5$ is $C_{1-6}$ alkyl, $C_{1-6}$ alkoxy, a halogen atom, or halogeno $C_{1-3}$ alkyl; $R^6$ is $C_{1-10}$ alkyl; $R^7$ and $R^8$ are each independently a hydrogen atom or $C_{1-10}$ alkyl; A is a 4- to 7-membered cyclic amine; m is an integer of 0 to 2; n is an integer of 1; p is an integer of 1; and q is an integer of 0 to 1.

A further preferable aspect in the present invention is the compound of formula (I), wherein $R^1$ is $C_{1-6}$ alkoxy, $C_{1-6}$ alkyl, phenoxy, benzyloxy, a halogen atom, halogeno $C_{1-3}$ alkyl, or cyano (when m is 2, $R^1$ may be each independently identical or different); $R^2$ is COOH, COOR$^6$, CONR$^7$R$^8$, or tetrazolyl; $R^3$ is a hydrogen atom or $C_{1-3}$ alkyl; $R^4$ a hydrogen atom or $C_{1-3}$ alkyl; $R^5$ is $C_{1-6}$ alkyl, $C_{1-6}$ alkoxy, a halogen atom, or halogeno $C_{1-3}$ alkyl; $R^6$ is $C_{1-6}$ alkyl; $R^7$ and $R^8$ are each independently a hydrogen atom or $C_{1-4}$ alkyl; A is a 4- to 7-membered cyclic amine; m is 0 to 2; n is 1; p is 1; and q is 0 to 1.

A further preferable aspect in the present invention is the compound of formula (I), wherein $R^1$ is $C_{1-6}$ alkoxy, $C_{1-6}$ alkyl, phenoxy, benzyloxy, a halogen atom, halogeno $C_{1-3}$ alkyl, or cyano (when m is 2, $R^1$ may be each independently identical or different); $R^2$ is COOH, COOR$^6$, CONR$^7$R$^8$, or tetrazolyl; $R^3$ is a hydrogen atom or methyl; $R^4$ is a hydrogen atom or methyl; $R^5$ is $C_{1-6}$ alkyl, $C_{1-6}$ alkoxy, a halogen atom, or halogeno $C_{1-3}$ alkyl; $R^6$ is $C_{1-6}$ alkyl; $R^7$ and $R^8$ are each independently a hydrogen atom or methyl; A is a 4- to 6-membered cyclic amine; m is 0 to 2; n is 1; p is 1; and q is 0 to 1.

A particularly preferable aspect in the present invention is the compound of formula (I), wherein $R^1$ is $C_{1-6}$ alkoxy, $C_{1-6}$ alkyl, phenoxy, benzyloxy, a fluorine atom, a chlorine atom, $C_{1-3}$ alkyl fluoride, or cyano (when m is 2, $R^1$ may be each independently identical or different); $R^2$ is COOH, COOR$^6$, CONR$^7$R$^8$, or tetrazolyl; $R^3$ is a hydrogen atom or methyl; $R^4$ is a hydrogen atom or methyl; $R^5$ is $C_{1-4}$ alkyl, $C_{1-3}$ alkoxy, a fluorine atom, a chlorine atom, or $C_{1-3}$ alkyl fluoride; $R^6$ is $C_{1-6}$ alkyl; $R^7$ and $R^8$ are each independently a hydrogen atom or methyl; A is a 4- to 6-membered cyclic amine; m is 0 to 2; n is 1; p is 1; and q is 0 to 1.

The most preferable aspect in the present invention is the compound of formula (I), wherein $R^1$ is $C_{1-6}$ alkoxy, $C_{1-6}$ alkyl, a fluorine atom, a chlorine atom, $C_{1-3}$ alkyl fluoride, or cyano (when m is 2, $R^1$ may be each independently identical or different); $R^2$ is COOH; $R^3$ is a hydrogen atom or methyl; $R^4$ is a hydrogen atom or methyl; $R^5$ is $C_{1-4}$ alkyl, $C_{1-3}$ alkoxy, a fluorine atom, a chlorine atom, or $C_{1-3}$ alkyl fluoride; A is a 4-membered cyclic amine; m is 1 to 2; n is 1; p is 1; and q is 0 to 1.

A specific compound group of the compound of formula (I) is enumerated as follows:

methyl 1-(4-(5-(4-isopropoxyphenyl)thiazol-2-yl)benzyl)azetidine-3-carboxylate 1-(4-(5-(4-isopropoxyphenyl)thiazol-2-yl)benzyl)azetidine-3-carboxylic acid 1-(4-(5-(3-chloro-4-isopropoxyphenyl)thiazol-2-yl)benzyl)azetidine-3-carboxylic acid 2-(4-((3-(2H-tetrazol-5-yl)azetidin-1-yl)methyl)phenyl)-5-(4-isopropoxyphenyl)thiazole 1-(4-(5-(4-isopropoxyphenyl)thiazol-2-yl)benzyl)piperidine-4-carboxylic acid 1-(4-(5-phenylthiazol-2-yl)benzyl)azetidine-3-carboxylic acid 1-(4-(5-(3-isopropoxyphenyl)thiazol-2-yl)benzyl)azetidine-3-carboxylic acid
1-(1-(4-(5-(4-isopropoxyphenyl)thiazol-2-yl)phenyl)ethyl)azetidine-3-carboxylic acid
(S)-1-(4-(5-(4-isopropoxyphenyl)thiazol-2-yl)benzyl)pyrrolidine-2-carboxylic acid
1-(4-(5-(4-isopropoxyphenyl)thiazol-2-yl)benzyl)piperidine-3-carboxylic acid
1-(4-(5-(3-chloro-4-isopropoxyphenyl)thiazol-2-yl)-3-fluorobenzyl)azetidine-3-carboxylic acid
1-(3-chloro-4-(5-(4-isopropoxyphenyl)thiazol-2-yl)benzyl)azetidine-3-carboxylic acid
1-(3-butyl-4-(5-(4-isopropoxyphenyl)thiazol-2-yl)benzyl)azetidine-3-carboxylic acid
1-(3-cyclopropyl-4-(5-(4-isopropoxyphenyl)thiazol-2-yl)benzyl)azetidine-3-carboxylic acid
1-(3-ethyl-4-(5-(4-isopropoxyphenyl)thiazol-2-yl)benzyl)azetidine-3-carboxylic acid
1-(4-(5-(4-cyclopropoxyphenyl)thiazol-2-yl)benzyl)azetidine-3-carboxylic acid
1-(3-fluoro-4-(5-(4-isopropoxyphenyl)thiazol-2-yl)benzyl)azetidine-3-carboxylic acid
1-(4-(5-(4-isopropoxyphenyl)thiazol-2-yl)-3-methoxybenzyl)azetidine-3-carboxylic acid
1-(2-butyl-4-(5-(4-isopropoxyphenyl)thiazol-2-yl)benzyl)azetidine-3-carboxylic acid
1-(2-ethyl-4-(5-(4-isopropoxyphenyl)thiazol-2-yl)benzyl)azetidine-3-carboxylic acid
1-(4-(5-(4-isopropoxyphenyl)thiazol-2-yl)-3-methylbenzyl)azetidine-3-carboxylic acid
1-(2-fluoro-4-(5-(4-isopropoxyphenyl)thiazol-2-yl)benzyl)azetidine-3-carboxylic acid
1-(2-chloro-4-(5-(4-isopropoxyphenyl)thiazol-2-yl)benzyl)azetidine-3-carboxylic acid
1-(2-cyclopropyl-4-(5-(4-isopropoxyphenyl)thiazol-2-yl)benzyl)azetidine-3-carboxylic acid
1-(4-(5-(4-isopropoxyphenyl)thiazol-2-yl)-2-methylbenzyl)azetidine-3-carboxylic acid
1-(4-(5-(4-isopropoxyphenyl)thiazol-2-yl)-2-methoxy benzyl)azetidine-3-carboxylic acid
1-(4-(5-(4-isopropoxyphenyl)thiazol-2-yl)-2-(trifluoromethyl)benzyl)azetidine-3-carboxylic acid
1-(4-(5-(4-isopropoxyphenyl)thiazol-2-yl)benzyl)azetidine-3-carboxamide
1-(4-(5-(4-isopropoxyphenyl)thiazol-2-yl)benzyl)-N-methylazetidine-3-carboxamide
1-(4-(5-(4-isopropoxyphenyl)thiazol-2-yl)benzyl)-N,N-dimethylazetidine-3-carboxamide
1-(4-(5-(4-ethoxyphenyl)thiazol-2-yl)benzyl)azetidine-3-carboxylic acid
1-(4-(5-(4-phenoxyphenyl)thiazol-2-yl)benzyl)azetidine-3-carboxylic acid
1-(4-(5-(4-tert-butylphenyl)thiazol-2-yl)benzyl)azetidine-3-carboxylic acid
1-(4-(5-(4-cyclopentylphenyl)thiazol-2-yl)benzyl)azetidine-3-carboxylic acid
1-(4-(5-(4-hexylphenyl)thiazol-2-yl)benzyl)azetidine-3-carboxylic acid
1-(4-(5-(4-cyclohexylphenyl)thiazol-2-yl)benzyl)azetidine-3-carboxylic acid
1-(4-(5-(3-chloro-4-isopropoxyphenyl)thiazol-2-yl)-3-methylbenzyl)azetidine-3-carboxylic acid
1-(4-(5-(4-propoxyphenyl)thiazol-2-yl)benzyl)azetidine-3-carboxylic acid
1-(4-(5-(4-butoxyphenyl)thiazol-2-yl)benzyl)azetidine-3-carboxylic acid
1-(4-(5-(4-pentyloxyphenyl)thiazol-2-yl)benzyl)azetidine-3-carboxylic acid
1-(4-(5-(4-(cyclopentyloxy)phenyl)thiazol-2-yl)benzyl)azetidine-3-carboxylic acid
1-(4-(5-(4-hexyloxyphenyl)thiazol-2-yl)benzyl)azetidine-3-carboxylic acid
1-(4-(5-(4-(cyclohexyloxy)phenyl)thiazol-2-yl)benzyl)azetidine-3-carboxylic acid
1-(4-(5-(4-benzyloxyphenyl)thiazol-2-yl)benzyl)azetidine-3-carboxylic acid
1-(4-(5-(4-propylphenyl)thiazol-2-yl)benzyl)azetidine-3-carboxylic acid
1-(4-(5-(4-isopropylphenyl)thiazol-2-yl)benzyl)azetidine-3-carboxylic acid
1-(4-(5-(4-butylphenyl)thiazol-2-yl)benzyl)azetidine-3-carboxylic acid
1-(4-(5-(4-isobutylphenyl)thiazol-2-yl)benzyl)azetidine-3-carboxylic acid
1-(4-(5-(4-pentylphenyl)thiazol-2-yl)benzyl)azetidine-3-carboxylic acid
1-(4-(5-(3-cyano-4-isopropoxyphenyl)thiazol-2-yl)benzyl)azetidine-3-carboxylic acid
1-(4-(5-(4-cyclobutoxyphenyl)thiazol-2-yl)benzyl)azetidine-3-carboxylic acid
1-(4-(5-(4-isopropoxy-3-methylphenyl)thiazol-2-yl)benzyl)azetidine-3-carboxylic acid
1-(4-(5-(3-fluoro-4-isopropoxyphenyl)thiazol-2-yl)benzyl)azetidine-3-carboxylic acid
1-(4-(5-(4-isopropoxy-2-methylphenyl)thiazol-2-yl)benzyl)azetidine-3-carboxylic acid
1-(4-(5-(4-isopropoxy-2-(trifluoromethyl)phenyl)thiazol-2-yl)benzyl)azetidine-3-carboxylic acid
1-(4-(5-(4-isopropoxy-3-(trifluoromethyl)phenyl)thiazol-2-yl)benzyl)azetidine-3-carboxylic acid
1-(4-(5-(3-chloro-4-isopropoxyphenyl)thiazol-2-yl)-2-fluorobenzyl)azetidine-3-carboxylic acid
1-(4-(5-(3-chloro-4-isopropoxyphenyl)thiazol-2-yl)-2-(trifluoromethyl)benzyl)azetidine-3-carboxylic acid
1-(4-(5-(3-cyano-4-isobutylphenyl)thiazol-2-yl)-3-fluoro benzyl)azetidine-3-carboxylic acid
1-(3-chloro-4-(5-(3-chloro-4-isopropoxyphenyl)thiazol-2-yl)benzyl)azetidine-3-carboxylic acid
1-(4-(5-(3-chloro-4-isopropoxyphenyl)thiazol-2-yl)-3-methoxybenzyl)azetidine-3-carboxylic acid
1-(4-(5-(3-chloro-4-isopropoxyphenyl)thiazol-2-yl)-2-methylbenzyl)azetidine-3-carboxylic acid
1-(2-chloro-4-(5-(3-chloro-4-isopropoxyphenyl)thiazol-2-yl)benzyl)azetidine-3-carboxylic acid
1-(4-(5-(3-chloro-4-isopropoxyphenyl)thiazol-2-yl)-2-methoxybenzyl)azetidine-3-carboxylic acid
1-(4-(5-(4-isopropoxyphenyl)thiazol-2-yl)benzyl)azetidine-3-carboxylic acid hydrochloride
1-(4-(5-(4-isopropoxyphenyl)thiazol-2-yl)benzyl)azetidine-3-carboxylic acid sulfate
1-(4-(5-(4-isopropoxyphenyl)thiazol-2-yl)benzyl)azetidine-3-carboxylic acid methanesulfonate
1-(4-(5-(4-isopropoxyphenyl)thiazol-2-yl)benzyl)azetidine-3-carboxylic acid acetate
1-(4-(5-(4-isopropoxyphenyl)thiazol-2-yl)benzyl)azetidine-3-carboxylic acid sodium salt Since the compound in the present invention represented by formula (I), in some cases, has an asymmetric carbon atom within its molecule, optical isomers thereof exist. These isomers and the mixture thereof are represented by a single formula, i.e., formula (I). Therefore, the compound in the present invention represented by formula (I) includes all the optical isomers and the mixture thereof in arbitrary proportion.

Moreover, the compound in the present invention represented by formula (I), in some cases, forms tautomer depending on the conditions including the form of salts thereof, pH, and the like. The present invention comprises these tautomers and the mixture thereof in arbitrary proportion.

deprotection can be referred to the above-mentioned book and the like.

The compound of formula (I) can be produced by methods (A~D) hereinafter described or equivalent methods to these, and the procedure of deprotection can be involved when needed. For example, when the desired substituent is incompatible with the reaction conditions used, the substituent can be introduced as a protected group at the beginning and deprotected after the completion of the reaction.

Production Method 1

[Compound 3]

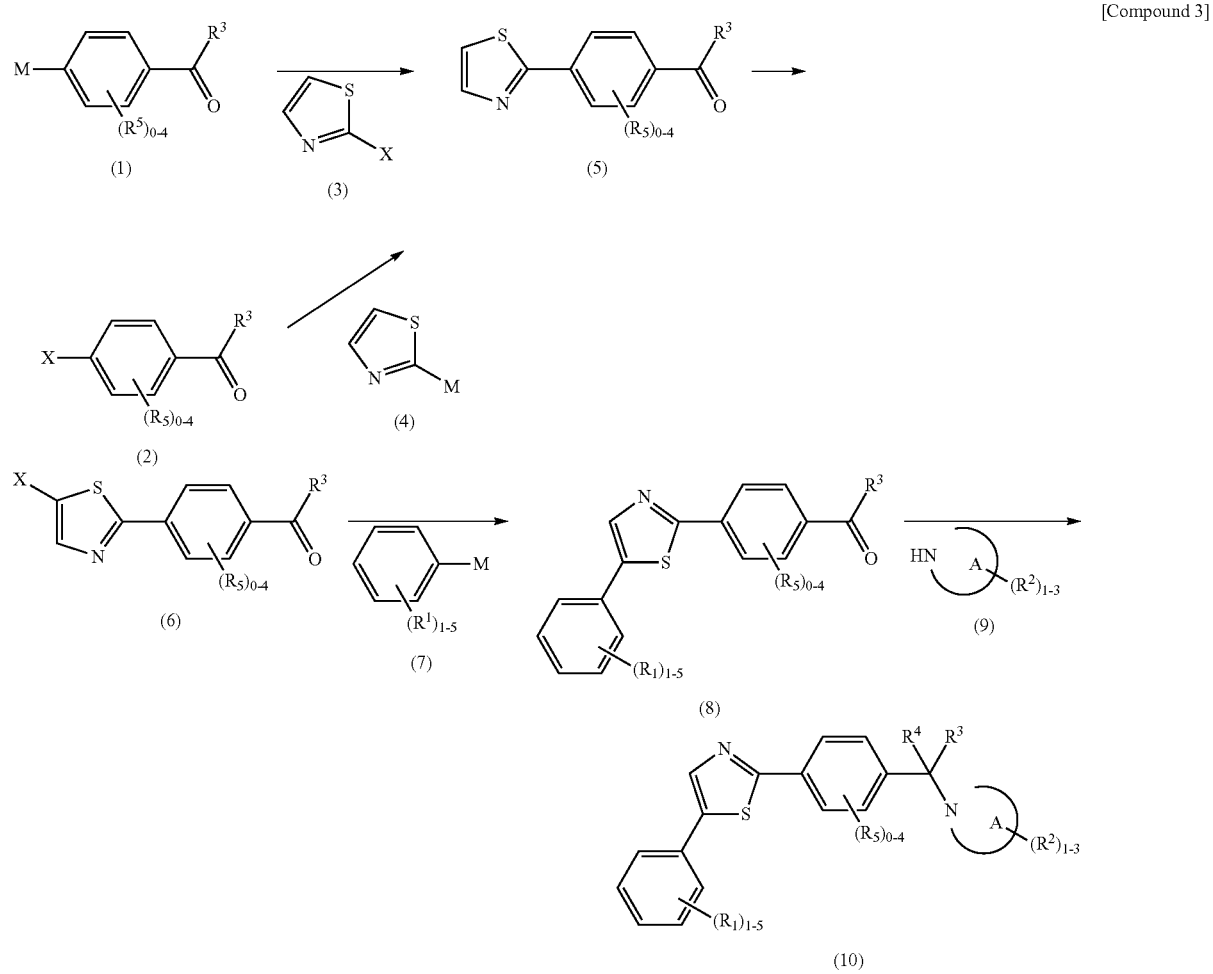

The compound in the present invention represented by formula (I) may be used as a prodrug. A prodrug is preferred for oral administration since it is able to be hydrolyzed in vivo, being well absorbed from the membrane of the stomach or intestine, and being tolerant to degradation by gastric acid, and other elements.

Production Method of Compound of Formula (I)

The compound in the present invention can be produced, for example, by methods hereinafter described or equivalent methods to these.

In what follows, substituents may be "protected" when needed. The "protecting group" can be referred to a book entitled "Protective Groups in Organic Synthesis" (T. W. Greene et al., Wiley, New York (1999)) and the like, as is well known to those skilled in the art. Moreover, the procedure of wherein, X represents a halogen atom or a leaving group; M represents a functional group including boron, silicon, and a metal atom; and $R^1$, $R^2$, $R^3$, $R^4$, and $R^5$ represent the same as described in general formula (I).

A leaving group is not particularly limited but is preferably a trifluoromethanesulfonyloxy group and a p-toluenesulfonyloxy group.

Examples of M include boron, silicon, a metal atom, and the like.

Examples of metal atoms include a tin atom, a magnesium atom, a zinc atom, a copper atom, and the like, and preferably a tin atom, a zinc atom, and the like.

As X and M preferable one can be chosen in various reactions mentioned above.

In the following Production Method A, the production method of a compound (5) formed by a condensation reaction of the compound (1) and compound (3) shown in the Production Method 1 will be explained.

Production Method A

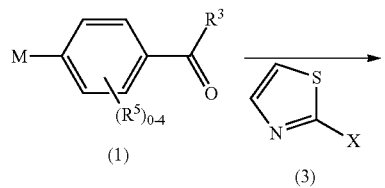

[Compound 4]

wherein, X, $R^3$, and $R^5$ represent the same as described above.

For example, when M of the compound (1) is boronic acid or ester thereof and X of the compound (3) is a bromine atom or an iodine atom, the condensation reaction can be carried out by reacting tetrakis(triphenylphosphine)palladium and a base such as sodium carbonate, and the like. Preferable reaction solvents include, though not in particular limited thereto, a mixed solvent system of a nonpolar solvent (such as toluene and the like)-water, a mixed solvent system of a nonpolar solvent (such as toluene and the like)-alcohol (such as ethanol and the like)-water, or a mixed solvent system of a polar aprotic solvent (such as 1,4-dioxane, N,N-dimethylformamide and the like)-water. The reaction temperature can be set at 0° C. to 200° C., preferably at room temperature to 120° C. The reaction time can be generally set for 0.5 hour to 72 hours.

When M of the compound (1) is other than boronic acid or ester thereof, the condensation reaction can be performed by referring to, for example, a method disclosed by Negishi and et al. (Org. Synth., 66, 67, (1987)).

For the compound (1), a commercially available compound can be used, or the compound (1) can be produced by a halogen-metal exchange reaction of the corresponding halogen compound.

The compound (5) can be produced by the condensation of the compound (2) and compound (4) by the following Production Method A (alternative).

Production Method A (alternative)

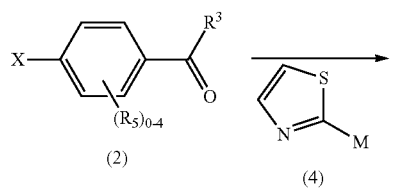

[Compound 5]

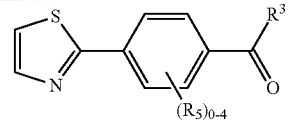

wherein, X, $R^3$, and $R^5$ represent the same meanings as described above.

For example, when M of the compound (4) is a trialkylstannyl group such as those exemplified by a tributylstannyl group, and X of the compound (2) is a bromine atom or an iodine atom, the condensation reaction can be carried out by reacting bis(triphenylphosphine) palladium dichloride and the like. Reaction solvents include, though not in particular limited thereto, a mixed solvent system of a nonpolar solvent (such as toluene and the like)-water, a mixed solvent system of a nonpolar solvent (such as toluene and the like)-alcohol (such as ethanol and the like)-water, or a mixed solvent system of a polar aprotic solvent (such as 1,4-dioxane, N,N-dimethylformamide, and the like)-water are preferable. The reaction temperature can be set at 0° C. to 200° C., preferably at room temperature to 120° C. The reaction time can be generally set for 0.5 hour to 72 hours.

When M of the compound (2) is other than a trialkylstannyl group, a condensation reaction can be performed by referring to, for example, the method disclosed by Negishi and et al. (Org. Synth., 66, 67, (1987)).

For the compound (2), a commercially available compound can be used or the compound (2) can be produced by reagents that are commonly used in the halogenation reaction of aromatic compounds.

A method of producing a compound (6) produced by the halogenation reaction of the compound (5) shown in the Production Method 1 will be explained in the following Production Method B.

Production Method B

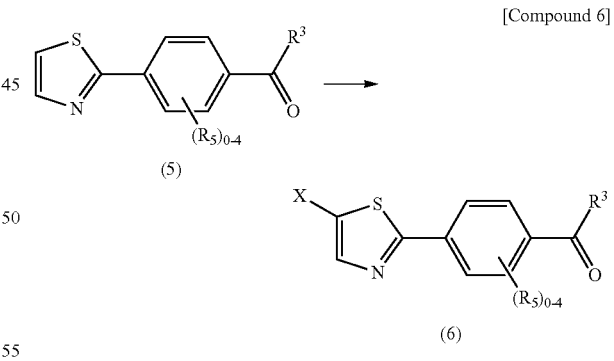

[Compound 6]

wherein, X, and $R^3$, $R^5$ represent the same meanings as described above.

When X of the compound (6) is a bromine atom for example, the stereoselective bromination reaction of compound (5) can be carried out by using a brominating reagent that is commonly used for the bromination reaction of aromatic compounds. Commonly-used brominating reagents include, for example, N-bromosuccinimide (NBS), bromine ($Br_2$), copper (II) bromide, preferably NBS or $Br_2$. Reaction solvents include, for example, halogenated hydrocarbon solvents such as methylene chloride and the like, polar aprotic solvents such as N,N-dimethylformamide and the like, polar protic solvents such as acetic acid and the like. Methylene chloride, chloroform, N,N-dimethylformamide or acetic acid is preferable. The reaction temperature can be set at −50° C. to the boiling point of the solvent, preferably 0° C. to 50° C. The reaction time can be set generally for 1 hour to 72 hours.

When X of the compound (6) is other than a bromine atom, the reaction can be suitably conducted by using known halogenating agents.

In Production Method C, a method of producing a compound (8) by the condensation of the compound (6) and compound (7) described in the Production Method 1 will be explained.

Production Method C

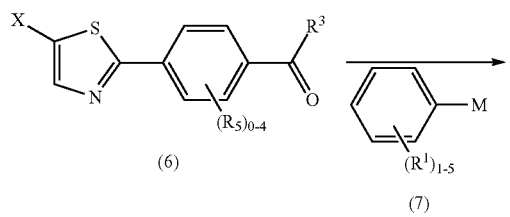

(6)

(7)

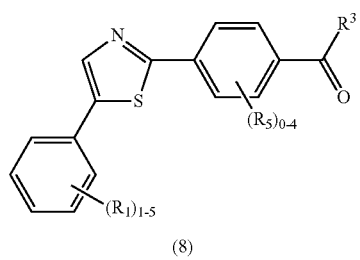

(8)

wherein, X, M, and $R^1$, $R^3$, $R^5$ represent the same meanings as described above.

For example, when X of the compound (6) is a bromine atom or an iodine atom, and M of the compound (7) is boronic acid or ester thereof, the condensation reaction can be conducted by reacting tetrakis(triphenylphosphine)palladium and the like, with bases such as sodium carbonate and the like. Reaction solvents preferably include, though not in particular limited thereto, a mixed solvent system of a nonpolar solvent (such as toluene and the like)-water, a mixed solvent system of a nonpolar solvent (such as toluene and the like)-alcohol (such as ethanol and the like)-water, a mixed solvent system of a polar aprotic solvent (1,4-dioxane, N,N-dimethylformamide, and the like)-water. The reaction temperature can be set at 0° C. to 200° C., preferably at room temperature to 120° C. The reaction time can be generally set for 0.5 hour to 72 hours. When m=0, the product (8) can also be produced according to the Production Method C.

When M of the compound (7) is other than boronic acid or ester thereof, the condensation reaction can be performed by referring to, for example, the method disclosed by Negishi and et al. (Org. Synth., 66, 67, (1987)).

In Production Method D, a method of producing a compound (10) by reacting the compound (8) and compound (9) described in the Production Method 1 will be explained.

Production Method D

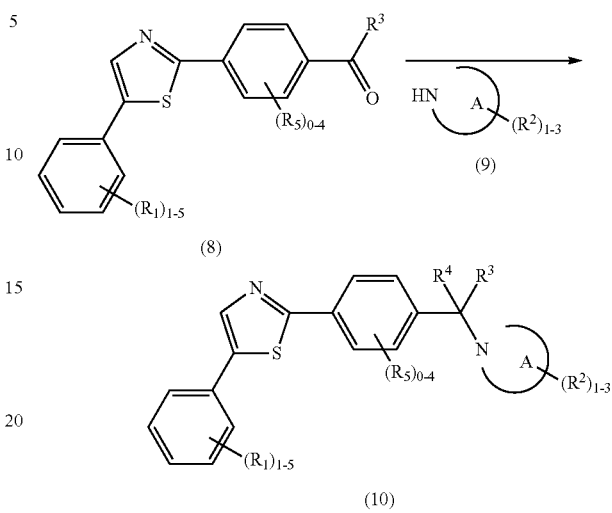

wherein $R^1$, $R^2$, $R^3$, $R^4$, $R^5$ represent the same meanings as described above.

In the compound (10), when $R^4$ is a hydrogen atom, the reaction between the compound (8) and the compound (9) can be conducted by using metal hydride such as sodium borohydride, sodium triacetoxyborohydride, sodium cyanoborohydride, borane complex, and the like, or by catalytic hydrogenation reaction. Reaction solvents preferably include, though not in particular limited thereto, halogenated hydrocarbon solvents such as dichloromethane, chloroform, and the like, polar protic solvents such as methanol, acetic acid, water, and the like, and the mixed solvents thereof. The reaction temperature can be set at −20° C. to the boiling point of the solvent, preferably 0° C. to room temperature. The reaction time can be generally set for 1 hour to 72 hours.

In the compound (10), when $R^4$ is $C_{1-6}$ alkyl, the reaction between the compound (8) and the compound (9) can be conducted by using a Grignard reagent represented by methylmagnesium bromide, an organic lithium reagent represented by methyl lithium, allylsilane, or metal acetylide. Reaction solvents preferably include, though not in particular limited thereto, halogenated hydrocarbon solvents such as dichloromethane, chloroform, and the like, polar aprotic solvents such as diethyl ether, tetrahydrofuran, and the like. The reaction temperature can be set at −78° C. to the boiling point of the solvent, preferably at −20° C. to room temperature. The reaction time can be generally set for 1 hour to 72 hours.

Medicinal Use and Pharmaceutical Composition

As shown in the Examples mentioned below, a compound represented by formula (I) has an agonist action at S1P receptor (in particular, an S1P1 receptor). Therefore, the said compound can be used for treating and/or preventing diseases mediated by an S1P1 receptor. Particularly, since the compound suppresses immunity, it can be used for treating and/or preventing transplant rejection, autoimmune diseases, allergic diseases, and the like.

The transplant rejection includes acute rejection that occurs up to three months after the transplantation of grafts such as a graft of liver, kidney, heart, lung, small intestine, skin, cornea, bone, embryonic tissue, bone-marrow cell, hematopoietic stem cell, peripheral-blood stem cell, umbilical cord blood stem cell, pancreatic islet cell, hepatocyte, neurocyte, and intestinal epithelial cell; chronic transplant rejection that happens after that; and graft-versus-host disease.

Autoimmune diseases include, for example, connective tissue disease, systemic lupus erythematosus, rheumatoid arthritis, multiple sclerosis, nephrotic syndrome, lupus nephritis, Sjogren's syndrome, scleroderma, polymyositis, psoriasis, inflammatory bowel disease, Crohn's disease, mixed connective tissue disease, primary myxedema, Addison's disease, aplastic anemia, autoimmune hemolytic anemia, autoimmune thrombocytopenia, autoimmune diabetes, uveitis, receptor disease, myasthenia gravis, thyrotoxicosis, thyroiditis, Hashimoto's disease, and the like.

Allergic diseases include, for example, atopic dermatitis, asthma, allergic rhinitis, conjunctivitis, and the like.

The term "prevention" in the present description refers to reducing the risk for developing diseases in a subject not yet afflicted by diseases or symptoms, or reducing the risk of recurrence in a subject in remission.

The term "treatment" in the present description refers to treatment of a subject afflicted with diseases and symptoms, including the improvement and alleviation of diseases and symptoms.

In target treatment and/or prevention, the compound represented by formula (I) and a pharmaceutically acceptable salt thereof can be formulated as a pharmaceutical composition according to a standard pharmaceutical practice in order to use them. The present invention provides a pharmaceutical composition comprising the compound represented by formula (I) or a pharmaceutically acceptable salt thereof, and optionally, a pharmaceutically acceptable carrier or diluting agent.

When the compound of the present invention is administered to mammals (for example, human, equine, bovine, pig, and the like, preferably human), the said compound is administered systemically or topically, orally or parenterally, and preferably orally.

The pharmaceutical composition of the present invention can be prepared by suitably selecting formulations depending on the administration methods according to preparation methods generally used for various preparations.

Oral formulations of the pharmaceutical composition include tablets, pills, powders, granules, capsules, pharmaceutical solutions, suspensions, emulsions, syrups, elixirs, and the like. Preparation of such formulations of the pharmaceutical composition can be carried out according to a conventional method by suitably choosing commonly-used additive agents, when needed, such as excipients, bonding agents, disintegrants, lubricants, swelling agents, swelling agent enhancers, coating agents, plasticizers, stabilizers, antiseptic agents, antioxidants, colorants, solubilizing agents, suspending agents, emulsifiers, sweetening agents, preservatives, buffer agents, diluents, wetting agents, and the like.

Parenteral formulations of the pharmaceutical composition include injections, ointments, gels, creams, poultices, adhesive skin patches, sprays, inhalants, sprays ophthalmic solutions, nasal preparations, suppositories, inhalants, and the like. Preparation of such formulations of the pharmaceutical composition is carried out according to a conventional method by suitably choosing commonly used additives such as stabilizing agents, antiseptic agents, solubilizing agents, moisturizers, preservatives, antioxidants, flavoring agents, gelators, neutralizers, solubilizing agents, buffering agents, isotonic agents, surfactants, colorants, buffer agents, thickening agents, wetting agents, bulking agents, absorption promoters, suspending agents, binders, and the like, when needed.

The dosage of the compound of the present invention varies depending on symptoms, age, and body weight, and by drugs administered in combination. In case of oral administration, the compound is administered 1 to several times/day per person, 0.00002 to 20 mg/kg body weight, preferably 0.005 to 10 mg/kg body weight. In case of parental administration, 1 to several times/day per person, 0.00001 to 10 mg/kg body weight, preferably 0.0025 to 5 mg/kg body weight.

The compound of formula (I) can be used as an S1P1 receptor agonist because of its specific agonist effect at a S1P1 receptor.

The compound of formula (I) can be used as an immunosuppressant because of its specific agonist effect at an S1P1 receptor.

According to the present invention, there is provided a method for treating and/or preventing clinical conditions mediated by an S1P1 receptor, comprising administering a prophylactically or therapeutically safe and effective amount of the compound of formula (I) or a pharmaceutically acceptable salt thereof to mammals including human.

According to the present invention, there is provided use of the compound of formula (I) or a pharmaceutically acceptable salt thereof in the manufacture of a medicament for treating and/or preventing clinical conditions mediated by an S1P1 receptor.

According to the present invention, there is provided a method for treating and/or preventing transplant rejection, autoimmune diseases, or allergic diseases, comprising administering a prophylactically or therapeutically safe and effective amount of the compound of formula (I) or a pharmaceutically acceptable salt thereof to the mammals including human.

According to the present invention, there is provided use of the compound of formula (I) or a pharmaceutically acceptable salt thereof in the manufacture of a medicament for treating and/or preventing transplant rejection, autoimmune diseases, or allergic diseases.

According to the present invention, the following invention is also provided.

(1) A compound represented by the following formula (I) or a pharmaceutically acceptable salt.

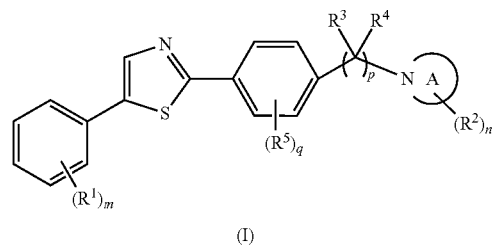

[Compound 9]

(I)

wherein

A represents a 4-membered to 7-membered cyclic amine;

m represents an integer of 1 to 5;

n represents an integer of 1 to 3;

p represents an integer of 1 to 3;

q represents an integer of 0 to 4;

$R^1$ represents $C_{1-10}$ alkyl, $C_{1-10}$ alkoxy, phenyl, phenoxy, a halogen atom, halogeno $C_{1-3}$ alkyl, or cyano (when m is 2 or more, $R^1$ may be each independently identical or different);

$R^2$ represents COOH, $COOR^6$, $CONR^7R^8$, or tetrazolyl (when n is 2 or more, $R^2$ may be each independently identical or different);

$R^3$ is a hydrogen atom or $C_{1-6}$ alkyl;

$R^4$ is a hydrogen atom or $C_{1-6}$ alkyl;

or $R^3$ and $R^4$ may together form an oxo group (when p is 2 or more, $R^3$ and $R^4$ may be each independently identical or different);

$R^5$ is $C_{1-6}$ alkyl, $C_{1-6}$ alkoxy, halogen, halogeno $C_{1-3}$ alkyl, cyano, hydroxyl, amino (when q is 2 or more, $R^5$ may be each independently identical or different);

$R^6$ is $C_{1-10}$ alkyl; and $R^7$ and $R^8$ are each independently a hydrogen atom or $C_{1-10}$ alkyl.

(2) The compound according to (1) or a pharmaceutically acceptable salt thereof, wherein n is 1; and p is 1.

(3) The compound according to (1) or (2) or a pharmaceutically acceptable salt thereof, wherein $R^2$ is COOH.

(4) A pharmaceutical composition comprising, as an active ingredient, the compound according to any one of (1) to (3) or a pharmaceutically acceptable salt thereof.

(5) The pharmaceutical composition according to (4), which is used for preventing and/or treating autoimmune diseases or allergic diseases.

EXAMPLES

The present invention hereinafter is specifically explained by Examples, however, the present invention is not limited to those.

The symbol "MS" in the Examples refers to "mass spectrometry". "MS" was measured using a Waters LC-MS (ZQ or TQD).

The symbol "NMR" in the Examples refers to "nuclear magnetic resonance". "NMR" was carried out by using a JEOL JNM-LA 400.

As silica gel applied for column chromatography, Merck Kieselgel 60 (particle size: 0.060 to 0.200 mm or 0.040 to 0.063 mm) was used.

And Merck Kieselgel 60 $F_{254}$ was used as a thin-layer chromatography (TLC) plate.

The following abbreviations are used in the present description.

DMF: N,N-dimethylformamide
NBS: N-bromosuccinimide
THF: tetrahydrofuran

Example 1

Methyl 1-(4-(5-(4-isopropoxyphenyl)thiazol-2-yl)benzyl)azetidine-3-carboxylate (1) 4-(thiazol-2-yl)benzaldehyde 2-Bromothiazole (0.538 ml, 6.06 mmol), 4-formylphenylboronic acid (1.0 g, 6.67 mmol), and $Na_2CO_3$ (1.61 g) were suspended in the mixed solution of toluene (25 ml), ethanol (5 ml), and $H_2O$ (5 ml). The mixture was stirred at room temperature for 15 minutes under an argon gas atmosphere. After reducing the pressure inside of the reaction container by using a vacuum line, the mixture was degassed by introducing Ar gas and this procedure was repeated twice. After that, tetrakis (triphenylphosphine)palladium (0.701 g, 0.606 mmol) was added, and the mixture was stirred for 15 hours by heating under reflux. The end point of the reaction was confirmed on TLC (EtOAc:n-hexane=1:4), and the mixture was cooled to room temperature. $H_2O$ (50 ml) and EtOAc (50 ml) were added and the mixture was stirred for 15 minutes. Black insoluble matter was removed by filtration with Celite and the filtrate was separated by the step of extraction/separation. The organic layer was washed with saturated brine (50 ml) and dried over anhydrous magnesium sulfate. The solvent was evaporated under reduced pressure. The resulting residue was purified on silica gel column chromatography (EtOAc:hexane=1:3) to obtain the title compound (985 mg) as an opaque white solid.

(2) 4-(5-bromothiazol-2-yl)benzaldehyde

The compound obtained in the Example 1(1) (940 mg, 4.97 mmol) was dissolved in DMF (25 ml), and NBS (1.06 g, 5.96 mmol) was added to the solution. After the mixture was stirred at room temperature for 16 hours, the progress of the reaction was confirmed on TLC (EtOAc:hexane=1:3), followed by the addition of NBS (265 mg). After stirring the mixture at room temperature for 20 hours, NBS (265 mg) was further added. The resulting mixture was stirred at room temperature for 1 hour. The reaction mixture was added to 8% $NaHCO_3$ aqueous solution (50 ml) and the resulting mixture was stirred at room temperature for 15 minutes and further for 15 minutes under ice cooling. The precipitate was collected using a Kiriyama filter and washed with distilled water. The precipitate was dried at 40° C. for 3 hours under reduced pressure to obtain the title compound (981 mg) as a grayish white solid.

(3) 4-(5-(4-isopropoxyphenyl)thiazol-2-yl)benzaldehyde

The compound obtained in the Example 1 (2) (950 mg, 3.543 mmol), 4-isopropoxyphenylboronic acid (585 mg, 3.897 mmol), $Na_2CO_3$ (530 mg, 5.000 mmol) were dissolved in 1,4-dioxane (15 ml) and $H_2O$ (5 ml) mixed solution and the mixture was stirred at room temperature for 15 minutes under an argon gas atmosphere. The pressure inside of the reaction container was reduced by using a vacuum line, the mixture was degassed by introducing Ar gas and this procedure was repeated twice. After that, tetrakis(triphenylphosphine)palladium (409 mg, 0.354 mmol) was poured into the reaction container, the mixture was stirred for 5 hours while maintaining outside temperature of the container at 87° C. The end point of the reaction was confirmed on TLC (EtOAc:n-hexane=1:3) and the mixture was cooled to room temperature. The reaction solution was poured in the mixed solution of $H_2O$ (40 ml) and $CHCl_3$ (40 ml) and the resulting mixture was stirred for 10 minutes. The organic layer was washed with saturated brine (50 ml) and dried over anhydrous magnesium sulfate. The solvent was evaporated under reduced pressure. The residue was purified on silica gel column chromatography (EtOAc:$CHCl_3$=1:100) to obtain the title compound (928 mg) as bright yellow solid.

(4) methyl 1-(4-(5-(4-isopropoxyphenyl)thiazol-2-yl)benzyl)azetidine-3-carboxylate 3-azetidine carboxylic acid methyl ester (506 mg, 3.34 mmol) was dissolved in methanol (5 ml) and diisopropylethylamine (710 ml, 4.17 mmol) was added to the solution, followed by stirring for 15 minutes. Separately, the compound obtained in the Example 1 (3) (900 mg, 2.783 mmol) was dissolved in the mixed solution of chloroform (10 ml)-methanol (5 ml)-acetic acid (1 ml). This mixture was added to the solution of azetidine carboxylic acid methyl ester/methanol mentioned above. After the mixture was stirred at room temperature for 1 hour, the solution was cooled in ice, borane 2-picoline complex (357 mg, 3.349 mmol) was added, followed by stirring for 1 hour. The mixture was further stirred at room temperature for 15 hours. The end point of the reaction was confirmed with TLC (MeOH:CHCl$_3$=1:20). To the reaction solution was added 5 N—HCl (10 ml) and the reaction solution was stirred for 20 minutes. The reaction solution was gradually added to the mixed solution of chloroform (100 ml) and saturated sodium bicarbonate aqueous solution (40 ml), and the organic layer and the aqueous layer were separated by the step of extraction/separation. By the addition of small amount of methanol (about 20 ml) to the organic layer (suspension), the suspension was resolved, and the aqueous layer and the organic layer were separated again. By the step of extraction/separation, the organic layer was separated. The resulting organic layer was dried over anhydrous magnesium sulfate and the solvent was evaporated under reduced pressure to yield the title compound as a crude product. The crude product was purified on column chromatography (MeOH:CHCl$_3$=1:40) to obtain the title compound (900 mg) as a pale yellow solid.

MS (ESI) m/z: 423 (M+H)$^+$

Example 2

1-(4-(5-(4-isopropoxyphenyl)thiazol-2-yl)benzyl)azetidine-3-carboxylic acid

The compound obtained in the Example 1(4) (890 mg, 2.106 mmol) was dissolved in THF (30 ml), 1 N—NaOH (15 ml) was added to the mixture, and the resulting mixture was stirred at room temperature for 4 hours. Consumption of the raw material was confirmed on TLC (MeOH:CHCl$_3$=1:20) and the mixture was adjusted to around pH=4 by adding 1 N—HCl (16 ml). Since evaporation of THF under reduced pressure resulted in the precipitation of a pale yellow solid, the mixture was quietly stirred under ice cooling for 20 minutes. Subsequently, the precipitate was filtered using a Kiriyama funnel and washed with a small amount of water. The residue was dried at 40° C. for 3 hours under reduced pressure to obtain the title compound (773 mg) as a pale yellow solid.

MS (ESI) m/z: 409 (M+H)$^+$

NMR (DMSO-d$_6$) δ: 1.28 (6H, d, J=6.0 Hz), 3.22-3.30 (1H, m), 3.28-3.35 (2H, m), 3.45-3.54 (2H, m), 3.68 (2H, s), 4.62-4.71 (1H, m), 7.00 (2H, d, J=8.8 Hz), 7.41 (2H, d, J=8.1 Hz), 7.61 (2H, d, J=8.8 Hz), 7.89 (2H, d, J=8.1 Hz), 8.13 (1H, s)

Example 3

1-(4-(5-(3-chloro-4-isopropoxyphenyl)thiazol-2-yl)benzyl)azetidine-3-carboxylic acid (1) 4-(5-(3-chloro-4-isopropoxyphenyl)thiazol-2-yl)benzaldehyde The title compound (570 mg) was obtained as a bright yellow solid from the reaction of the compound obtained in the Example 1 (2) (500 mg, 1.86 mmol) and 3-chloro-4-isopropoxyphenylboronic acid (440 mg, 2.05 mmol) by the similar method as the Example 1 (3).

(2) Methyl 1-(4-(5-(3-chloro-4-isopropoxyphenyl)thiazol-2-yl)benzyl)azetidine-3-carboxylate The title compound (360 mg) was obtained from the compound obtained in the Example 3(1) (250 mg, 0.699 mmol), as brownish yellow oily material by the similar method of the Example 1 (4).

(3) 1-(4-(5-(3-chloro-4-isopropoxyphenyl)thiazol-2-yl)benzyl)azetidine-3-carboxylic acid The title compound (425 mg) was obtained from the compound obtained in the Example 3 (2) (597 mg, 1.31 mmol), as a pale yellow solid by the similar method of the Example 2.

MS (ESI) m/z: 443 (M+H)$^+$

NMR (DMSO-d$_6$) δ: 1.31 (6H, d, J=6.0 Hz), 3.38-3.47 (1H, m), 3.68-3.76 (2H, m), 3.78-3.85 (2H, m), 4.01-4.07 (2H, brs), 4.69-4.78 (1H, m), 7.26 (1H, d, J=8.8 Hz), 7.54 (2H, d, J=8.1 Hz), 7.59 (1H, dd, J=8.6, 2.3 Hz), 7.83 (1H, d, J=2.3 Hz), 7.95 (2H, d, J=8.2 Hz), 8.29 (1H, s)

Example 4

2-(4-((3-(2H-tetrazol-5-yl)azetidin-1-yl)methyl)phenyl)-5-(4-isopropoxyphenyl)thiazole (1) (5-(4-isopropoxyphenyl)-2-(4-((3-(2-(4-methoxybenzyl-2H-tetrazol-5-yl)azetidin-1-yl)methyl)phenyl)thiazole The title compound (14 mg) was obtained from the compound obtained in the Example 1 (3) (15.8 mg, 0.0489 mmol) and 5-(azetidine-3-yl)-2-(4-methoxybenzyl)-2H-tetrazole (12 mg, 0.0489 mmol, WO2008/24892) as a pale yellow solid by the similar method of the Example 1 (4).

(2) 2-(4-((3-(2H-tetrazol-5-yl)azetidin-1-yl)methyl)phenyl)-5-(4-isopropoxyphenyl)thiazole The compound obtained in the Example 4 (1) (14.0 mg, 0.0253 mmol) was dissolved in trifluoroacetic acid (2 ml) and the solution was stirred at 60° C. for 6 hours. The solvent was evaporated under reduced pressure. The resulting residue was dissolved in 1 N—NaOH, and precipitates produced during neutralization with 1 N—HCl were filtered to obtain the title compound (12.4 mg).

MS (ESI) m/z: 433 (M+H)$^+$

Example 5

1-(4-(5-(4-isopropoxyphenyl)thiazol-2-yl)benzyl)piperidine-4-carboxylic acid (1) ethyl 1-(4-(5-(4-isopropoxyphenyl)thiazol-2-yl)benzyl)piperidine-4-carboxylate The title compound (68.0 mg) was obtained from the compound obtained in the Example 1 (3) (70.0 mg, 0.216 mmol) and ethyl isonipecotate (51.0 mg, 0.325 mmol) as a colorless solid by the similar method of the Example 1 (4).

(2) 1-(4-(5-(4-isopropoxyphenyl)thiazol-2-yl)benzyl)piperidine-4-carboxylic acid The title compound (56.9 mg) was obtained from the compound obtained in the Example 5 (1) (68.0 mg, 0.146 mmol) as a pale yellow solid by the similar method of the Example 2.

MS (ESI) m/z: 437 (M+H)$^+$

Example 6

1-(4-(5-phenylthiazol-2-yl)benzyl)azetidine-3-carboxylic acid (1) 4-(5-phenylthiazol-2-yl)benzaldehyde The title compound (850 mg) was obtained from the compound obtained in the Example 1(2) (1.0 g, 3.73 mmol) and phenylboronic acid (500 mg, 4.10 mmol) as a bright yellow solid by the similar method of the Example 1 (3).

(2) methyl 1-(4-(5-phenylthiazol-2-yl)benzyl)azetidine-3-carboxylate

The title compound (600 mg) was obtained from the compound obtained in the Example 6(1) (600 mg, 2.26 mmol) as a yellow solid by the similar method of the Example 1(4).

(3) 1-(4-(5-phenylthiazol-2-yl)benzyl)azetidine-3-carboxylic acid

The title compound (250 mg) was obtained from the compound obtained in the Example 6(2) (350 mg, 0.960 mmol) as a pale yellow solid by the similar method of the Example 2. MS (ESI) m/z: 351 (M+H)$^+$

Example 7

1-(4-(5-(3-isopropoxyphenyl)thiazol-2-yl)benzyl)azetidine-3-carboxylic acid

(1) 4-(5-(3-isopropoxyphenyl)thiazol-2-yl)benzaldehyde

The title compound (1.4 g) was obtained by the reaction of the compound obtained in the Example 1 (2) (1.50 g, 5.59 mmol) and 3-isopropylphenylboronic acid (1.11 g, 6.15 mmol) as a bright yellow solid by the similar method of the Example 1(3).

(2) methyl 1-(4-(5-(3-isopropoxyphenyl)thiazol-2-yl)benzyl)azetidine-3-carboxylate The title compound (710 mg) was obtained from the compound obtained in the Example 7 (1) (750 mg, 2.32 mmol) as a yellow solid by the similar method of the Example 1(4).

(3) 1-(4-(5-(3-isopropoxyphenyl)thiazol-2-yl)benzyl)azetidine-3-carboxylic acid The title compound (320 mg) was obtained from the compound obtained in the Example 7(2) (350 mg, 0.828 mmol) as a pale yellow solid by the similar method of the Example 2. MS (ESI) m/z: 409 (M+H)$^+$

Example 8

1-(1-(4-(5-(4-isopropoxyphenyl)thiazol-2-yl)phenyl)ethyl)azetidine-3-carboxylic acid

(1) 1-(4-(thiazol-2-yl)phenyl)ethanone

4-Bromoacetophenone (500 mg, 2.51 mmol) and 2-(tributylstannyl)thiazole (0.948 ml, 3.014 mmol) were dissolved in 1,4-dioxane (8 ml), and bis(triphenylphosphine)palladium dichloride (176 mg), was added to the solution under an argon gas atmosphere. The mixture was stirred at 90° C. for 8 hours. After the reaction solution was cooled to room temperature, chloroform and 1 N—HCl were added to the solution, and the extraction/separation step was carried out. The organic layer was washed with saturated brine, dried over anhydrous magnesium sulfate, and the solvent was evaporated under reduced pressure. The residue was purified on silica gel column chromatography (EtOAc:hexane=1:3) to yield the title compound (643 mg) as an opaque white solid.

(2) 1-(4-(5-bromothiazol-2-yl)phenyl)ethanone

The title compound (490 mg) was obtained from the compound obtained in the Example 8(1) (643 mg, 2.512 mmol) as a pale brown solid by the similar method of the Example 1(2).

(3) 1-(4-(5-(4-isopropoxyphenyl)thiazol-2-yl)phenyl)ethanone

The title compound (158 mg) was obtained from the compound obtained in the Example 8(2) (200 mg, 0.708 mmol) and 4-isopropoxyphenylboronic acid (153 mg, 0.850 mmol) as a dark brown solid by the similar method of the Example 1 (3).

(4) methyl 1-(1-(4-(5-(4-isopropoxyphenyl)thiazol-2-yl)phenyl)ethyl)azetidine-3-carboxylate The title compound (24.4 mg) was obtained from the compound obtained in the Example 8(3) (91.0 mg, 0.270 mmol) as a pale yellow solid by the similar method of the Example 1(4).

(5) 1-(1-(4-(5-(4-isopropoxyphenyl)thiazol-2-yl)phenyl)ethyl)azetidine-3-carboxylic acid The title compound (22.6 mg) was obtained from the compound obtained in the Example 8(4) (35.6 mg, 0.0815 mmol) as a pale yellow solid by the similar method of the Example 2. MS (ESI) m/z: 423 (M+H)$^+$

Example 9

(S)-1-(4-(5-(4-isopropoxyphenyl)thiazol-2-yl)benzyl)pyrrolidine-2-carboxylic acid

(1) methyl (S)-1-(4-(5-(4-isopropoxyphenyl)thiazol-2-yl)benzyl)pyrrolidine-2-carboxylate The title compound (69.1 mg) was obtained by the reaction of the compound obtained in the Example 1(3) (69.1 mg, 0.158 mmol) and L-proline methyl ester (46.1 mg, 0.278 mmol) as a yellow solid by the similar method of the Example 1 (4).

(2) (S)-1-(4-(5-(4-isopropoxyphenyl)thiazol-2-yl)benzyl)pyrrolidine-2-carboxylic acid The title compound (50.0 mg) was obtained from the compound obtained in the Example 9(1) (68.0 mg, 0.146 mmol) as a pale yellow solid by the similar method of the Example 2. MS (ESI) m/z: 423 (M+H)$^+$

Example 10

1-(4-(5-(4-isopropoxyphenyl)thiazol-2-yl)benzyl)piperidine-3-carboxylic acid

(1) ethyl 1-(4-(5-(4-isopropoxyphenyl)thiazol-2-yl)benzyl)piperidine-3-carboxylate The title compound (75.6 mg) was obtained by the reaction of the compound obtained in the Example 1(3) (60.0 mg, 0.186 mmol) and ethyl nipecotate (43.7 mg, 0.278 mmol) as a pale yellow solid by the same method of the Example 1(4).

(2) 1-(4-(5-(4-isopropoxyphenyl)thiazol-2-yl)benzyl)piperidine-3-carboxylic acid The title compound (63.0 mg) was obtained from the compound obtained in the Example 10(1) (75.6 mg, 0.163 mmol) as a pale yellow solid by the similar method of the Example 2.
MS (ESI) m/z: 437 (M+H)$^+$ Example 11

1-(4-(5-(3-chloro-4-isopropoxyphenyl)thiazol-2-yl)-3-fluorobenzyl)azetidine-3-carboxylic acid (1) 3-fluoro-4-(thiazol-2-yl)benzaldehyde The title compound (149 mg) was obtained from 4-bromo-3-fluorobenzaldehyde (275 mg, 1.36 mmol) and 2-(tributylstannyl)thiazole (558 mg), by the similar method of the Example 8(1).

(2) 4-(5-bromothiazol-2-yl)-3-fluorobenzaldehyde

The title compound (123 mg) was obtained from the compound obtained in the Example 11(1) (146 mg, 0.705 mmol), as a colorless solid by the similar method of the Example 1(2).

(3) 4-(5-(3-chloro-4-isopropoxyphenyl)thiazol-2-yl)-3-fluorobenzaldehyde

The title compound (139 mg) was obtained by the reaction of the compound obtained in the Example 11(2) (123 mg, 0.430 mmol) and 3-chloro-4-isopropoxyphenylboronic acid (101 mg, 0.473 mmol) as a bright yellow solid by the similar method of the Example 1(3).

(4) methyl 1-(4-(5-(3-chloro-4-isopropoxyphenyl)thiazol-2-yl)-3-fluorobenzyl)azetidine-3-carboxylate The title compound (138 mg) was obtained from the compound obtained in the Example 11(3) (139 mg, 0.370 mmol) as a pale yellow solid by the similar method of the Example 1(4).

(5) 1-(4-(5-(3-chloro-4-isopropoxyphenyl)thiazol-2-yl)-3-fluorobenzyl)azetidine-3-carboxylic acid The title compound (99.0 mg) was obtained from the compound obtained in the Example 11(4) (137 mg, 0.288 mmol) as a colorless solid by the similar method of the Example 2.
MS (ESI) m/z: 461 (M+H)$^+$
NMR (DMSO-d$_6$) δ: 1.31 (6H, d, J=6.0 Hz), 3.19-3.26 (3H, m), 3.40-3.47 (2H, m), 3.62 (2H, s), 4.70-4.78 (1H, m), 7.25 (1H, d, J=8.9 Hz), 7.28 (1H, d, J=8.1 Hz), 7.31 (1H, d, J=12.3 Hz), 7.62 (1H, dd, J=8.6, 2.3 Hz), 7.86 (1H, d, J=2.3 Hz), 8.17 (1H, t, J=8.0 Hz), 8.35 (1H, d, J=2.3 Hz)

Example 12

1-(3-chloro-4-(5-(4-isopropoxyphenyl)thiazol-2-yl)benzyl)azetidine-3-carboxylic acid (1) 3-chloro-4-(thiazol-2-yl)benzaldehyde The title compound (758 mg) was obtained by the reaction of the 4-bromo3-chlorobenzaldehyde (1063 mg, 4.84 mmol) and 2-(tributylstannyl)thiazole (1994 mg), by the similar method of the Example 8(1).

(2) 4-(5-bromothiazole-2-yl)-3-chlorobenzaldehyde

The title compound (887 mg) was obtained from the compound obtained in the Example 12(1) (758 mg, 3.39 mmol) as a pale yellow solid by the similar method of the Example 1(2).

(3) 3-chloro-4-(5-(4-isopropoxyphenyl)thiazol-2-yl)benzaldehyde

The title compound (995 mg) was obtained by the reaction of the compound obtained in the Example 12(2) (887 mg, 2.93 mmol) and 4-isopropoxyphenylboronic acid (634 mg, 3.52 mmol) as a bright yellow solid by the similar method of the Example 1(3).

(4) 1-(3-chloro-4-(5-(4-isopropoxyphenyl)thiazol-2-yl)benzyl)azetidine-3-carboxylate The title compound (49 mg) was obtained from the compound obtained in the Example 12(3) (200 mg, 0.559 mmol), as a pale yellow solid by the similar method of the Example 1(4).

(5) 1-(3-chloro-4-(5-(4-isopropoxyphenyl)thiazol-2-yl)benzyl)azetidine-3-carboxylic acid The title compound (40 mg) was obtained from the compound obtained in the Example 12(4) (49 mg, 0.107 mmol) as a colorless solid by the similar method of the Example 2.
MS (ESI) m/z: 443 (M+H)$^+$
NMR (DMSO-d$_6$) δ: 1.28 (6H, d, J=6.0 Hz), 3.18-3.26 (3H, m), 3.38-3.44 (2H, m), 3.60 (2H, s), 4.63-4.70 (1H, m), 7.00 (2H, d, J=8.8 Hz), 7.38 (1H, dd, J=8.2, 1.3 Hz), 7.51 (1H, s), 7.65 (2H, d, J=8.8 Hz), 8.16 (1H, d, J=8.2 Hz), 8.26 (1H, s)

Example 13

1-(3-butyl-4-(5-(4-isopropoxyphenyl)thiazol-2-yl)benzyl)azetidine-3-carboxylic acid (1) 2-(2-chloro-4-(1,3-dioxolan-2-yl)phenyl)-5-(4-isopropoxyphenyl)thiazole The compound obtained in the Example 12(3) (1394 mg, 3.90 mmol) was dissolved in toluene (15 ml) and ethylene glycol (5 ml), and p-toluenesulfonic acid monohydrate (872 mg) was added to the solution. The mixture was heated to reflux for 8 hours. Saturated sodium bicarbonate aqueous solution was added to terminate the reaction, and the mixture was diluted with chloroform followed by the step of extraction/separation. The organic layer was washed with saturated brine. After the organic layer was dried over anhydrous magnesium sulfate, the solvent was evaporated under reduced pressure to yield the title compound as a crude product. The resulting crude product was purified on column chromatography (EtOAc:CHCl$_3$=1:100) to obtain the title compound (1400 mg) as a colorless solid.

(2) 2-(2-butyl-4-(1,3-dioxolan-2yl)phenyl)-5-(4-isopropoxyphenyl)thiazole

The compound obtained in the Example 13(1) (100 mg, 0.249 mmol) was dissolved in NMP (1.5 ml) under an argon gas atmosphere, and a THF solution of 0.5 M-zinc butyl bromide (1.5 ml) and Pd(PtBu$_3$) (13 mg) were added to the solution. The mixture was heated at 150° C. for 30 minutes under irradiation of microwave. The mixture was diluted with chloroform and saturated sodium bicarbonate aqueous solution followed by the step of extraction/separation, and the organic layer was washed with saturated brine. After the organic layer was dried over anhydrous magnesium sulfate, the solvent was evaporated under reduced pressure to obtain the title compound as a crude product. The resulting crude product was purified on column chromatography (EtOAc:CHCl$_3$=1:100) to obtain the title compound (32.4 mg) as a colorless oily substance.

(3) 3-butyl-4-(5-(4-isopropoxyphenyl)thiazol-2-yl)benzaldehyde

The compound obtained in the Example 13(2) (32.4 mg, 0.0755 mmol) was dissolved in THF (4 ml) and 5 N—HCl (1 ml) was added to the solution, and the mixture was stirred overnight. The mixture was diluted with chloroform and saturated sodium bicarbonate water followed by the step of extraction/separation. The organic layer was washed with saturated brine. After the organic layer was dried over anhydrous magnesium sulfate, the solvent was evaporated under reduced pressure to obtain the title compound (25.6 mg).

(4) methyl 1-(3-butyl-4-(5-(4-isopropoxyphenyl)thiazol-2-yl)benzyl)azetidine-3-carboxylate The title compound (24.5 mg) was obtained from the compound obtained in the Example 13(3) (25.6 mg, 0.0675 mmol) as a pale yellow oily substance by the similar method of the Example 1(4).

(5) 1-(3-butyl-4-(5-(4-isopropoxyphenyl)thiazol-2-yl)benzyl)azetidine-3-carboxylic acid The title compound (19 mg) was obtained from the compound obtained in the Example 13(4) (24.5 mg, 0.0512 mmol) as a colorless solid by the similar method of the Example 2.
MS (ESI) m/z: 465 (M+H)$^+$
NMR (DMSO-d$_6$) δ: 0.86 (3H, t, J=7.3 Hz), 1.24-1.32 (2H, m), 1.26 (6H, d, J=6.0 Hz), 1.50 (2H, quin, J=7.8 Hz), 2.95 (2H, t, J=7.7 Hz), 3.35-3.41 (1H, m), 3.57-3.65 (2H, brs), 3.71-3.79 (2H, brs), 3.88-3.95 (2H, brs), 4.62-4.70 (1H, m), 7.00 (2H, d, J=8.9 Hz), 7.30 (1H, d, J=7.9 Hz), 7.36 (1H, s), 7.62 (2H, d, J=8.7 Hz), 7.64 (1H, d, J=8.0 Hz), 8.20 (1H, s)

Example 14

1-(3-cyclopropyl-4-(5-(4-isopropoxyphenyl)thiazol-2-yl)benzyl)azetidine-3-carboxylic acid

(1) 2-(2-cyclopropyl-4-(1,3-dioxolan-2-yl)phenyl)-5-(4-isopropoxyphenyl)thiazole The title compound (74.8 mg) was obtained from the compound obtained in the Example 13(1) (100 mg, 0.249 mmol) and a THF solution of 0.5 M-cyclopropylzinc bromide (1.5 ml) as a pale yellow oily substance by the similar method of the Example 13(2)

(2) 3-cyclopropyl-4-(5-(4-isopropoxyphenyl)thiazol-2-yl)benzaldehyde

The title compound (68.5 mg) was obtained from the compound obtained in the Example 14(1) (74.8 mg, 0.183 mmol) as a bright yellow oily substance by the similar method of the Example 13(3).

(3) methyl 1-(3-cyclopropyl-4-(5-(4-isopropoxyphenyl)thiazol-2-yl)benzyl)azetidine-3-carboxylate The title compound (60 mg) was obtained from the compound obtained in the Example 14(2) (68.5 mg, 0.188 mmol) as a pale yellow oily substance by the similar method of the Example 1(4).

(4) 1-(3-cyclopropyl-4-(5-(4-isopropoxyphenyl)thiazol-2-yl)benzyl)azetidine-3-carboxylic acid The title compound (54.1 mg) was obtained from the compound obtained in the Example 14(3) (60 mg, 0.130 mmol) as a colorless solid by the similar method of the Example 2.
MS (ESI) m/z: 449 (M+H)$^+$
NMR (DMSO-d$_6$) δ: 0.72-0.76 (2H, m), 0.99-1.04 (2H, m), 1.21-1.24 (1H, m), 1.28 (6H, d, J=6.0 Hz), 2.45-2.50 (1H, m), 3.18-3.24 (2H, m), 3.35-3.41 (1H, m), 3.57 (2H, s), 3.57-3.61 (1H, m), 4.63-4.70 (1H, m), 6.99 (2H, d, J=8.9 Hz), 7.01 (1H, s), 7.19 (1H, dd, J=8.0, 1.4 Hz), 7.62 (2H, d, J=8.8 Hz), 7.74 (1H, d, J=8.0 Hz), 8.19 (1H, s)

Example 15

1-(3-ethyl-4-(5-(4-isopropoxyphenyl)thiazol-2-yl)benzyl)azetidine-3-carboxylic acid

(1) 2-(2-ethyl-4-(1,3-dioxolan-2-yl)phenyl)-5-(4-isopropoxyphenyl)thiazole

The title compound (75.3 mg) was obtained from the compound obtained in the Example 13(1) (100 mg, 0.249 mmol) and a hexane solution of 1.0 M-diethylzinc (1.5 ml) as a pale yellow oily substance by the similar method of the Example 13(2)

(2) 3-ethyl-4-(5-(4-isopropoxyphenyl)thiazol-2-yl)benzaldehyde

The title compound (71 mg) was obtained from the compound obtained in the Example 15(1) (75.3 mg, 0.194 mmol) as a bright yellow oily substance by the similar method of the Example 13(3).

(3) methyl 1-(3-ethyl-4-(5-(4-isopropoxyphenyl)thiazol-2-yl)benzyl)azetidine-3-carboxylate The title compound (68 mg) was obtained from the compound obtained in the Example 15(2) (71 mg, 0.202 mmol) as a pale yellow oily substance by the similar method of the Example 1(4).

(4) 1-(3-ethyl-4-(5-(4-isopropoxyphenyl)thiazol-2-yl)benzyl)azetidine-3-carboxylic acid The title compound (60 mg) was obtained from the compound Example 15(3) (68 mg, 0.153 mmol) as a colorless solid by the similar method of the Example 2.
MS (ESI) m/z: 437 (M+H)$^+$
NMR (DMSO-d$_6$) δ: 1.14 (3H, t, J=7.5 Hz), 1.28 (6H, d, J=6.0 Hz), 2.96 (2H, q, J=7.5 Hz), 3.18-3.24 (3H, m), 3.38-3.44 (2H, m), 3.58 (2H, s), 4.62-4.69 (1H, m), 6.99 (2H, d, J=8.8 Hz), 7.20 (1H, dd, J=7.9, 1.5 Hz), 7.27 (1H, s), 7.58 (1H, d, J=7.9 Hz), 7.61 (2H, d, J=8.8 Hz), 8.18 (1H, s)

Example 16

1-(4-(5-(4-cyclopropoxyphenyl)thiazol-2-yl)benzyl) azetidine-3-carboxylic acid (1) 4-(5-(4-cyclopropoxyphenyl)thiazol-2-yl)benzaldehyde The title compound (325 mg) was obtained by the reaction of the compound obtained in the Example 1(2) (288 mg, 1.08 mmol) and 4-cyclopropoxyphenylboronic acid (249 mg, 1.40 mmol) as a bright yellow solid by the similar method of the Example 1(3).

(2) methyl 1-(4-(5-(4-cyclopropoxyphenyl)thiazol-2-yl)benzyl)azetidine-3-carboxylate The title compound (70 mg) was obtained from the compound obtained in the Example 16(1) (325 mg, 1.01 mmol) as a pale yellow solid by the similar method of the Example 1(4).

(3) 1-(4-(5-(4-cyclopropoxyphenyl)thiazol-2-yl)benzyl)azetidine-3-carboxylic acid The title compound (55 mg) was obtained from the compound obtained in the Example 16(2) (70 mg, 0.166 mmol) as a colorless solid by the similar method of the Example 2.
MS (ESI) m/z: 407 (M+H)$^+$ Example 17

1-(3-fluoro-4-(5-(4-isopropoxyphenyl)thiazol-2-yl) benzyl)azetidine-3-carboxylic acid The title compound (650 mg) was obtained from the compound obtained in the Example 11 (2) (1.3 g) as a raw material as a pale yellow solid by the similar method of the Example 1(3), Example 1(4), and Example 2.
MS (ESI) m/z: 427 (M+H)$^+$
NMR (DMSO-d$_6$) δ: 1.28 (6H, d, J=6.0 Hz), 3.38 (1H, quin, J=7.8 Hz), 3.56-3.63 (2H, m), 3.69-3.77 (2H, m), 3.94 (2H, s), 4.64-4.70 (1H, m), 6.99 (2H, d, J=8.8 Hz), 7.35 (1H, d, J=8.1 Hz), 7.43 (1H, d, J=12.2 Hz), 7.64 (2H, d, J=8.8 Hz), 8.20 (1H, t, J=8.0 Hz), 8.27 (1H, d, J=2.4 Hz)

Example 18

1-(4-(5-(4-isopropoxyphenyl)thiazol-2-yl)-3-methoxybenzyl)azetidine-3-carboxylic acid (1) 3-methoxy-4-(thiazol-2-yl)benzaldehyde The title compound (14 g) was obtained from the reaction of 4-bromo3-methoxybenzaldehyde (10 g, 46.8 mmol) and 2-(tributylstannyl)thiazole (17.5 g), by the similar method of the Example 8(1).

(2) 4-(5-bromothiazol-2-yl)-3-methoxybenzaldehyde

The title compound (1.3 g) was obtained from the compound obtained in the Example 18(1) (1.3 g) as a pale yellow solid by the similar method of the Example 1(2).

(3) 1-(3-chloro-4-(5-(4-isopropoxyphenyl)thiazol-2-yl)benzyl)azetidine-3-carboxylic acid The title compound (700 mg) was obtained from the compound obtained in the Example 18(2) (1.3 g) as a bright yellow solid by the similar method of the Example 1(3), Example 1(4), and Example 2.
MS (ESI) m/z: 439 (M+H)$^+$
NMR (DMSO-d$_6$) δ: 1.28 (6H, d, J=6.0 Hz), 3.33 (1H, quin, J=7.7 Hz), 3.42-3.49 (2H, m), 3.58-3.64 (2H, m), 3.81 (2H, s), 4.05 (3H, s), 4.62-4.69 (1H, m), 6.98 (2H, d, J=8.8 Hz), 7.04 (1H, d, J=8.2 Hz), 7.21 (1H, s), 7.61 (2H, d, J=8.8 Hz), 8.17 (1H, s), 8.21 (1H, d, J=8.0 Hz)

Example 19

1-(2-butyl-4-(5-(4-isopropoxyphenyl)thiazol-2-yl) benzyl)azetidine-3-carboxylic acid (1) 4-(5-bromothiazol-2-yl)-2-chlorobenzaldehyde The title compound (1.9 g) was obtained from 4-bromo-2-chlorobenzaldehyde (3 g), by the similar method of the Example 8(1) and Example 1(2).

(2) 2-(3-chloro-4-(1,3-dioxolan-2-yl) phenyl)-5-(4-isopropoxyphenyl)thiazole

The title compound (70 mg) was obtained from the compound obtained in the Example 19(1) (802 mg), Example 1(3) as a colorless solid by the similar method of the Example 13(1).

(3) 1-(2-butyl-4-(5-(4-isopropoxyphenyl)thiazol-2-yl)benzyl)azetidine-3-carboxylic acid The title compound (17.4 mg) was obtained from the compound obtained in the Example 19(2) (100 mg, 0.249 mmol) as a colorless solid by the similar method of the Example 13(2), Example 13(3), Example 13(4), and Example 13(5).
MS (ESI) m/z: 465 (M+H)$^+$
NMR (DMSO-d$_6$) δ: 0.93 (3H, t, J=7.3 Hz), 1.28 (6H, d, J=6.0 Hz), 1.34-1.41 (2H, m), 1.55 (2H, quin., J=8.0 Hz), 2.68 (2H, t, J=7.8 Hz), 3.17-3.24 (3H, m), 3.38-3.44 (2H, m), 3.59 (2H, s), 4.64-4.69 (1H, m), 6.99 (2H, d, J=8.8 Hz), 7.38 (1H, d, J=8.0 Hz), 7.60 (2H, d, J=8.8 Hz), 7.68 (1H, dd, J=7.9, 1.8 Hz), 7.71 (1H, d, J=1.6 Hz), 8.14 (1H, s)

Example 20

1-(2-ethyl-4-(5-(4-isopropoxyphenyl)thiazol-2-yl) benzyl)azetidine-3-carboxylic acid The title compound (17.4 mg) was obtained from the compound obtained in the Example 19(2) (100 mg, 0.249 mmol) as a colorless solid by the similar method of the Example 15(1), Example 13(3), Example 1(4), and Example 2.
MS (ESI) m/z: 437 (M+H)$^+$
NMR (DMSO-d$_6$) δ: 1.19 (3H, t, J=7.5 Hz), 1.28 (6H, d, J=6.0 Hz), 2.71 (2H, q., J=7.5 Hz), 3.19-3.24 (3H, m), 3.38-3.44 (2H, m), 3.60 (2H, s), 4.63-4.69 (1H, m), 6.99 (2H, d, J=8.8 Hz), 7.38 (1H, d, J=8.0 Hz), 7.61 (2H, d, J=8.7 Hz), 7.69 (1H, dd, J=7.9, 1.8 Hz), 7.73 (1H, d, J=1.8 Hz), 8.14 (1H, s)

Example 21

1-(4-(5-(4-isopropoxyphenyl)thiazol-2-yl)-3-methyl-benzyl)azetidine-3-carboxylic acid The title compound (650 mg) was obtained from 4-bromo-3-methylbenzaldehyde (3 g), by the similar method of the Example 8(1), Example 1(2), Example 1(3), Example 1(4), and Example 2.

MS (ESI) m/z: 423 (M+H)$^+$

NMR (DMSO-d$_6$) δ: 1.28 (6H, d, J=6.0 Hz), 2.59 (3H, s), 3.50 (1H, quin, J=8.2 Hz), 3.83-3.90 (2H, m), 3.91-3.98 (2H, m), 4.14 (2H, s), 4.64-4.71 (1H, m), 7.00 (2H, d, J=8.8 Hz), 7.40 (1H, d, J=8.0 Hz), 7.44 (1H, s), 7.62 (2H, d, J=8.7 Hz), 7.79 (1H, d, J=8.0 Hz), 8.12 (1H, s)

Example 22

1-(2-fluoro-4-(5-(4-isopropoxyphenyl)thiazol-2-yl)benzyl)azetidine-3-carboxylic acid The title compound (650 mg) was obtained from 4-bromo-2-fluorobenzaldehyde (3 g), by the similar method of the Example 8(1), Example 1(2), Example 1(3), Example 1(4), and Example 2.

MS (ESI) m/z: 427 (M+H)$^+$

NMR (DMSO-d$_6$) δ: 1.27 (6H, d, J=6.0 Hz), 3.18-3.27 (1H, m), 3.25 (2H, d, J=4.6 Hz), 3.43 (2H, d, J=7.1 Hz), 3.61 (2H, s), 4.63-4.71 (1H, m), 7.00 (2H, d, J=8.8 Hz), 7.48 (1H, t, J=7.7 Hz), 7.62 (2H, d, J=8.7 Hz), 7.69 (1H, dd, J=10.8 Hz), 7.72 (1H, dd, J=7.9, 1.5 Hz), 8.19 (1H, s)

Example 23

1-(2-chloro-4-(5-(4-isopropoxyphenyl)thiazol-2-yl)benzyl)azetidine-3-carboxylic acid The title compound (450 mg) was obtained from the compound obtained in the Example 19(1) (1.5 g), by the similar method of the Example 1(3), Example 1(4), and Example 2.

MS (ESI) m/z: 443 (M+H)$^+$

NMR (DMSO-d$_6$) δ: 1.28 (6H, d, J=6.0 Hz), 3.21-3.27 (1H, m), 3.29 (2H, t, J=6.5 Hz), 3.48 (2H, t, J=7.2 Hz), 3.67 (2H, s), 4.63-4.71 (1H, m), 6.99 (2H, d, J=8.8 Hz), 7.54 (1H, d, J=8.0 Hz), 7.61 (2H, d, J=8.8 Hz), 7.86 (1H, dd, J=8.0, 1.7 Hz), 7.93 (1H, d, J=1.7 Hz), 8.20 (1H, s)

Example 24

1-(2-cyclopropyl-4-(5-(4-isopropoxyphenyl)thiazol-2-yl)benzyl)azetidine-3-carboxylic acid The title compound (36.5 mg) was obtained from the compound obtained in the Example 19(2) (100 mg) as a colorless solid by the similar method of the Example 14(1), Example 13(3), Example 1(4), and Example 2.

MS (ESI) m/z: 449 (M+H)$^+$

NMR (DMSO-d$_6$) δ: 0.65-0.69 (2H, m), 0.95-0.99 (2H, m), 1.28 (6H, d, J=6.0 Hz), 2.06-2.12 (1H, m), 3.19-3.24 (1H, m), 3.25-3.27 (2H, m), 3.42-3.45 (2H, m), 3.75 (2H, s), 4.63-4.71 (1H, m), 6.99 (2H, d, J=8.8 Hz), 7.38 (1H, d, J=8.0 Hz), 7.47 (1H, d, J=1.7 Hz), 7.61 (2H, d, J=8.8 Hz), 7.68 (1H, dd, J=7.8, 1.7 Hz), 8.13 (1H, s)

Example 25

1-(4-(5-(4-isopropoxyphenyl)thiazol-2-yl)-2-methyl-benzyl)azetidine-3-carboxylic acid The title compound (350 mg) was obtained from 4-bromo-2-methylbenzaldehyde (2.3 g), by the similar method of the Example 8(1), Example 1(2), Example 1(3), Example 1(4), and Example 2.

MS (ESI) m/z: 423 (M+H)$^+$

NMR (DMSO-d$_6$) δ: 1.28 (6H, d, J=6.0 Hz), 2.33 (3H, s), 3.19-3.24 (3H, m), 3.39-3.45 (2H, m), 3.57 (2H, s), 4.63-4.70 (1H, m), 6.99 (2H, d, J=8.8 Hz), 7.35 (1H, d, J=7.8 Hz), 7.60 (2H, d, J=8.8 Hz), 7.70 (1H, dd, J=7.9, 1.7 Hz), 7.72 (1H, s), 8.14 (1H, s)

Example 26

1-(4-(5-(4-isopropoxyphenyl)thiazol-2-yl)-2-methoxybenzyl)azetidine-3-carboxylic acid The title compound (700 mg) was obtained from 4-bromo-2-methoxybenzaldehyde (2 g), by the similar method of the Example 8(1), Example 1(2), Example 1(3), Example 1(4), and Example 2.

MS (ESI) m/z: 439 (M+H)$^+$

NMR (DMSO-d$_6$) δ: 1.27 (6H, d, J=5.9 Hz), 3.41 (1H, quin, J=7.8 Hz), 3.65-3.73 (2H, m), 3.76-3.84 (2H, m), 3.91 (3H, s), 3.97 (2H, s), 4.63-4.70 (1H, m), 6.99 (2H, d, J=8.6 Hz), 7.45 (1H, d, J=7.7 Hz), 7.50 (1H, d, J=7.9 Hz), 7.53 (1H, s), 7.62 (2H, d, J=8.6 Hz), 8.18 (1H, s)

Example 27

1-(4-(5-(4-isopropoxyphenyl)thiazol-2-yl)-2-(trifluoromethyl)benzyl)azetidine-3-carboxylic acid The title compound (310 mg) was obtained from 4-bromo-2-(trifluoromethyl)benzaldehyde (1.5 g), by the similar method of the Example 8(1), Example 1(2), Example 1(3), Example 1(4), and Example 2.

MS (ESI) m/z: 477 (M+H)$^+$

NMR (DMSO-d$_6$) δ: 1.28 (6H, d, J=6.1 Hz), 3.29-3.36 (1H, m), 3.42-3.48 (2H, brs), 3.59-3.66 (2H, brs), 3.88-3.95 (2H, brs), 4.62-4.71 (1H, m), 7.00 (2H, d, J=8.8 Hz), 7.64 (2H, d, J=8.8 Hz), 7.82 (1H, d, J=8.0 Hz), 8.17 (1H, d, J=8.6 Hz), 8.19 (1H, s), 8.23 (1H, s)

Example 28

1-(4-(5-(4-isopropoxyphenyl)thiazol-2-yl)benzyl)azetidine-3-carboxamide

The compound obtained in the Example 1 (150 mg) was suspended in DMF (30 ml), and 1-hydroxybenzotriazole (74.4 mg), 1-(dimethylaminopropyl)-3-ethylcarbodiimide (106 mg), and a 2 M-ammonia/ethanol solution (0.92 ml) was added to the suspension at room temperature. After the mixture was stirred overnight, chloroform and saturated sodium bicarbonate aqueous solution were added to terminate the reaction. After the aqueous layer was extracted with chloroform twice, the combined organic layer was washed with saturated brine. After the organic layer was dried over anhydrous magnesium sulfate, the solvent was evaporated under reduced pressure. The resulting residue was purified on column chromatography (MeOH:CHCl$_3$=1:10) to obtain the title compound (128 mg) as a pale yellow solid.

MS (ESI) m/z: 408 (M+H)$^+$

Example 29

1-(4-(5-(4-isopropoxyphenyl)thiazol-2-yl)benzyl)-N-methylazetidine-3-carboxamide The title compound (154 mg) was obtained by the reaction of the compound obtained in the Example 1 (150 mg) and 40% methylamine/methanol solution (0.187 ml) as a pale yellow solid by the similar method of the Example 28.
MS (ESI) m/z: 422 (M+H)$^+$

Example 30

1-(4-(5-(4-isopropoxyphenyl)thiazol-2-yl)benzyl)-N,N-dimethylazetidine-3-carboxamide The title compound (151 mg) was obtained by the reaction of the compound obtained in the Example 1 (150 mg) and 50% dimethylamine/aqueous solution (0.191 ml) as a pale yellow solid by the similar method of the Example 28.
MS (ESI) m/z: 436 (M+H)$^+$
NMR (CDCl$_3$) δ: 1.37 (6H, d, J=6.1 Hz), 2.89 (3H, s), 2.95 (3H, s), 3.33-3.37 (2H, m), 3.53 (1H, quin., J=7.8 Hz), 3.59-3.64 (2H, m), 3.66 (2H, s), 4.55-4.63 (1H, m), 6.93 (2H, d, J=8.8 Hz), 7.36 (2H, d, J=8.0 Hz), 7.51 (2H, d, J=8.8 Hz), 7.89 (1H, s), 7.90 (2H, d, J=8.0 Hz)

Example 31

1-(4-(5-(4-ethoxyphenyl)thiazol-2-yl)benzyl)azetidine-3-carboxylic acid

The title compound (250 mg) was obtained by the reaction of the compound obtained in the Example 1(2) (800 mg) and 4-ethoxyphenylboronic acid (545 mg) as a pale yellow solid by the similar method of the Example 1(3), Example 1(4), and Example 2.
MS (ESI) m/z: 395 (M+H)$^+$
NMR (DMSO-d$_6$) δ: 1.35 (3H, t, J=7.0 Hz), 3.19-3.25 (3H, m), 3.38-3.44 (2H, m), 3.58 (2H, s), 4.07 (2H, q, J=7.0 Hz), 7.00 (2H, d, J=8.7 Hz), 7.39 (2H, d, J=8.1 Hz), 7.62 (2H, d, J=8.7 Hz), 7.87 (2H, d, J=8.1 Hz), 8.16 (1H, s)

Example 32

1-(4-(5-(4-phenoxyphenyl)thiazol-2-yl)benzyl)azetidine-3-carboxylic acid

The title compound (250 mg) was obtained by the reaction of the compound obtained in the Example 1(2) (600 mg) and 4-phenoxyphenylboronic acid (527 mg) as a pale yellow solid by the similar method of the Example 1(3), Example 1(4), and Example 2.
MS (ESI) m/z: 443 (M+H)$^+$

Example 33

1-(4-(5-(4-tert-butylphenyl)thiazol-2-yl)benzyl)azetidine-3-carboxylic acid

The title compound (170 mg) was obtained by the reaction of the compound obtained in the Example 1(2) (620 mg) and 4-tert-butylphenylboronic acid (453 mg) as a pale yellow solid by the similar method of the Example 1(3), Example 1(4), and Example 2.
MS (ESI) m/z: 407 (M+H)$^+$
NMR (DMSO-d$_6$) δ: 1.30 (9H, s), 3.60 (1H, quin, J=8.5 Hz), 4.05-4.15 (4H, m), 4.37 (2H, s), 7.48 (2H, d, J=8.5 Hz), 7.62-7.66 (4H, m), 8.01 (2H, d, J=8.5 Hz), 8.29 (1H, s)

Example 34

1-(4-(5-(4-cyclopentylphenyl)thiazol-2-yl)benzyl)azetidine-3-carboxylic acid

The title compound (174 mg) was obtained by the reaction of the compound obtained in the Example 1(2) (470 mg) and 4-cyclopentylphenylboronic acid (440 mg) as a pale yellow solid by the similar method of the Example 1(3), Example 1(4), and Example 2.
MS (ESI) m/z: 419 (M+H)$^+$
NMR (DMSO-d$_6$) δ: 1.50-1.58 (2H, m), 1.61-1.69 (2H, m), 1.73-1.82 (2H, m), 1.98-2.07 (2H, m), 2.97-3.05 (1H, m), 3.52-3.59 (1H, m), 3.95-4.08 (4H, m), 4.28 (2H, s), 7.34 (2H, d, J=8.2 Hz), 7.58-7.64 (4H, m), 7.99 (2H, d, J=8.2 Hz), 8.29 (1H, s)

Example 35

1-(4-(5-(4-hexylphenyl)thiazol-2-yl)benzyl)azetidine-3-carboxylic acid

The title compound (210 mg) was obtained by the reaction of the compound obtained in the Example 1(2) (500 mg) and 4-hexylphenylboronic acid (440 mg) as a pale yellow solid by the similar method of the Example 1(3), Example 1(4), and Example 2.
MS (ESI) m/z: 435 (M+H)$^+$

Example 36

1-(4-(5-(4-cyclohexylphenyl)thiazol-2-yl)benzyl)azetidine-3-carboxylic acid

The title compound (178 mg) was obtained by the reaction of the compound obtained in the Example 1(2) (530 mg) and 4-cyclohexylphenylboronic acid (470 mg) as a pale yellow solid by the similar method of the Example 1(3), Example 1(4), and Example 2.
MS (ESI) m/z: 433 (M+H)$^+$
NMR (DMSO-d$_6$) δ: 1.20-1.47 (5H, m), 1.68-1.84 (5H, m), 2.51-2.55 (1H, m), 3.18-3.43 (5H, m), 3.59 (2H, s), 7.30 (2H, d, J=8.2 Hz), 7.39 (2H, d, J=8.1 Hz), 7.61 (2H, d, J=8.1 Hz), 7.88 (2H, d, J=8.1 Hz), 8.24 (1H, s)

Example 37

1-(4-(5-(3-chloro-4-isopropoxyphenyl)thiazol-2-yl)-3-methylbenzyl)azetidine-3-carboxylic acid The title compound (350 mg) was obtained from 4-bromo-3-methylbenzaldehyde (2 g), by the similar method of the Example 8(1), Example 1(2), Example 11(3), Example 1(4), and Example 2.
MS (ESI) m/z: 457 (M+H)$^+$
NMR (DMSO-d$_6$) δ: 1.31 (6H, d, J=6.0 Hz), 2.57 (3H, s), 3.19-3.28 (3H, m), 3.42-3.47 (2H, m), 3.61 (2H, s), 4.69-4.77

(1H, m), 7.21-7.28 (3H, m), 7.59 (1H, dd, J=8.6, 2.4 Hz), 7.72 (1H, d, J=7.9 Hz), 7.82 (1H, d, J=7.9 Hz), 8.29 (1H, s)

Example 38

1-(4-(5-(4-propoxyphenyl)thiazol-2-yl-benzyl)azetidine-3-carboxylic acid

The title compound (190 mg) was obtained by the reaction of the compound obtained in the Example 1(2) (500 mg) and 4-propoxyphenylboronic acid (369 mg) as a pale yellow solid by the similar method of the Example 1(3), Example 1(4), and Example 2.
MS (ESI) m/z: 409 (M+H)$^+$
NMR (DMSO-d$_5$) δ: 0.98 (3H, t, J=7.4 Hz), 1.70-1.78 (2H, m), 3.46-3.51 (1H, m), 3.78-3.95 (4H, m), 3.97 (2H, t, J=6.5 Hz), 4.10-4.17 (2H, brs), 7.02 (2H, d, J=8.8 Hz), 7.54 (2H, d, J=8.1 Hz), 7.63 (2H, d, J=8.8 Hz), 7.95 (2H, d, J=8.1 Hz), 8.20 (1H, s)

Example 39

1-(4-(5-(4-butoxyphenyl)thiazol-2-yl)benzyl)azetidine-3-carboxylic acid

The title compound (205 mg) was obtained by the reaction of the compound obtained in the Example 1(2) (500 mg) and 4-butoxyphenylboronic acid (398 mg) as a pale yellow solid by the similar method of the Example 1(3), Example 1(4), and Example 2.
MS (ESI) m/z: 423 (M+H)$^+$ Example 40

1-(4-(5-(4-pentyloxyphenyl)thiazol-2-yl)benzyl)azetidine-3-carboxylic acid

The title compound (198 mg) was obtained by the reaction of the compound obtained in the Example 1(2) (500 mg) and 4-pentyloxyphenylboronic acid (405 mg) as a pale yellow solid by the similar method of the Example 1(3), Example 1(4), and Example 2.
MS (ESI) m/z: 437 (M+H)$^+$ Example 41

1-(4-(5-(4-(cyclopentyloxy)phenyl)thiazol-2-yl)benzyl)azetidine-3-carboxylic acid The title compound (220 mg) was obtained by the reaction of the compound obtained in the Example 1(2) (490 mg) and 4-cyclopentyloxyphenylboronic acid (408 mg) as a pale yellow solid by the similar method of the Example 1(3), Example 1(4), and Example 2.
MS (ESI) m/z: 435 (M+H)$^+$
NMR (DMSO-d$_6$) δ: 1.55-1.63 (2H, m), 1.66-1.75 (4H, m), 1.88-1.97 (2H, m), 3.19-3.52 (7H, m), 4.84-4.89 (1H, m), 6.98 (2H, d, J=8.8 Hz), 7.41 (2H, d, J=8.2 Hz), 7.61 (2H, d, J=8.8 Hz), 7.88 (2H, d, J=8.2 Hz), 8.16 (1H, s)

Example 42

1-(4-(5-(4-hexyloxyphenyl)thiazol-2-yl)benzyl)azetidine-3-carboxylic acid

The title compound (161 mg) was obtained by the reaction of the compound obtained in the Example 1(2) (390 mg) and 4-hexyloxyphenylboronic acid (351 mg) as a pale yellow solid by the similar method of the Example 1(3), Example 1(4), and Example 2.
MS (ESI) m/z: 451 (M+H)$^+$ Example 43

1-(4-(5-(4-(cyclohexyloxy)phenyl)thiazol-2-yl)benzyl)azetidine-3-carboxylic acid The title compound (165 mg) was obtained by the reaction of the compound obtained in the Example 1(2) (440 mg) and 4-cyclohexyloxyphenylboronic acid (390 mg) as a pale yellow solid by the similar method of the Example 1(3), Example 1(4), and Example 2.
MS (ESI) m/z: 449 (M+H)$^+$
NMR (DMSO-d$_6$) δ: 0.78-0.87 (2H, m), 1.18-1.96 (8H, m), 3.13-3.84 (7H, m), 4.37-4.44 (1H, m), 7.02 (2H, d, J=8.7 Hz), 7.44 (2H, d, J=7.7 Hz), 7.61 (2H, d, J=8.7 Hz), 7.91 (2H, d, J=8.0 Hz), 8.17 (1H, s)

Example 44

1-(4-(5-(4-benzyloxyphenyl)thiazol-2-yl)benzyl)azetidine-3-carboxylic acid

The title compound (165 mg) was obtained by the reaction of the compound obtained in the Example 1(2) (450 mg) and 4-benzyloxyphenylboronic acid (404 mg) as a pale yellow solid by the similar method of the Example 1(3), Example 1(4), and Example 2.
MS (ESI) m/z: 457 (M+H)$^+$ Example 45

1-(4-(5-(4-propylphenyl)thiazol-2-yl)benzyl)azetidine-3-carboxylic acid

The title compound (193 mg) was obtained by the reaction of the compound obtained in the Example 1(2) (500 mg) and 4-propylphenylboronic acid (336 mg) as a pale yellow solid by the similar method of the Example 1(3), Example 1(4), and Example 2.
MS (ESI) m/z: 393 (M+H)$^+$ Example 46

1-(4-(5-(4-isopropylphenyl)thiazol-2-yl)benzyl)azetidine-3-carboxylic acid

The title compound (202 mg) was obtained by the reaction of the compound obtained in the Example 1(2) (480 mg) and 4-isopropylphenylboronic acid (331 mg) as a pale yellow solid by the similar method of the Example 1(3), Example 1(4), and Example 2.
MS (ESI) m/z: 393 (M+H)$^+$
NMR (DMSO-d$_6$) δ: 1.22 (6H, d, J=6.9 Hz), 2.48-2.50 (1H, m), 3.55-3.63 (1H, m), 4.05-4.17 (4H, m), 4.37 (1H, s), 7.34 (2H, d, J=8.2 Hz), 7.62 (2H, d, J=8.4 Hz), 7.65 (2H, d, J=8.3 Hz), 8.01 (2H, d, J=8.3 Hz), 8.29 (1H, s)

Example 47

1-(4-(5-(4-butylphenyl)thiazol-2-yl)benzyl)azetidine-3-carboxylic acid

The title compound (211 mg) was obtained by the reaction of the compound obtained in the Example 1(2) (500 mg) and 4-butylphenylboronic acid (365 mg) as a pale yellow solid by the similar method of the Example 1(3), Example 1(4), and Example 2.
MS (ESI) m/z: 407 (M+H)⁺

Example 48

1-(4-(5-(4-isobutylphenyl)thiazol-2-yl)benzyl)azetidine-3-carboxylic acid

The title compound (197 mg) was obtained by the reaction of the compound obtained in the Example 1(2) (550 mg) and 4-isobutylphenylboronic acid (405 mg) as a pale yellow solid by the similar method of the Example 1(3), Example 1(4), and Example 2.
MS (ESI) m/z: 407 (M+H)⁺
NMR (DMSO-$d_6$) δ: 0.87 (6H, d, J=6.6 Hz), 1.81-1.90 (1H, m), 2.47 (2H, s), 3.49-3.57 (1H, m), 3.90-4.04 (4H, m), 4.23 (2H, s), 7.26 (2H, d, J=8.2 Hz), 7.58 (2H, d, J=8.1 Hz), 7.63 (2H, d, J=8.2 Hz), 7.99 (2H, d, J=8.3 Hz), 8.29 (1H, s)

Example 49

1-(4-(5-(4-pentylphenyl)thiazol-2-yl)benzyl)azetidine-3-carboxylic acid

The title compound (203 mg) was obtained by the reaction of the compound obtained in the Example 1(2) (500 mg) and 4-pentylphenylboronic acid (411 mg) as a pale yellow solid by the similar method of the Example 1(3), Example 1(4), and Example 2.
MS (ESI) m/z: 421 (M+H)⁺

Example 50

1-(4-(5-(3-cyano-4-isopropoxyphenyl)thiazol-2-yl)benzyl)azetidine-3-carboxylic acid (1) 2-isopropoxy-5-(4,4,5,5-tetramethyl-1,3,2-dioxaborolan-2-yl)benzonitrile The title compound (1.98 g) was obtained from 5-bromo-2-hydroxybenzonitrile (2 g), by the method disclosed in the patent (WO2011/134280).

(2) 1-(4-(5-(3-cyano-4-isopropoxyphenyl)thiazol-2-yl)benzyl)azetidine-3-carboxylic acid The title compound (153 mg) was obtained by the reaction of the compound obtained in the Example 1(2) (200 mg) and the compound obtained in the Example 50(1) (321 mg) as a light brown solid by the similar method of the Example 1(3), Example 1(4), and Example 2.
MS (ESI) m/z: 434 (M+H)⁺
NMR (DMSO-$d_6$) δ: 1.34 (6H, d, J=6.0 Hz), 3.21-3.30 (1H, m), 3.30-3.38 (2H, m), 3.45-3.52 (2H, m), 3.68 (2H, s), 4.82-4.90 (1H, m), 7.37 (1H, d, J=9.2 Hz), 7.42 (2H, d, J=8.2 Hz), 7.89 (2H, d, J=8.3 Hz), 7.92 (1H, dd, J=8.9, 2.4 Hz), 8.14 (1H, d, J=2.5 Hz), 8.31 (1H, s)

Example 51

1-(4-(5-(4-cyclobutoxyphenyl)thiazol-2-yl)benzyl)azetidine-3-carboxylic acid

The title compound (184 mg) was obtained by the reaction of the compound obtained in the Example 1(2) (480 mg) and 4-cyclobutoxyphenylboronic acid (318 mg) as a pale yellow solid by the similar method of the Example 1(3), Example 1(4), and Example 2.
MS (ESI) m/z: 421 (M+H)⁺
NMR (DMSO-$d_6$) δ: 1.60-1.70 (1H, m), 1.75-1.84 (1H, m), 1.99-2.09 (2H, m), 2.39-2.48 (2H, m), 3.22-3.48 (2H, m), 3.72-3.90 (3H, m), 4.08 (2H, s), 4.70-4.77 (1H, m), 6.93 (2H, d, J=8.7 Hz), 7.52 (2H, d, J=7.8 Hz), 7.62 (2H, d, J=8.6 Hz), 7.95 (2H, d, J=8.0 Hz), 8.18 (1H, s)

Example 52

1-(4-(5-(4-isopropoxy-3-methylphenyl)thiazol-2-yl)benzyl)azetidine-3-carboxylic acid The title compound (184 mg) was obtained by the reaction of the compound obtained in the Example 1(2) (460 mg) and 4-isopropoxy-3-methylphenylboronic acid (366 mg) as a pale yellow solid by the similar method of the Example 1(3), Example 1(4), and Example 2.
MS (ESI) m/z: 423 (M+H)⁺
NMR (DMSO-$d_6$) δ: 1.28 (6H, J=6.0 Hz), 2.17 (3H, s), 3.27-3.34 (1H, m), 3.41-3.47 (2H, m), 3.56-3.62 (2H, m), 3.79 (2H, s), 3.59-4.66 (1H, m), 7.01 (1H, d, J=8.7 Hz), 7.42-7.51 (4H, m), 7.89 (2H, d, J=8.3 Hz), 8.14 (1H, s)

Example 53

1-(4-(5-(3-fluoro-4-isopropoxyphenyl)thiazol-2-yl)benzyl)azetidine-3-carboxylic acid The title compound (210 mg) was obtained by the reaction of the compound obtained in the Example 1(2) (500 mg) and 4-isopropoxy-3-fluorophenylboronic acid (406 mg) as a pale yellow solid by the similar method of the Example 1(3), Example 1(4), and Example 2.
MS (ESI) m/z: 427 (M+H)⁺
NMR (DMSO-$d_6$) δ: 1.29 (6H, J=6.0 Hz), 3.05-3.11 (1H, m), 3.14-3.18 (2H, m), 3.34-3.38 (2H, m), 3.57 (2H, s), 4.66-4.72 (1H, m), 7.25 (1H, t, J=8.8 Hz), 7.38 (2H, d, J=8.2 Hz), 7.42 (1H, dd, J=8.4, 2.2 Hz), 7.65 (1H, dd, J=12.3 Hz, 2.2 Hz), 7.86 (2H, d, J=8.2 Hz), 8.24 (1H, s)

Example 54

1-(4-(5-(4-isopropoxy-2-methylphenyl)thiazol-2-yl)benzyl)azetidine-3-carboxylic acid The title compound (199 mg) was obtained by the reaction of the compound obtained in the Example 1(2) (500 mg) and (4-isopropoxy-2-methylphenyl)boronic acid (398 mg) as a pale yellow solid by the similar method of the Example 1(3), Example 1(4), and Example 2.
MS (ESI) m/z: 423 (M+H)⁺
NMR (DMSO-$d_6$) δ: 1.27 (6H, J=6.0 Hz), 2.38 (3H, s), 3.48-3.56 (1H, m), 3.88-4.02 (4H, m), 4.22 (2H, s), 4.62-4.69 (1H, m), 6.84 (1H, dd, J=8.5, 2.6 Hz), 6.91 (1H, d, J=2.4 Hz), 7.37 (1H, d, J=8.5 Hz), 7.58 (2H, d, J=8.2 Hz), 7.91 (1H, s), 7.98 (2H, d, J=8.3 Hz)

Example 55

1-(4-(5-(4-isopropoxy-2-(trifluoromethyl)phenyl)thiazol-2-yl)benzyl)azetidine-3-carboxylic acid The title compound (222 mg) was obtained by the reaction of the compound obtained in the Example 1(2) (515 mg) and 4-isopropoxy-2-(trifluoromethyl)phenylboronic acid (476 mg) as a pale yellow solid by the similar method of the Example 1(3), Example 1(4), and Example 2.

MS (ESI) m/z: 477 (M+H)+

NMR (DMSO-d$_6$) δ: 1.31 (6H, J=6.0 Hz), 3.54-3.62 (1H, m), 3.98-4.11 (4H, m), 4.34 (2H, s), 4.77-4.85 (1H, m), 7.31-7.35 (2H, m), 7.57 (1H, d, J=9.2 Hz), 7.64 (2H, d, J=8.2 Hz), 7.85 (1H, s), 8.00 (2H, d, J=8.2 Hz)

Example 56

1-(4-(5-(4-isopropoxy-3-(trifluoromethyl)phenyl)thiazol-2-yl)benzyl)azetidine-3-carboxylic acid The title compound (222 mg) was obtained by the reaction of the compound obtained in the Example 1(2) (511 mg) and 4-isopropoxy-3-(trifluoromethyl)phenylboronic acid (472 mg) as a pale yellow solid by the similar method of the Example 1(3), Example 1(4), and Example 2.

MS (ESI) m/z: 477 (M+H)+

NMR (DMSO-d$_6$) δ: 1.30 (6H, J=6.1 Hz), 3.29-3.37 (1H, m), 3.45-3.53 (2H, m), 3.60-3.66 (2H, m), 3.84 (2H, s), 4.81-4.89 (1H, m), 7.39 (1H, d, J=8.9 Hz), 7.47 (2H, d, J=8.2 Hz), 7.86-7.87 (1H, m), 7.89-7.95 (3H, m), 8.33 (1H, s)

Example 57

1-(4-(5-(3-chloro-4-isopropoxyphenyl)thiazol-2-yl)-2-fluorobenzyl)azetidine-3-carboxylic acid The title compound (780 mg) was obtained from 4-bromo-2-fluorobenzaldehyde (2.1 g), by the similar method of the Example 8(1), Example 1(2) Example 3(1), Example 1(4), and Example 2.

MS (ESI) m/z: 461 (M+H)+

NMR (DMSO-d$_6$) δ: 1.31 (6H, J=6.0 Hz), 3.17-3.27 (3H, m), 3.43-3.47 (2H, m), 3.61 (2H, s), 4.71-4.77 (1H, m), 7.26 (1H, d, J=8.9 Hz), 7.50 (1H, t, J=7.7 Hz), 7.59 (1H, dd, J=8.6, 2.3 Hz), 7.67-7.74 (2H, m), 7.82 (1H, d, J=2.3 Hz), 8.29 (1H, s)

Example 58

1-(4-(5-(3-chloro-4-isopropoxyphenyl)thiazol-2-yl)-2-(trifluoromethyl)benzyl)azetidine-3-carboxylic acid The title compound (373 mg) was obtained from 4-bromo-2-(trifluoromethyl)benzaldehyde (1.6 g), by the similar method of the Example 8(1), Example 1(2), Example 3(1), Example 1(4), and Example 2.

MS (ESI) m/z: 511 (M+H)+

NMR (DMSO-d$_6$) δ: 1.31 (6H, J=6.0 Hz), 3.23-3.37 (1H, m), 3.39-3.47 (2H, m), 3.56-3.64 (2H, m), 3.89 (2H, s), 4.69-4.77 (1H, m), 7.25 (1H, d, J=8.8 Hz), 7.61 (1H, dd, J=8.6 Hz), 7.82 (1H, d, J=8.0 Hz), 7.85 (1H, d, J=2.2 Hz), 8.17-8.19 (2H, m), 7.89 (2H, d, J=8.3 Hz), 8.34 (1H, s)

Example 59

1-(4-(5-(3-cyano-4-isobutylphenyl)thiazol-2-yl)-3-fluorobenzyl)azetidine-3-carboxylic acid (1) 2-isobutyl-5-nitrobenzonitrile Under an argon gas atmosphere, 2-bromo-5-nitrobenzonitrile (2.0 g), isobutylboronic acid (988 mg), cesium carbonate (5.7 g), and PdCl$_2$ (dppf)-CH$_2$Cl$_2$ (720 mg) were dissolved in toluene (25 ml) and water (1 ml). The mixture was stirred at 100° C. for 18 hours. After the mixture was cooled to room temperature, the mixture was diluted with diethyl ether and water followed by the step of extraction/separation. The organic layer was washed with 1 N-hydrochloric acid, 5 N-sodium hydroxide aqueous solution and saturated brine, and dried over anhydrous magnesium sulfate. After the solvent was evaporated under reduced pressure, the resulting residue was purified on column chromatography (EtOAc:hexane=1:3) to obtain the title compound (1.06 g) as a pale yellow oily substance.

(2) 5-amino-2-isobutylbenzonitrile

Under an argon gas atmosphere, the compound obtained in the Example 59(1) (500 mg) was dissolved in the mixed solution of ethanol (5 ml) and ethyl acetate (5 ml), and Pt/C (sulfided) (50 mg) was added to the mixture. The atmosphere was substituted with hydrogen, and the mixture was stirred at room temperature for 6 hours. After filtration of the reaction solution on Celite, the resulting filtrate was removed under reduced pressure to obtain the target compound (447 mg) as a pale black oily substance or solid.

(3) 5-bromo-2-isobutylbenzonitrile

The compound obtained in the Example 59(2) (447 mg) was dissolved in acetonitrile (7 ml), and 48% hydrobromic acid (0.32 ml) was added to the solution under ice cooling. Subsequently, sodium nitrite aqueous solution (213 mg of NaNO$_2$ was dissolved in 0.7 ml of water) prepared separately was added, and the resulting mixture was stirred at the same temperature for 30 minutes. After adding CuBr (74 mg) and CuBr$_2$ (1.15 g), the mixture was warmed to room temperature and was further stirred overnight. After the addition of diethyl ether and saturated sodium bicarbonate aqueous solution to the reaction solution, the resulting solution was extracted/separated. The resulting organic layer was washed with saturated brine. The solvent was evaporated under reduced pressure to obtain the title compound (579 mg) as a colorless oily substance.

(4) 2-isobutyl-5-(4,4,5,5-tetramethyl-1,3,2-dioxaborolan-2-yl)benzonitrile

The compound obtained in the Example 59(3) (579 mg) was dissolved in dioxane (8 ml) under an argon gas atmosphere, and bis(pinacolato)diborane (926 mg), potassium acetate (715 mg), and PdCl$_2$ (dppf)-CH$_2$Cl$_2$ (199 mg) were added to the solution. The mixture was stirred at 85° C. for 11 hours. The end point of the reaction was confirmed on TLC (ethyl acetate:n-hexane=1:5), and the mixture was diluted with diisopropyl ether and water followed by the step of extraction/separation. The resulting organic layer was washed with saturated brine, and the solvent was evaporated under reduced pressure. The resulting residue was purified on column chromatography (ethyl acetate:n-hexane=1:5) to obtain the title compound (500 mg) as a colorless oily substance with high viscosity.

(5) 1-(4-(5-(3-cyano-4-isobutylphenyl)thiazol-2-yl)-3-fluorobenzyl)azetidine-3-carboxylic acid The title compound (96 mg) was obtained by the reaction of the compound obtained in the Example 11(1) (100 mg) and the compound obtained in the Example 59(4) (130 mg), by the similar method of the Example 1(3), Example 1(4), and Example 2.

MS (ESI) m/z: 450 (M+H)+

NMR (DMSO-$d_6$) δ: 0.91 (6H, J=6.6 Hz), 1.91-1.98 (1H, m), 2.69 (2H, d, J=7.3 Hz), 2.89-2.96 (1H, m), 3.14 (2H, t, J=7.1 Hz), 3.35 (2H, t, J=7.3 Hz), 3.58 (2H, s), 7.27 (1H, d, J=8.1 Hz), 7.31 (1H, d, J=12.6 Hz), 7.52 (1H, d, J=8.3 Hz), 7.98 (1H, dd, J=8.1, 2.0 Hz), 8.16 (1H, t, J=8.0 Hz), 8.24 (1H, d, J=2.0 Hz), 8.51 (1H, d, J=2.4 Hz)

Example 60

1-(3-chloro-4-(5-(3-chloro-4-isopropoxyphenyl)thiazol-2-yl)benzyl)azetidine-3-carboxylic acid The title compound (258 mg) was obtained from the compound obtained in the Example 12(2) (500 mg), by the similar method of the Example 3(1), Example 1(4), and Example 2.

MS (ESI) m/z: 478 (M+H)+

NMR (DMSO-$d_6$) δ: 1.31 (6H, J=6.0 Hz), 3.32-3.37 (1H, m), 3.48-3.58 (2H, brs), 3.62-3.72 (2H, brs), 3.82-3.91 (2H, brs), 4.70-4.78 (1H, m), 7.25 (1H, d, J=8.9 Hz), 7.47 (1H, d, J=8.0 Hz), 7.60-7.64 (2H, m), 7.87 (1H, d, J=2.3 Hz), 8.21 (1H, d, J=8.1 Hz), 8.38 (1H, s)

Example 61

1-(4-(5-(3-chloro-4-isopropoxyphenyl)thiazol-2-yl)-3-methoxybenzyl)azetidine-3-carboxylic acid The title compound (199 mg) was obtained from the compound obtained in the Example 18(2) (490 mg), by the similar method of the Example 3(1), Example 1(4), and Example 2.

MS (ESI) m/z: 473 (M+H)+

NMR (DMSO-$d_6$) δ: 1.31 (6H, J=6.0 Hz), 3.29-3.36 (1H, m), 3.42-3.48 (2H, m), 3.59-3.66 (2H, m), 3.80 (2H, s), 4.05 (3H, s), 4.68-4.76 (1H, m), 7.05 (1H, d, J=8.0 Hz), 7.20 (1H, s), 7.23 (1H, d, J=8.9 Hz), 7.59 (1H, dd, J=8.5, 2.3 Hz), 7.80 (1H, d, J=2.2 Hz), 8.22 (1H, d, J=8.0 Hz), 8.26 (1H, s)

Example 62

1-(4-(5-(3-chloro-4-isopropoxyphenyl)thiazol-2-yl)-2-methylbenzyl)azetidine-3-carboxylic acid The title compound (177 mg) was obtained from 4-bromo-2-methylbenzaldehyde (2.1 g), by the similar method of the Example 8(1), Example 1(2), Example 3(1), Example 1(4), and Example 2.

MS (ESI) m/z: 457 (M+H)+

NMR (DMSO-$d_6$) δ: 1.28 (6H, J=6.0 Hz), 2.38 (3H, 5), 3.36-3.43 (1H, m), 3.57-3.66 (2H, m), 3.70-3.77 (2H, m), 3.92 (2H, s), 4.69-4.76 (1H, m), 7.24 (1H, d, J=9.0 Hz), 7.44 (1H, d, J=8.0 Hz), 7.58 (1H, dd, J=8.6, 2.4 Hz), 7.74 (1H, dd, J=7.8, 1.7 Hz), 7.77 (1H, s), 7.81 (1H, d, J=2.4 Hz), 8.26 (1H, s)

Example 63

1-(2-chloro-4-(5-(3-chloro-4-isopropoxyphenyl)thiazol-2-yl)benzyl)azetidine-3-carboxylic acid The title compound (211 mg) was obtained from the compound obtained in the Example 19(1) (1.5 g), by the similar method of the Example 3(1), Example 1(4), and Example 2.

MS (ESI) m/z: 478 (M+H)+

NMR (DMSO-$d_6$) δ: 1.31 (6H, J=6.0 Hz), 3.22-3.35 (3H, m), 3.47-3.52 (2H, m), 3.69 (2H, s), 4.70-4.77 (1H, m), 7.25 (1H, d, J=8.9 Hz), 7.54 (1H, d, J=8.0 Hz), 7.59 (1H, dd, J=8.5, 2.3 Hz), 7.83 (1H, d, J=2.3 Hz), 7.86 (1H, dd, J=8.0, 1.8 Hz), 7.94 (1H, d, J=1.7 Hz), 8.30 (1H, s)

Example 64

1-(4-(5-(3-chloro-4-isopropoxyphenyl)thiazol-2-yl)-2-methoxybenzyl)azetidine-3-carboxylic acid The title compound (199 mg) was obtained from 4-bromo-2-methoxybenzaldehyde (800 mg), by the similar method of the Example 8(1), Example 1(2) Example 3(1), Example 1(4), and Example 2.

MS (ESI) m/z: 473 (M+H)+

NMR (DMSO-$d_6$) δ: 1.31 (6H, J=6.0 Hz), 3.55-3.62 (1H, m), 3.94 (3H, s), 4.07-4.17 (4H, m), 4.32 (2H, s), 4.70-4.78 (1H, m), 7.26 (1H, d, J=8.9 Hz), 7.52-7.56 (2H, m), 7.58 (1H, s), 7.61 (1H, dd, J=8.6, 2.3 Hz), 7.85 (1H, d, J=2.3 Hz), 8.32 (1H, s)

Example 65

1-(4-(5-(4-isopropoxyphenyl)thiazol-2-yl)benzyl)azetidine-3-carboxylic acid hydrochloride The compound of the Example 2 (150 mg) was dissolved in THF (45 ml) and methanol (10 ml) while warming, and 1 N-hydrochloric acid (0.4 ml) was added to the solution. The mixture was stirred for 10 minutes. The solvent was evaporated under reduced pressure, and the residue was dissolved again in methanol (5 ml). The addition of diethyl ether resulted in the precipitation of a solid. After filtration of the precipitate, the precipitate was dried under reduced pressure to obtain the title compound (144 mg) as a colorless solid.

MS (ESI) m/z: 409 (M+H)+

NMR (DMSO-$d_6$) δ: 1.28 (6H, d, J=6.1 Hz), 3.59-3.65 (1H, m), 4.11-4.19 (4H, m), 4.40-4.43 (2H, brs), 4.63-4.71 (1H, m), 7.01 (2H, d, J=9.0 Hz), 7.55 (2H, d, J=8.3 Hz), 7.62 (2H, d, J=8.8 Hz), 7.99 (2H, d, J=8.3 Hz), 8.23 (1H, s)

Example 66

1-(4-(5-(4-isopropoxyphenyl)thiazol-2-yl)benzyl)azetidine-3-carboxylic acid sulfate The compound of the Example 2 (150 mg) was dissolved in THF (40 ml) and methanol (10 ml) while warming, 1 N-sulfuric acid (0.2 ml) was added to the solution, and the mixture was stirred for 10 minutes. After the solvent was evaporated under reduced pressure, the residue was redissolved in DMF (10 ml). The addition of diethyl ether to the mixture resulted in the precipitation of a solid. The precipitate was filtered, and dried under reduced pressure to obtain the title compound (160 mg) as a yellow solid.

MS (ESI) m/z: 409 (M+H)+

NMR (DMSO-$d_6$) δ: 1.28 (6H, d, J=6.1 Hz), 3.48-3.56 (1H, m), 3.90-4.05 (4H, m), 4.19-4.24 (2H, brs), 4.64-4.71 (1H, m), 7.01 (2H, d, J=8.8 Hz), 7.60-7.66 (4H, m), 7.99 (2H, d, J=8.3 Hz), 8.23 (1H, s)

Example 67

1-(4-(5-(4-isopropoxyphenyl)thiazol-2-yl)benzyl)azetidine-3-carboxylic acid methanesulfonate The compound of the Example 2 (150 mg) was dissolved in THF (45 ml) and methanol (10 ml) while warming, and methanesulfonic acid (26 μl) was added to the solution. The mixture was stirred for 10 minutes. After the solvent was evaporated under reduced pressure, the residue was redissolved in methanol (5 ml) and ethanol (5 ml). The addition of diethyl ether resulted in the precipitation of a solid. The resulting precipitate was filtered, and dried under reduced pressure to obtain the title compound (117 mg) as a grayish white solid.

MS (ESI) m/z: 409 (M+H)$^+$

NMR (DMSO-d$_6$) δ: 1.28 (6H, d, J=6.1 Hz), 2.29 (3H, s), 3.62 (1H, quin, J=8.5 Hz), 4.14-4.25 (4H, m), 4.40-4.44 (2H, brs), 4.64-4.71 (1H, m), 7.01 (2H, d, J=8.9 Hz), 7.57-7.65 (4H, m), 8.01 (2H, d, J=8.3 Hz), 8.23 (1H, s)

Example 68

1-(4-(5-(4-isopropoxyphenyl)thiazol-2-yl)benzyl) azetidine-3-carboxylic acid acetate The compound of the Example 2 (150 mg) was dissolved in THF (45 ml) and methanol (10 ml) while warming, and acetic acid (23 μl) was added to the solution. The mixture was stirred for 10 minutes. After the solvent was evaporated under reduced pressure, the residue (slurry) was washed with ethyl acetate. After filtration of the precipitate, the precipitate was dried under reduced pressure to obtain the title compound (100 mg) as a grayish white solid.

MS (ESI) m/z: 409 (M+H)$^+$

Example 69

1-(4-(5-(4-isopropoxyphenyl)thiazol-2-yl)benzyl) azetidine-3-carboxylic acid sodium salt The compound of the Example 2 (150 mg) was dissolved in THF (45 ml) and methanol (10 ml) while warming, and 1 N-hydrochloric acid (0.4 ml) was added to the solution. The mixture was stirred for 10 minutes. After the solvent was evaporated under reduced pressure, the residue was redissolved in methanol (5 ml). The addition of diethyl ether resulted in the precipitation of a solid. The resulting precipitate was filtered, and dried under reduced pressure to obtain the title compound (105 mg) as a colorless to yellow solid.

MS (ESI) m/z: 409 (M+H)$^+$

NMR (DMSO-d$_6$) δ: 1.28 (6H, d, J=5.9 Hz), 2.74 (1H, quin, 7.4 Hz), 3.07 (2H, t, J=7.2 Hz), 3.26 (2H, t, J=7.2 Hz), 3.51 (2H, s), 4.63-4.70 (1H, m), 7.00 (2H, d, J=8.7 Hz), 7.37 (2H, d, J=7.8 Hz), 7.61 (2H, d, J=8.5 Hz), 7.85 (2H, d, J=8.3 Hz), 8.15 (1H, s)

[Compound 10]

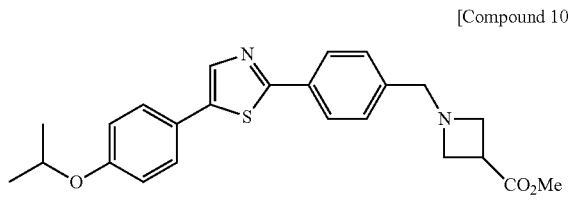

Example 1

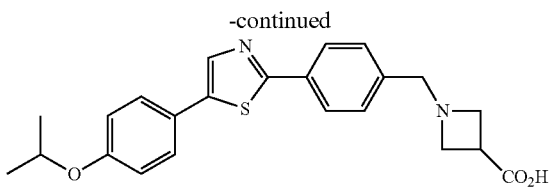

Example 2

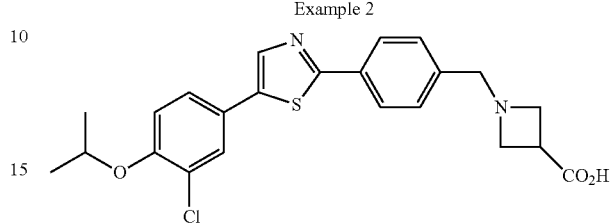

Example 3

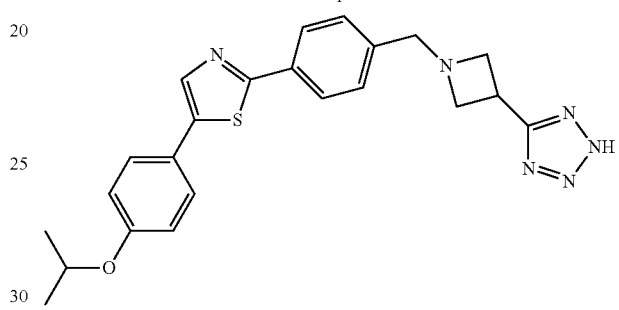

Example 4

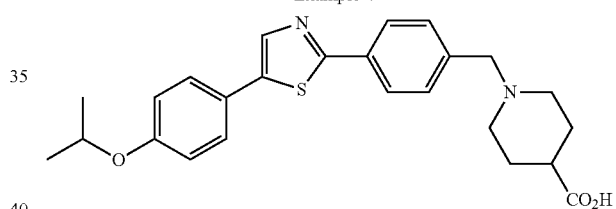

Example 5

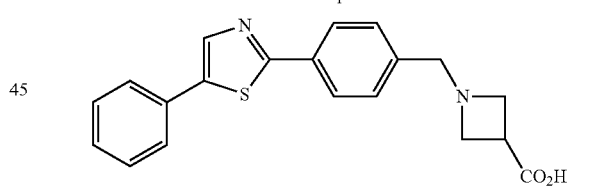

Example 6

[Compound 11]

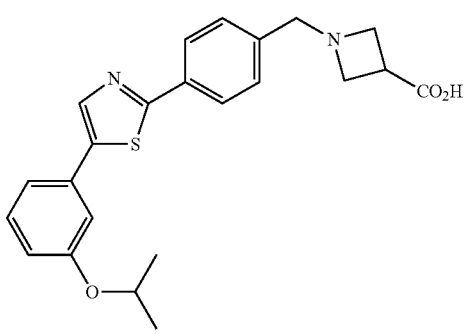

Example 7

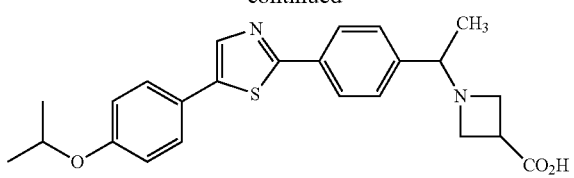
Example 8
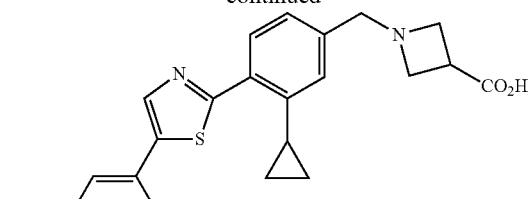
Example 14
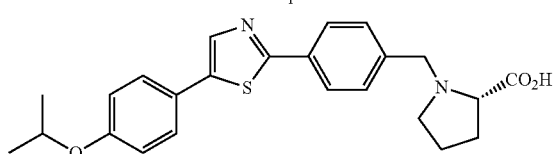
Example 9
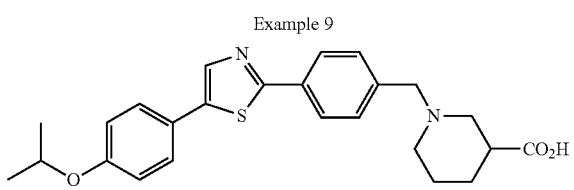
Example 10
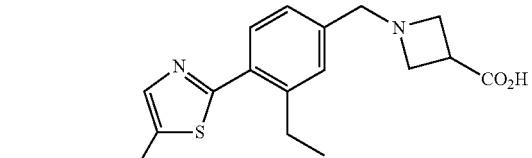
Example 15
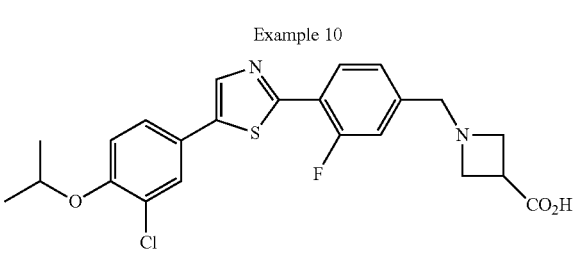
Example 11
[Compound 12]
Example 16
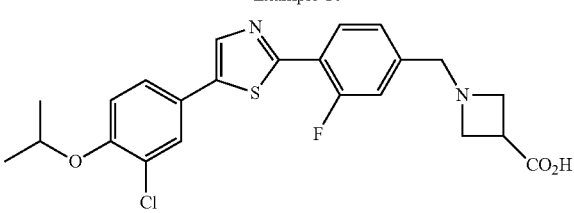
Example 12
[Compound 13]
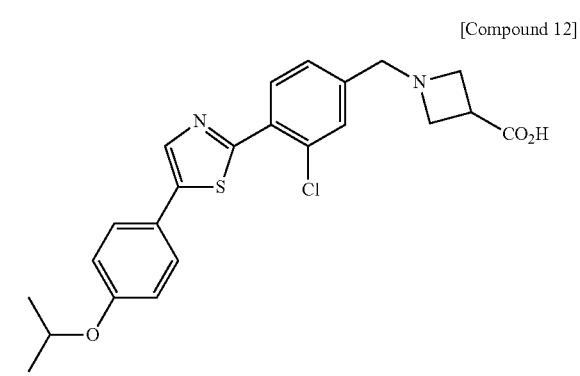
Example 13
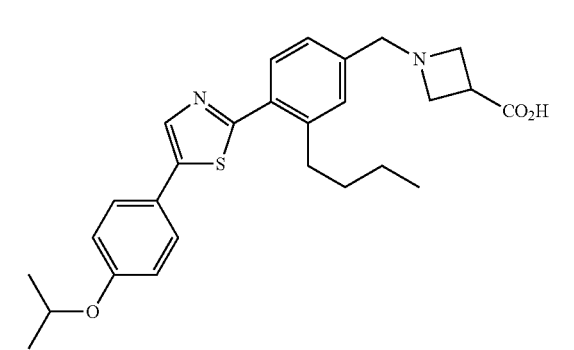
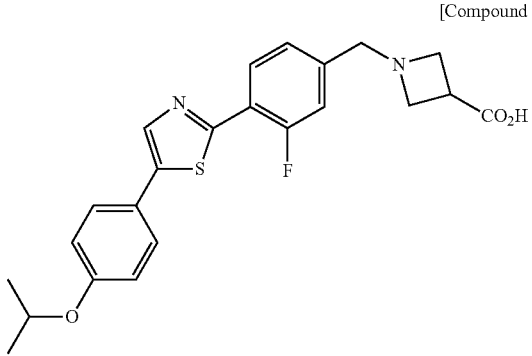
Example 17

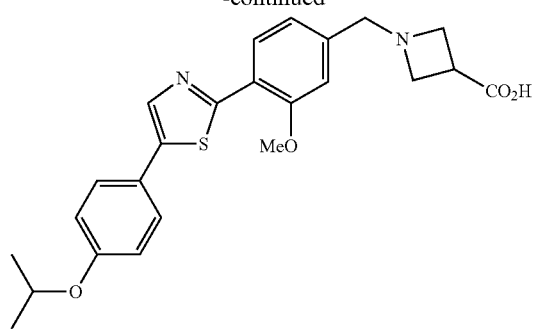
Example 18
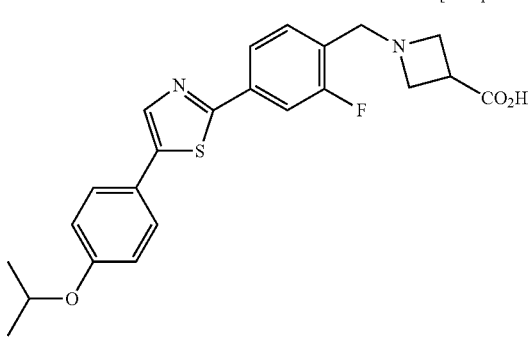
[Compound 14]
Example 22
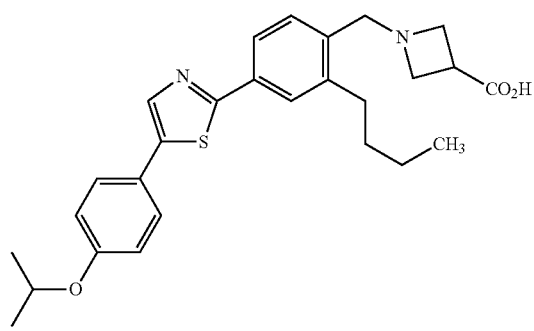
Example 19
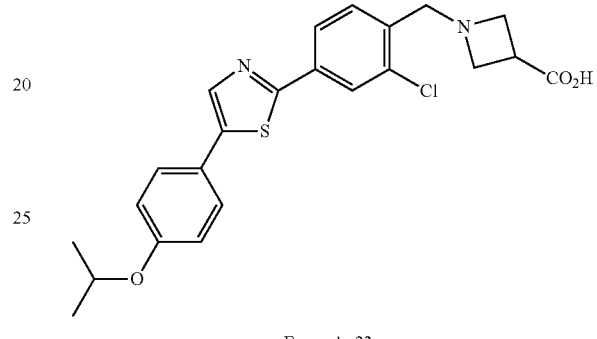
Example 23
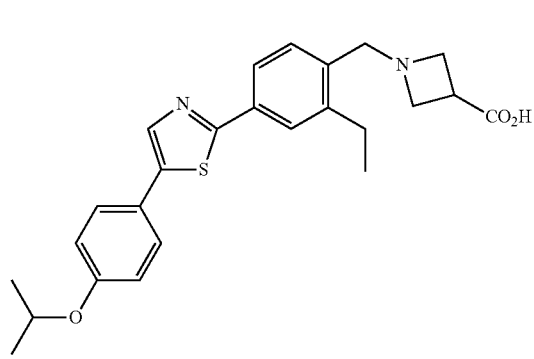
Example 20
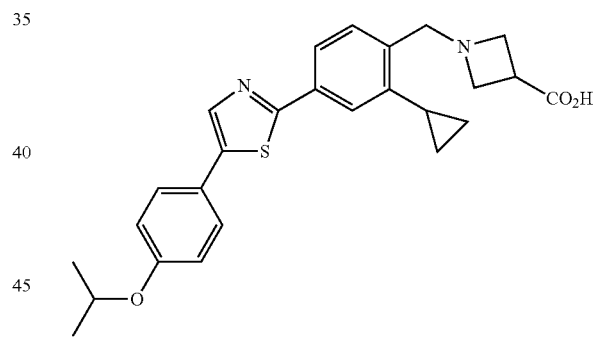
Example 24
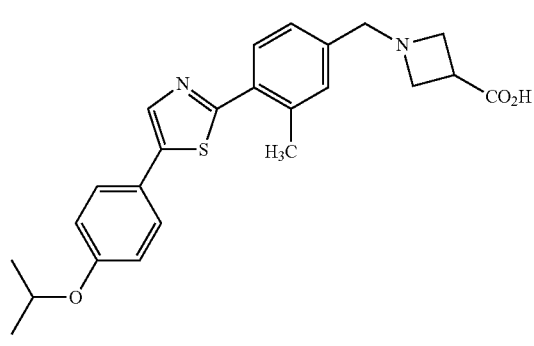
Example 21
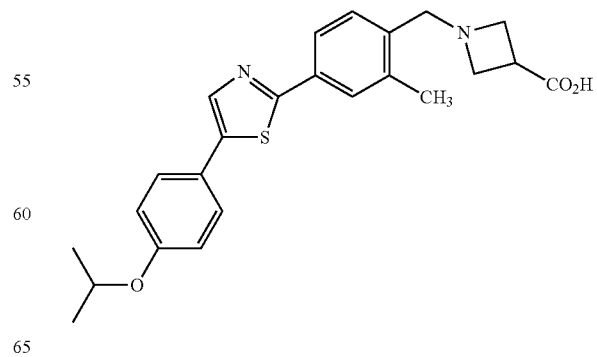
Example 25

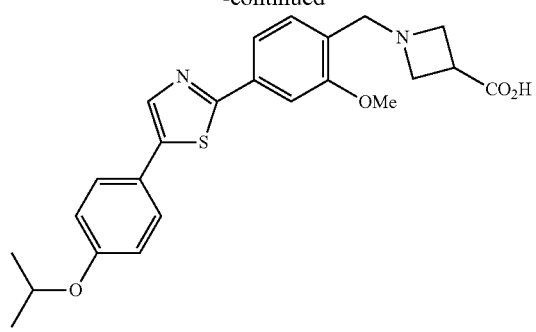
Example 26
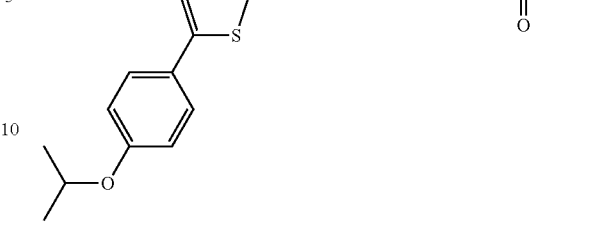
Example 30
[Compound 15]
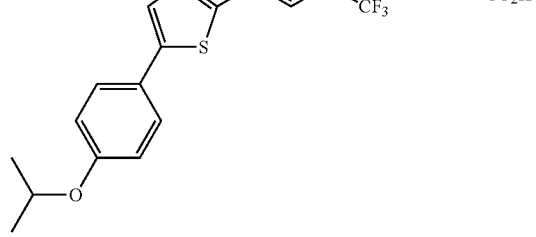
Example 27
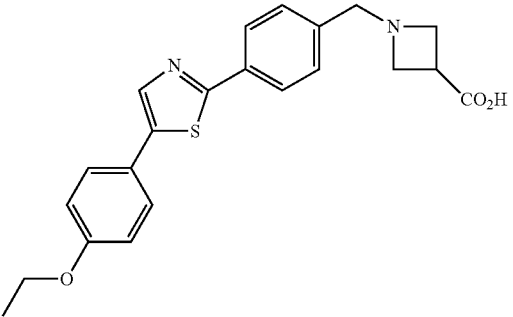
Example 31
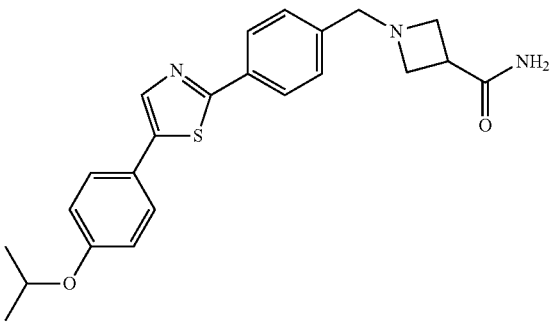
Example 28
[Compound 16]
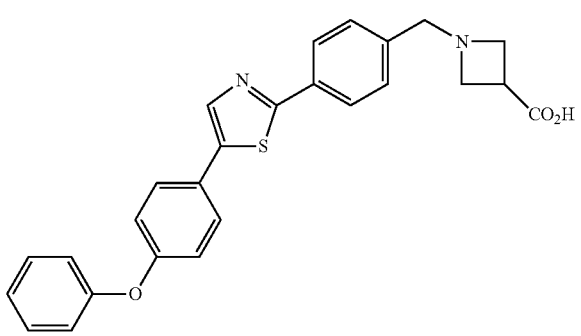
Example 32
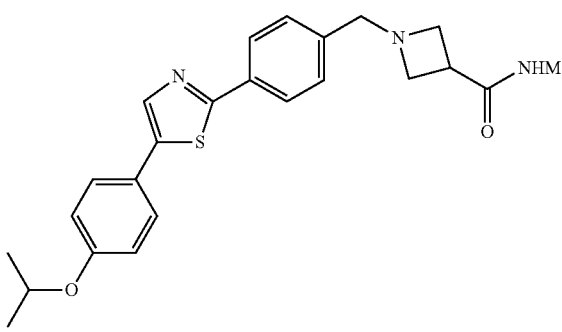
Example 29
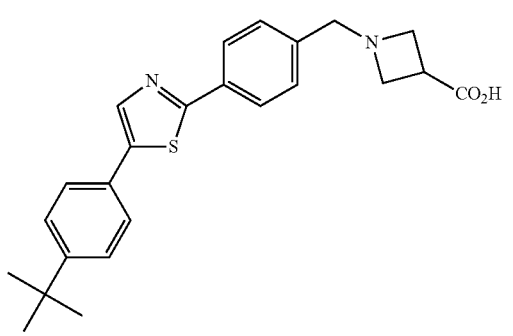
Example 33

-continued
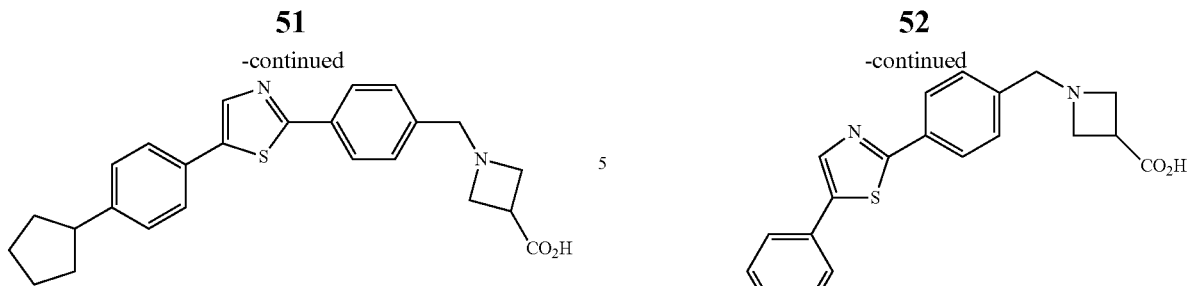
Example 34
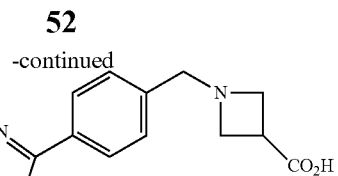
Example 38
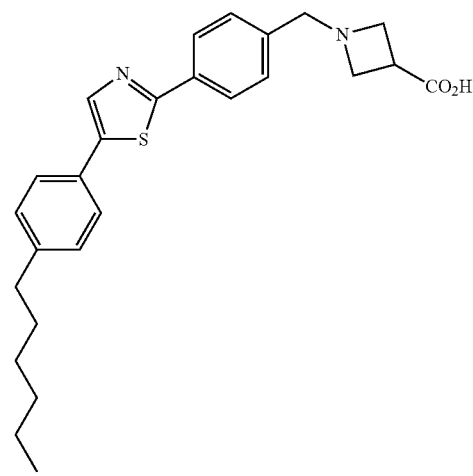
Example 35
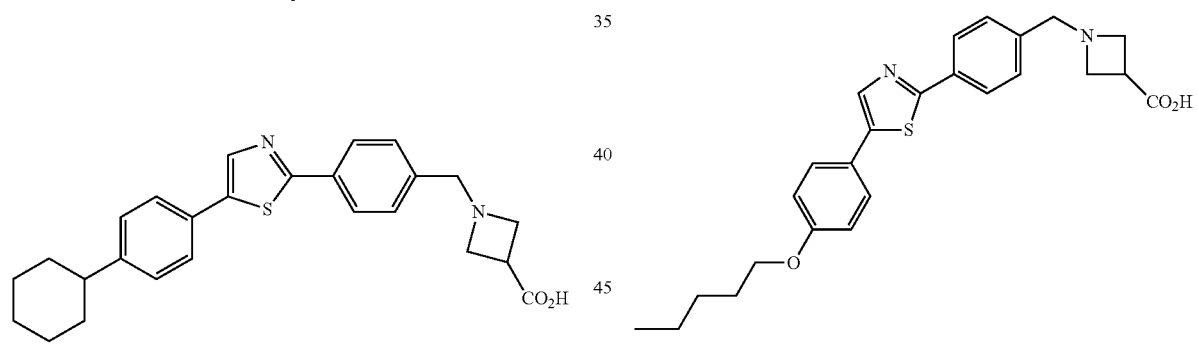
Example 39
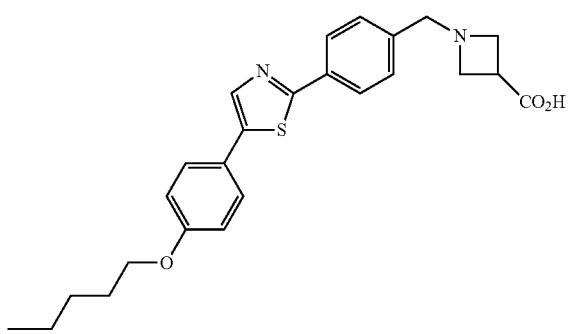
Example 36
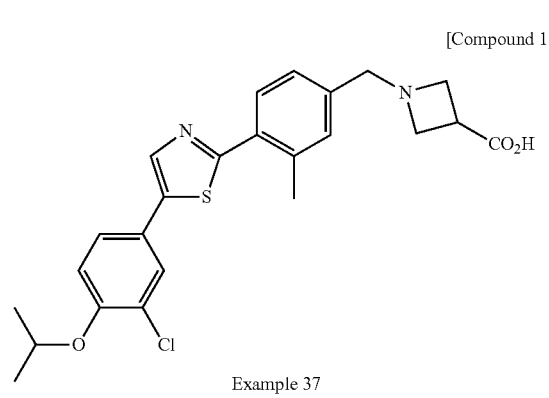
Example 40
[Compound 17]
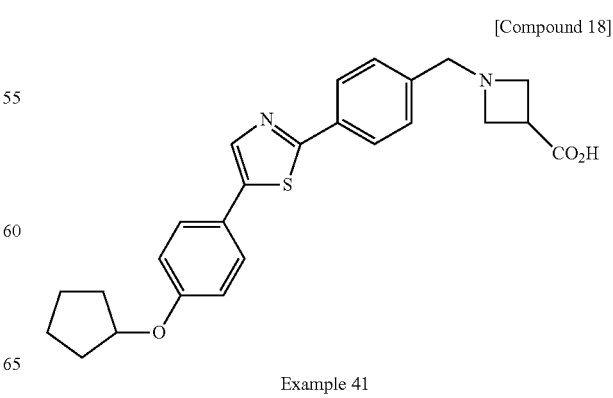
Example 37
[Compound 18]
Example 41

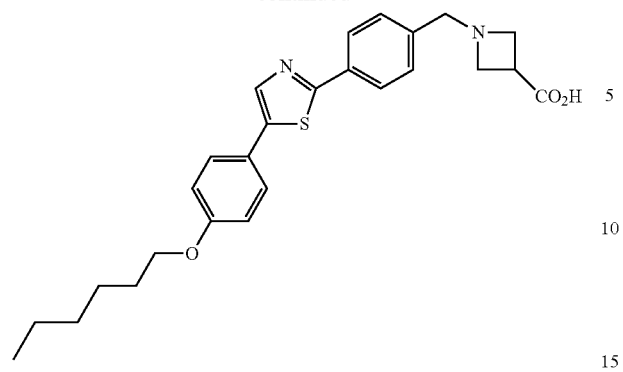
Example 42
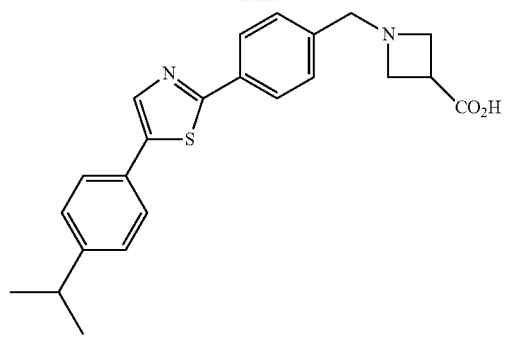
Example 46
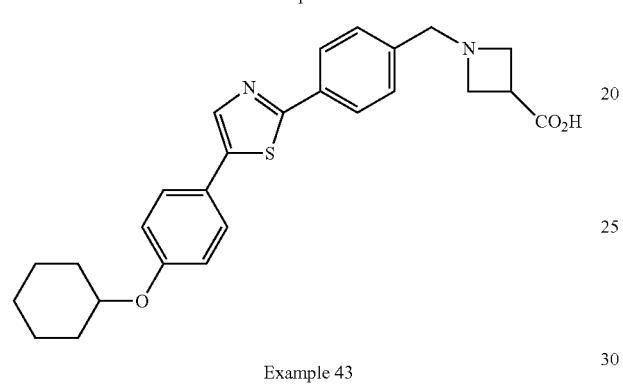
Example 43
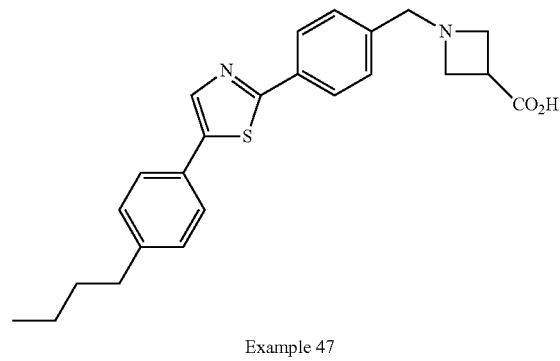
Example 47
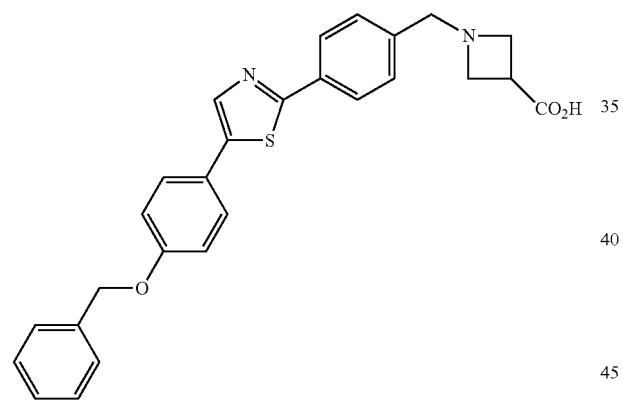
Example 44
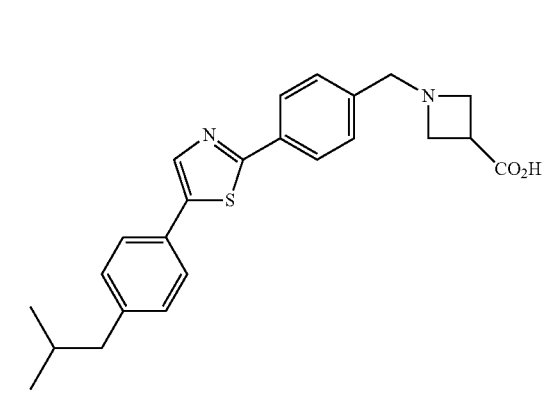
Example 48
[Compound 19]
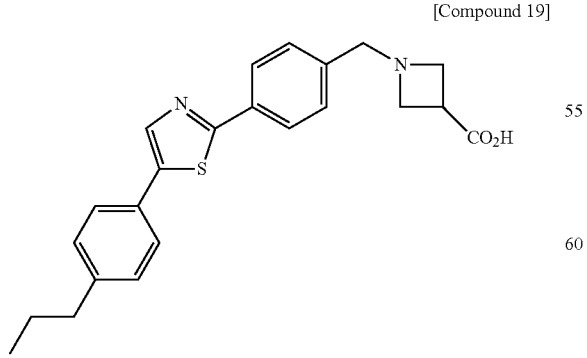
Example 45
[Compound 20]
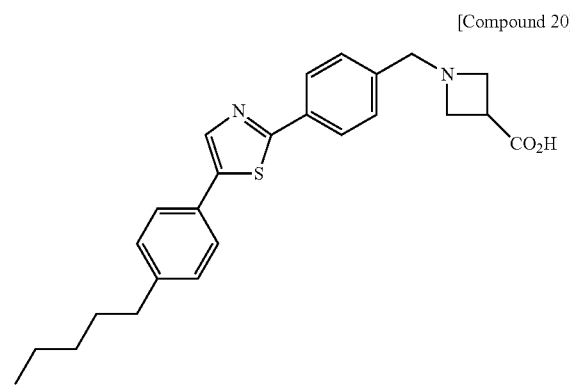
Example 49

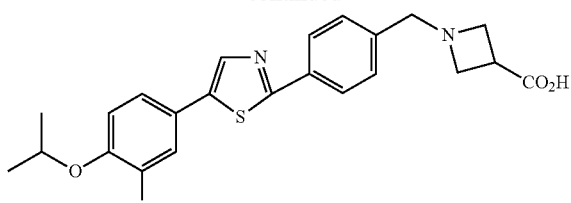
Example 50
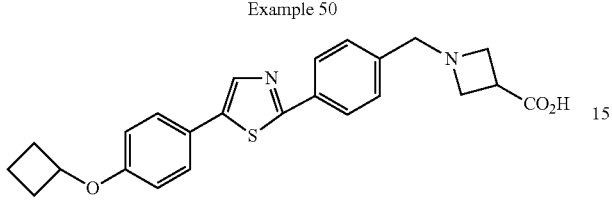
Example 51
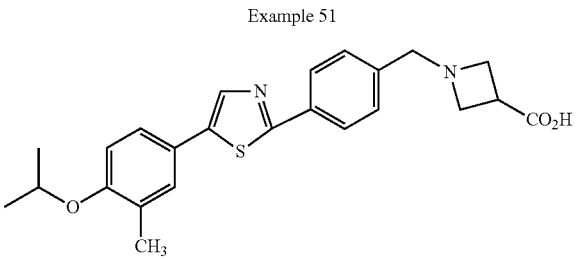
Example 52
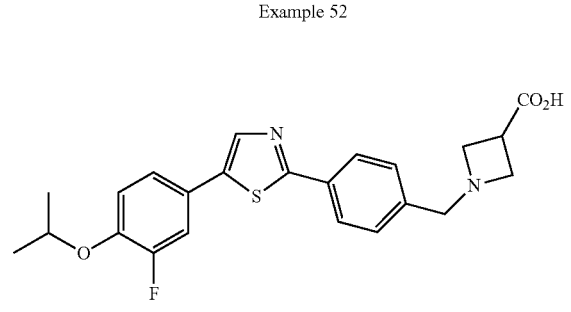
Example 53
[Compound 21]
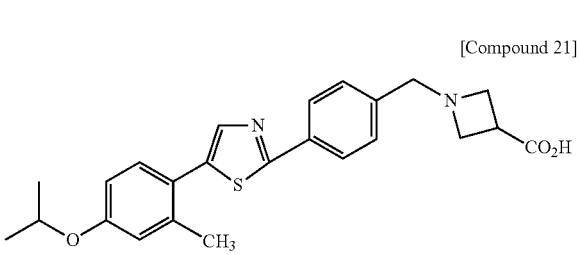
Example 54
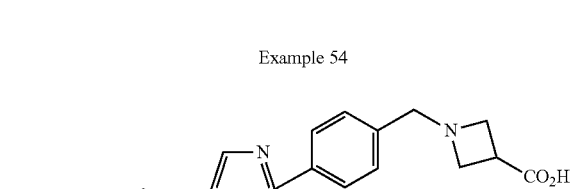
Example 55
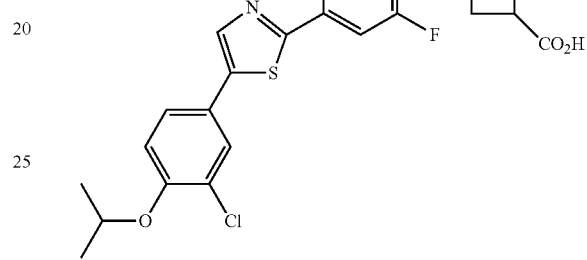
Example 56
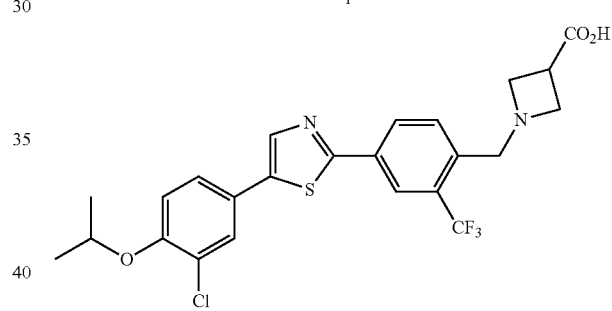
Example 57
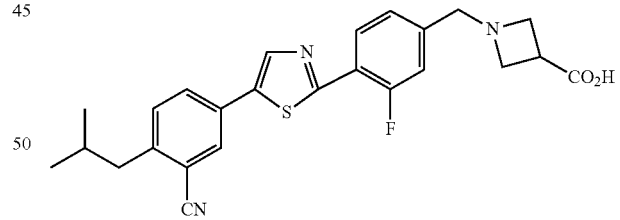
Example 58
[Compound 22]
Example 59
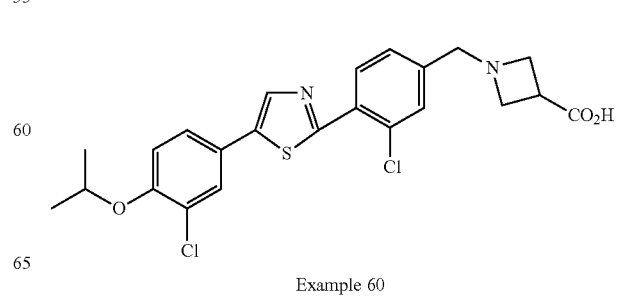
Example 60

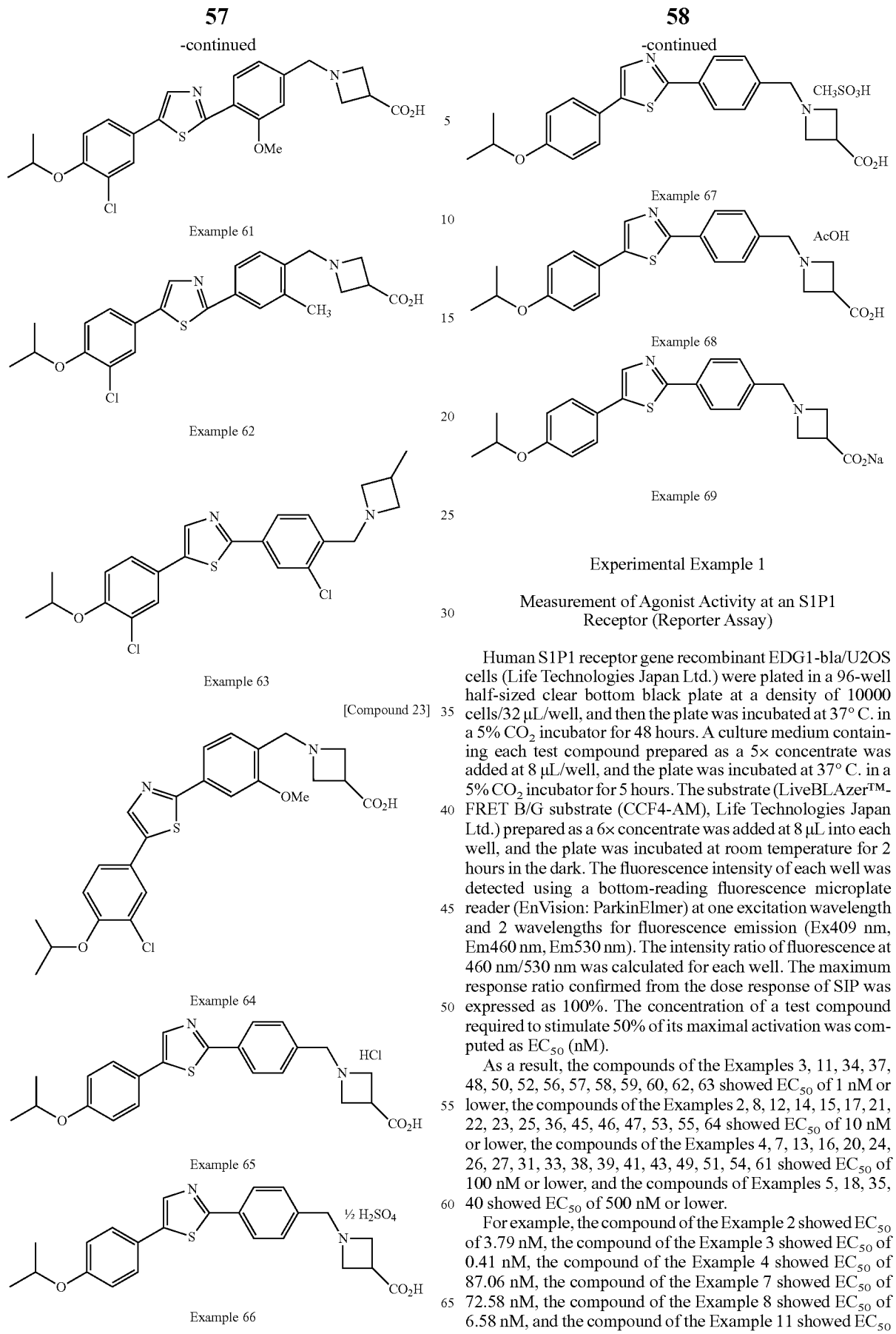

Experimental Example 1

Measurement of Agonist Activity at an S1P1 Receptor (Reporter Assay)

Human S1P1 receptor gene recombinant EDG1-bla/U2OS cells (Life Technologies Japan Ltd.) were plated in a 96-well half-sized clear bottom black plate at a density of 10000 cells/32 μL/well, and then the plate was incubated at 37° C. in a 5% $CO_2$ incubator for 48 hours. A culture medium containing each test compound prepared as a 5× concentrate was added at 8 μL/well, and the plate was incubated at 37° C. in a 5% $CO_2$ incubator for 5 hours. The substrate (LiveBLAzer™-FRET B/G substrate (CCF4-AM), Life Technologies Japan Ltd.) prepared as a 6× concentrate was added at 8 μL into each well, and the plate was incubated at room temperature for 2 hours in the dark. The fluorescence intensity of each well was detected using a bottom-reading fluorescence microplate reader (EnVision: ParkinElmer) at one excitation wavelength and 2 wavelengths for fluorescence emission (Ex409 nm, Em460 nm, Em530 nm). The intensity ratio of fluorescence at 460 nm/530 nm was calculated for each well. The maximum response ratio confirmed from the dose response of SIP was expressed as 100%. The concentration of a test compound required to stimulate 50% of its maximal activation was computed as $EC_{50}$ (nM).

As a result, the compounds of the Examples 3, 11, 34, 37, 48, 50, 52, 56, 57, 58, 59, 60, 62, 63 showed $EC_{50}$ of 1 nM or lower, the compounds of the Examples 2, 8, 12, 14, 15, 17, 21, 22, 23, 25, 36, 45, 46, 47, 53, 55, 64 showed $EC_{50}$ of 10 nM or lower, the compounds of the Examples 4, 7, 13, 16, 20, 24, 26, 27, 31, 33, 38, 39, 41, 43, 49, 51, 54, 61 showed $EC_{50}$ of 100 nM or lower, and the compounds of Examples 5, 18, 35, 40 showed $EC_{50}$ of 500 nM or lower.

For example, the compound of the Example 2 showed $EC_{50}$ of 3.79 nM, the compound of the Example 3 showed $EC_{50}$ of 0.41 nM, the compound of the Example 4 showed $EC_{50}$ of 87.06 nM, the compound of the Example 7 showed $EC_{50}$ of 72.58 nM, the compound of the Example 8 showed $EC_{50}$ of 6.58 nM, and the compound of the Example 11 showed $EC_{50}$ of 0.076 nM.

From these results, it was confirmed that all the compounds in the present invention had strong agonist activity at an S1P1 receptor, especially, the compounds of the Examples 3, 11, 34, 37, 48, 50, 52, 56, 57, 58, 59, 60, 62, 63 have extremely strong agonist activity at an S1P1 receptor. Also, all the compounds for which $EC_{50}$ was calculated showed a dose dependency and full agonist activity.

Experimental Example 2

Measurement of Agonist Activity at an S1P1 Receptor (Measurement by GTP Exchange Reaction)

By using membrane fractions prepared from a human S1P1 receptor expressing cells (Multispan Ltd.), the agonist activity of each test compound was measured by $[^{35}S]$-GTPγS exchange reaction in accordance with a standard procedure (Methods in Molecular Biology, Vol. 552, p 143-151 (2009)), and $EC_{50}$ (nM) of each test compound was computed.

As a result, the compounds of the Examples 3, 11, 22, 34, 37, 60, 61, 62, 64 showed $EC_{50}$ of 10 nM or lower, the compounds of the Examples 2, 12, 17, 21, 23, 31, 38, 45, 46, 47, 48, 50, 52, 57, 58, 59, 63 showed $EC_{50}$ of 50 nM or lower, the compounds of the Examples 8, 36, 56 showed $EC_{50}$ of 100 nM or lower, the compounds of the Examples 51, 53, 55 showed $EC_{50}$ of 500 nM or lower.

From these results, all the compounds in the present invention have affinities to a S1P1 receptor, especially, the compounds of the Examples 3, 11, 22, 34, 37, 60, 61, 62, 64 showed extremely strong affinities to an S1P1 receptor.

Experimental Example 3

Measurement of Agonist Activity at a S1P3 Receptor (Reporter Assay)

Human S1P3 receptor gene recombinant EDG3-Galpha15-NFAT-bla HEK293T cells (Life Technologies Japan Ltd.) were plated into a 384-well clear bottom black plate treated with poly-D-lysine at a density of 1000 cells/32 μL/well, and the plate was cultured at 37° C. in a 5% $CO_2$ incubator for 16-24 hours. A culture medium containing each test compound prepared as a 5× concentrate was added at 8 μL/well, and the plate was incubated at 37° C. in a 5% $CO_2$ incubator for 5 hours. The substrate (LiveBLAzer™-FRET B/G substrate (CCF4-AM), Life Technologies Japan Ltd.) was prepared as a 6× concentrate was added at 8 μL to each well, and the plate was incubated at room temperature for 2 hours in the dark. The fluorescence intensity of the test samples was measured using a bottom-reading fluorescence microplate reader at one excitation wavelength and 2 wavelengths for fluorescence emission (Ex409 nm, Em460 nm, Em530 nm). The intensity ratio of fluorescence at 460 nm/530 nm was calculated for the compound at each well. The maximum response ratio confirmed from the dose response of S1P was expressed as 100%. The concentration of test compounds required to stimulate 50% of its maximal activation was computed as $EC_{50}$ (nM).

As a result, the compounds of the Examples 2 and 3 showed $EC_{50}$ of 2000 nM or higher.

From these results, it was demonstrated that the compounds in the present invention showed an extremely weak agonist activity at an S1P3 receptor.

Experimental Example 4

Measurement of Agonist Activity at an S1P3 Receptor (Measurement by GTP Exchange Reaction)

By using membrane fractions prepared from Human S1P3 receptor expressing cells (Multispan Inc.), the agonist activity of the compound in the present invention was measured by a $[^{35}S]$-GTPγS exchange reaction at 1000 nM by the similar method of the Experimental Example 2.

As a result, the compounds of the Examples 3, 11, 12, 21, 37, 48, 50, 51, 52, 53, 56, 60, 62 showed $EC_{50}$ of 1000 nM, showing 20% to less than 50% of the maximal agonist activity. The compounds of the Examples 2, 15, 22, 23, 31, 34, 36, 38, 45, 46, 47, 55, 57, 58, 59, 61, 63, 64 showed $EC_{50}$ of 1000 nM and the activity remained less than 20% of its maximal activity.

From these results, it was demonstrated that the compounds in the present invention had extremely low affinity to a S1P3 receptor.

Experimental Example 5

Measurement of Agonist Activity at a S1P4 Receptor (Reporter Assay)

Human S1P4 receptor gene recombinant EDG6-bla/U2OS cells (Life Technologies Japan Ltd.) were seeded into each well of a 384-well clear bottom black plate treated with poly-D-lysine at a density of 10000 cells/32 μL/well and cultured at 37° C. in a 5% $CO_2$ incubator for 16 to 24 hours. A culture medium containing each test compound prepared as a 5× concentrate was added at 8 μL/well, and the plate was cultured at 37° C. in a 5% $CO_2$ incubator for 5 hours. The substrate (LiveBLAzer™-FRET B/G substrate (CCF4-AM), Life Technologies Japan Ltd.) prepared as a 6× concentrate was added at 8 μL to each well, and the plate was incubated for 2 hours in the dark. The fluorescence intensity of the test samples was measured using bottom-reading fluorescence microplate reader at one excitation wavelength and 2 wavelengths for fluorescence emission (Ex409 nm, Em460 nm, Em530 nm). The intensity ratio of fluorescence at 460 nm/530 nm was calculated for each well. The maximum response ratio confirmed from the dose response of S1P was expressed as 100%. The concentration of the test compound required to stimulate 50% of its maximal activation was computed as $EC_{50}$ (nM).

As a result, the compounds of the Examples 2 and 3 showed $EC_{50}$ of 2000 nM or higher.

From these results, it was confirmed that the compounds in the present invention had extremely weak agonist activities at an S1P4 receptor.

Experimental Example 6

Measurement of Agonist Activity at an S1P4 Receptor (Calcium Influx)

By using Human S1P4 receptor expressing cells (Multispan Inc. CG1052-1), the elevation of intracellular calcium concentration via agonist activity by the addition of 1000 nM was measured by Fret method (fluorescence resonance energy transfer).

As a result, the compounds of the Examples 2, 3, 8, 11, 12, 15, 17, 21, 22, 23, 31, 34, 36, 37, 38, 45, 46, 47, 48, 50, 51, 52, 53, 55, 56, 57, 58, 59, 60, 61, 62, 63, 64 showed activity of less than 20% at 1000 nM.

From these results, it was demonstrated that the compounds in the present invention had extremely weak agonist activity at an S1P4 receptor.

Experimental Example 7

Measurement of Agonist Activity at an S1P5 Receptor (Reporter Assay)

Human S1P5 receptor gene recombinant EDG8-bla/U2OS cells (Life Technologies Japan Ltd.) were plated in a 384-well clear bottom black plate at 10000 cells/32 µL/well, and the plate was incubated at 37° C. in a 5% $CO_2$ incubator for 48 hours. A culture containing each test compound prepared as a 5× concentrate was added at 8 µL/well, and the plate was incubated at 37° C. in a 5% $CO_2$ incubator for 5 hours. The substrate (LiveBLAzer™-FRET B/G substrate (CCF4-AM), Life Technologies Japan Ltd.) prepared as a 6× concentrate was added at 8 µL to each well, and the plate was incubated at room temperature for 2 hours in the dark. The fluorescence intensity of each well was measured using a bottom-reading fluorescence microplate reader at one excitation wavelength and 2 wavelengths for fluorescence emission (Ex409 nm, Em460 nm, Em530 nm). The intensity ratio of fluorescence at 460 nm/530 nm was calculated for each well. The maximum response ratio confirmed from the dose response of S1P was expressed as 100%. The concentration of test compound required to stimulate 50% of its maximal activation was determined as $EC_{50}$ (nM).

As a result, $EC_{50}$ (nM) of the compounds of the Examples 2 and 3 showed 2000 nM or higher.

From these results, it was confirmed that the compounds in the present invention had extremely weak agonist activity at an S1P5 receptor.

From the results of the Experimental Example 1 to 7, it was confirmed that the compound in the present invention was an extremely selective agonist at a S1P1 receptor.

Experimental Example 8

Suppressive Effect on Circulating Lymphocytic Cells in a Rat

Under anesthesia, a femoral artery was cannulated in a 7-11-week old male SD rat (Charles River Laboratories Japan Inc.) that had been reared for more than one week. A vehicle (in case of intravascular administration, 10% PEG300-0.01 M KOH saline was used, and in case of oral administration, 0.5% hydroxymethyl cellulose solution was used) or a test compound was administered intravascularly or by gavage administration. Right before the administration or 2, 4, 6 hours after the administration, the number of blood lymphocytic cells was counted by using an automated hematology analyzer XT-1800i or XT-2000i (Sysmex). The count of lymphocytic cells right before the administration was regarded as 100%, and the dose of the test compound that reduced blood lymphocytic cells by 50% of vehicle-treated group at the point of 6 hours after the administration was calculated as $ED_{50}$ (mg/kg body weight).

As a result, $ED_{50}$ of Fingolimod (saline as a solvent) was 0.06 mg/kg body weight when it was administered vascularly, and 0.2 mg/kg body weight for gavage administration. On the contrary, $ED_{50}$ of the compound as shown in the Example 2 was 0.1 mg/kg body weight for vascular administration, and 0.13 mg/kg body weight for gavage administration. $ED_{50}$ of the compound as shown in the Example 3 was 0.016 mg/kg body weight for vascular administration, and 0.15 mg/kg body weight for gavage administration.

From these results, it was demonstrated that the compounds in the present invention had a potent suppressive effect on the count of blood circulating lymphocytic cells.

Experimental Example 9

Evaluation of the Heart Rate in a Rat (Evaluation Under Consciousness)

Under anesthesia, femoral artery was cannulated in a 7-11-week old male SD rat (Charles River Laboratories Japan Inc.) that had been reared for more than one week. Arterial cannula was connected to a pressure transducer, and under consciousness changes in the heart rate were monitored with a polygraph (Nihon Kohden) up to 4 hours after the vascular administration of the vehicle (10% PEG300-0.01M KOH saline) or the test compounds. The dose that lowered the heart rate by 20% was computed as $TD_{20}$ (mg/kg body weight).

As a result, when Fingolimod (saline as vehicle) was vascularly administrated, $TD_{20}$ was 0.3 mg/kg body weight, and the $TD_{20}/ED_{50}$ ratio was 5. On the contrary, when the compound synthesized in Example 2 or Example 3 was vascularly administered at a dose of 6 mg/kg body weight, the suppression of the heart rate was not recognized.

Experimental Example 10

Evaluation of Cardiovascular System in a Guinea Pig

Under anesthesia with 0.5 to 1% of halothane, to a male Hartley guinea-pig (Japan SLC, Inc.) that had been reared for more than one week, a catheter for administration of a drug solution was placed into the left jugular vein, a monophasic action potential (MAP) measurement/pacing catheter was placed into the endothelial lining of the right ventricle, a catheter for measuring blood pressure was placed into the left carotid artery, and the measurement of body surface electrocardiogram (lead II) was conducted. The drug solution was infused for 10 minutes and the measurement was carried out over 60 minutes. Also, 5, 10, 15, 20, 30, 45 and 60 minutes after the administration of the drug solution, pacing was performed (200, 240, 300 bpm), and monophasic action potential (MAP) was measured.

As a result, when a drug solution containing Fingolimod (0.1 mg/kg body weight) was administered, a prolonged QT and the MAP90 prolongation effect, which indicate cardiotoxicity, were recognized. On the contrary, when the drug solution containing the compound (0.1 mg/kg body weight) of the Example 2 was administered, these effects were not observed.

Experimental Example 11

Study on the Collagen-Induced Arthritis Model

A solution of Type II collagen derived from bovine and Freund's complete adjuvant were mixed to prepare an emulsion. This emulsion was used to elicit collagen-induced arthritis in a 7-week-old female DBA/1JN mouse. The initial sensitization was carried out by subcutaneous administration of the emulsion in the tail of the mouse at a dose of 150 µg/100 µL/body. 21 days after the initial sensitization, a freshly prepared collagen emulsion solution was administered subcutaneously in the tail of the mouse at a dose of 100 µg/100 µL/body as a secondary sensitization. The mouse prepared in this procedure was used as the collagen-induced arthritis model. A compound suspended in 0.5% hydroxymethyl cellulose solution was orally administered by force once daily for 4 weeks following the additional second sensitization. Pathological scores including joint symptoms and the like were measured, and the results compared to the vehicle-treated group, from which the efficacy of the compound was evaluated.

As a result, it was demonstrated that the compound of the Example 2 was equally effective as Fingolimod.

Experimental Example 12

Study on the Experimental Autoimmune Encephalomyelitis Model

An emulsion of $PLP_{139-151}$/CFA was subcutaneously administered to the upper dorsal region and in the tail of an 8-week-old female SJL/J mouse at a dose of 100 µL/body. At 2 hours and 24 hours after the administration, pertussis toxin was peritoneally administered at a dose of 100 µL/body. Thus, the mouse prepared in this procedure was used as an experimental autoimmune encephalomyelitis model. The administration of the compound was started on day 12, when the pathological score showed the worst severity, and the gavage administration was continued for 28 days. The compound suspended in a solution of 0.5% hydroxypropyl methylcellulose was orally administered by force once daily. The changes in pathological score and body weight were recorded and the results compared to the vehicle-treated group, from which the efficacy of the compounds was evaluated.

As a result, it was demonstrated that the compound of the Example 2 was able to significantly inhibit pathological scores when it was orally administered once daily at a dose of 1 mg/kg body weight or more.

Experimental Example 13

Study on the TNBS-Induced Inflammatory Bowel Disease Model in a Rat

Under anesthesia, TNBS solution (2,4,6-trinitrobenzene sulphonic acid; WAKO Pure Chemical Industries, Ltd.) having a concentration of 25 mg/0.75 mL was administered rectally to a 8-week-old male SD rat at a dose of 3 mL/kg, and the region analis of the rat was capped with a rubber for 2.5 hour. Subsequently, the cap was removed and the content in the rectum was discharged. According to this procedure, the rat was used as the TNBS-induced inflammatory bowel disease model. 2 days after the elicitation, the mice were grouped and the administration of the compound was started. Compounds suspended in a solution of 0.5% hydroxymethyl cellulose were orally administered by force to mice once daily for 6 days. Changes in scores for colitis and macroscopic scores of the large intestine on the following day of the administration were assessed and compared to the vehicle-treated group to evaluate the efficacy of the compounds.

Experimental Example 14

Study of Stability Against Enterobacterium

A culture medium was added to fresh feces of a cynomolgus monkey and rat cecum to prepare homogenates. To a homogenate was added the compound of the Example 2, or 1-{4-[5-(4-isopropoxyphenyl)-1,2,4-oxadiazol-3-yl]benzyl}azetidine-3-carboxylic acid (the compound of the Example 29 of Non-Patent Document 5) adjusted at a concentration of 3 and 30 µM, and the mixture was anaerobically cultured at 37° C. for 24 hours. After the cultivation, the concentration of the residual compound in the culture medium was measured on LC-MS.

As a result, 1-{4-[5-(4-isopropoxyphenyl)-1,2,4-oxadiazol-3-yl]benzyl}azetidine-3-carboxylic acid was almost completely degraded under all the conditions (equal to or lower than 2%). However, the compound of the Example 2 remained almost completely intact.

It was demonstrated that 1-{4-[5-(4-isopropoxyphenyl)-1,2,4-oxadiazol-3-yl]benzyl}azetidine-3-carboxylic acid having an oxadiazole ring is extremely unstable to enterobacterium. On the other hand, the compound with a thiazole ring in the present invention is resistant to enterobacterium. Therefore, it has been suggested that the oral stability of the compound is attributed to the advantageous effect of its specific structure.

Experimental Example 15

Evaluation of Electrocardiogram in a Rat (Evaluation Under Anesthesia)

Under anesthesia, femoral artery was cannulated in a 7-11-week-old male SD rat (Charles River Laboratories Japan Inc.) that had been reared for more than one week, connected to a polygraph (NIHON KODEN) via a pressure transducer. Without consciousness, a vehicle (dimethylsulfoxide) or a test compound was intravenously administered. After the administration, blood pressure, the heart rate, and electrocardiogram were monitored for about 10 minutes.

As a result, when a phosphorylated form of Fingolimod was intravenously administered at a dose of 0.1 mg/kg body weight, continuous cardiac arrhythmia (AV block) for 120 seconds was recognized. Moreover, it was recognized that cardiac arrest was seen in 1 out of 3 cases, cardiac arrhythmia (AV block) continuing for 170 seconds was recognized in 2 cases, when 1-{4-[5-(4-isopropoxyphenyl)-1,2,4-oxadiazol-3-yl]benzyl}azetidine-3-carboxylic acid (the compound of the Example 29 disclosed in Non-patent document 5) was intravenously administered at a dose of 0.1 mg/kg body weight.

On the contrary, continuous cardiac arrhythmia (AV block) for 10 or more seconds was not recognized when the compound shown in Example 2 was intravenously administered at a dose of 0.1 mg/kg body weight.

The advantageous effect of the compounds in the present invention was demonstrated in the Experimental Examples 8 and 11 to 13. Also, it was demonstrated that the use of the compounds in the present invention exerted extremely small adverse effects in the Experimental Examples 9, 10 and 15. Furthermore, in the Experimental Example 14, the stability of the compound in the present invention for oral administration was demonstrated.

From these results, it was confirmed that the compound in the present invention had extremely small adverse effects. It is considered that this is because the compound in the present invention was a particularly selective agonist at an S1P1 receptor.

More specifically, it was demonstrated that the compound in the present invention was an extremely selective agonist of an S1P1 receptor, having extremely small adverse effects such as cardiotoxicity and the like, which was an issue in clinical practice, and having high resistance to enterobacterium that is important for oral administration.

INDUSTRIAL APPLICABILITY

A compound of the present invention represented by formula (I) is an S1P receptor modulator having excellent selectivity for an S1P1 receptor. Therefore, an agent for treating/preventing autoimmune diseases, allergic diseases, or the like with less probability of inducing bradycardia, heart failure, and other undesired adverse effects can be provided.

The invention claimed is:

1. A compound represented by the following formula (I):

[Compound 1]

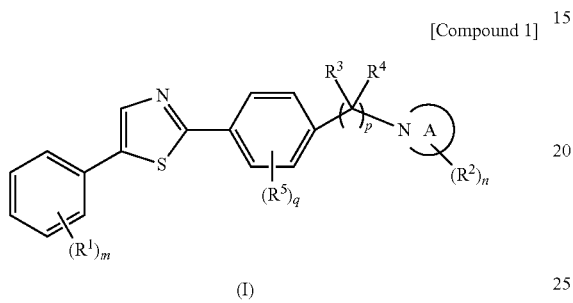

(I)

wherein
A represents a 4- to 7-membered cyclic amine;
m represents an integer of 0 to 5;
n represents an integer of 1 to 3;
p represents an integer of 1 to 3;
q represents an integer of 0 to 4;
$R^1$ represents $C_{1-10}$ alkyl, $C_{1-10}$ alkoxy, phenyl, phenoxy, phenyl $C_{1-3}$ alkyloxy, a halogen atom, halogeno $C_{1-3}$ alkyl, or cyano (when m is 2 or more, $R^1$ may be each independently identical or different);
$R^2$ represents COOH, COOR$^6$, CONR$^7$R$^8$, or tetrazolyl (when n is 2 or more, $R^2$ may be each independently identical or different);
$R^3$ represents a hydrogen atom or $C_{1-6}$ alkyl;
$R^4$ represents a hydrogen atom or $C_{1-6}$ alkyl;
or $R^3$ and $R^4$ may together form an oxo group (when p is 2 or more, $R^3$ and $R^4$ may be each independently identical or different);

$R^5$ represents $C_{1-6}$ alkyl, $C_{1-6}$ alkoxy, a halogen atom, halogeno $C_{1-3}$ alkyl, cyano, hydroxyl, or amino (when q is 2 or more, $R^5$ may be each independently identical or different);
$R^6$ represents $C_{1-10}$ alkyl; and
$R^7$ and $R^8$ each independently represent a hydrogen atom or $C_{1-10}$ alkyl, or a pharmaceutically acceptable salt thereof.

2. The compound according to claim 1 or a pharmaceutically acceptable salt thereof, wherein n is 1; and p is 1.

3. The compound according to claim 1 or a pharmaceutically acceptable salt thereof, wherein
A represents a 4- to 6-membered cyclic amine;
m represents an integer of 0 to 2;
n is 1;
p is 1;
q is an integer of 0 to 1;
$R^1$ represents $C_{1-6}$ alkyl, $C_{1-6}$ alkoxy, phenoxy, benzyloxy, a halogen atom, halogeno $C_{1-3}$ alkyl, or cyano (when m is 2, $R^1$ may be each independently identical or different);
$R^2$ represents COOH, COOR$^6$, CONR$^7$R$^8$, or tetrazolyl;
$R^3$ represents a hydrogen atom or methyl;
$R^4$ represents a hydrogen atom or methyl;
$R^5$ represents $C_{1-6}$ alkyl, $C_{1-6}$ alkoxy, halogen, or halogeno $C_{1-3}$ alkyl;
$R^6$ represents $C_{1-6}$ alkyl; and
$R^7$ and $R^8$ each independently represent a hydrogen atom or methyl.

4. The compound according to claim 1 or a pharmaceutically acceptable salt thereof, wherein $R^2$ represents COOH.

5. A pharmaceutical composition comprising, as an active ingredient, the compound according to claim 1 or a pharmaceutically acceptable salt thereof.

6. A pharmaceutical composition comprising, as an active ingredient, the compound according to claim 1 or a pharmaceutically acceptable salt thereof, and a pharmaceutically acceptable carrier or diluting agent.

7. A method for treating rheumatoid arthritis, multiple sclerosis, inflammatory bowel disease or psoriasis, comprising administering a therapeutically safe and effective amount of the compound according to claim 1 or a pharmaceutically acceptable salt thereof to a mammal in need thereof.

* * * * *